United States Patent
Chiamvimonvat et al.

(10) Patent No.: US 11,723,929 B2
(45) Date of Patent: Aug. 15, 2023

(54) METHODS OF IMPROVING CELL-BASED THERAPY

(71) Applicant: THE REGENTS OF THE UNIVERSITY OF CALIFORNIA, Oakland, CA (US)

(72) Inventors: Nipavan Chiamvimonvat, Davis, CA (US); Bruce D. Hammock, Davis, CA (US); Padmini Sirish, Davis, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 452 days.

(21) Appl. No.: 16/621,649

(22) PCT Filed: Jun. 11, 2018

(86) PCT No.: PCT/US2018/036891
§ 371 (c)(1),
(2) Date: Dec. 11, 2019

(87) PCT Pub. No.: WO2018/231702
PCT Pub. Date: Dec. 20, 2018

(65) Prior Publication Data
US 2021/0145891 A1 May 20, 2021

Related U.S. Application Data

(60) Provisional application No. 62/519,092, filed on Jun. 13, 2017.

(51) Int. Cl.
*C12N 5/074* (2010.01)
*A61K 35/34* (2015.01)
(Continued)

(52) U.S. Cl.
CPC .......... *A61K 35/34* (2013.01); *A61K 31/453* (2013.01); *A61K 45/06* (2013.01); *A61L 31/16* (2013.01); *C12Y 303/0201* (2013.01)

(58) Field of Classification Search
CPC .................................................. C12N 5/0607
See application file for complete search history.

(56) References Cited

U.S. PATENT DOCUMENTS

| | | |
|---|---|---|
| 10,369,141 B2 | 8/2019 | Chiamvimonvat et al. |
| 2004/0176281 A1 | 9/2004 | Toth et al. |

(Continued)

FOREIGN PATENT DOCUMENTS

| | | |
|---|---|---|
| WO | WO-2012082647 A2 | 6/2012 |
| WO | WO-2019106066 A1 | 6/2019 |
| WO | WO-2019149178 A1 | 8/2019 |

OTHER PUBLICATIONS

Xu et al., "A potent soluble epoxide hydrolase inhibitor, t-AUCB, acts through PPARy to modulate the function of endothelial progenitor cells from patients with acute myocaridal infarction", Int J Cardiol 167(4):1-18, 2013.*

(Continued)

*Primary Examiner* — Rosanne Kosson
(74) *Attorney, Agent, or Firm* — Mintz, Levin, Cohn, Ferris, Glovsky & Popeo, P.C.

(57) ABSTRACT

Provided are methods for improving the efficacy and success of cell-based therapies by administration of stem cells which have been preconditioned with an inhibitor of soluble epoxide hydrolase (sEHI), as well as kits, stents and patches for administering sEHI-preconditioned stem cells, as sole active agent or in combination with an agent that increases the production and or levels of EETs.

16 Claims, 10 Drawing Sheets

(51) Int. Cl.
   A61K 31/453    (2006.01)
   A61K 45/06     (2006.01)
   A61L 31/16     (2006.01)

(56) References Cited

U.S. PATENT DOCUMENTS

| | | |
|---|---|---|
| 2011/0077212 A1 | 3/2011 | Seed et al. |
| 2012/0172320 A1 | 7/2012 | Chen et al. |
| 2015/0164856 A1 | 6/2015 | Reiche et al. |
| 2018/0148420 A1 | 5/2018 | Casimiro-Garcia et al. |

OTHER PUBLICATIONS

Al et al., Soluble epoxide hydrolase plays an essential role in angiotensin II-induced cardiac hypertrophy, Proc Natl Acad Sci U S A, 2009, pp. 564-569, vol. 106(2).
Amano et al., Structural insights into binding of inhibitors to soluble epoxide hydrolase gained by fragment screening and X-ray crystallography, Bioorganic & Medicinal Chemistry, 2014, pp. 2427-2434, vol. 22(8).
Argiriadi et al., Detoxification of environmental mutagens and carcinogens: Structure, mechanism, and evolution of liver epoxide hydrolase, Proc Natl Acad Sci U S A, 1999, pp. 10637-10642, vol. 96(19).
Argiriadi et al., Binding of Alkylurea Inhibitors to Epoxide Hydrolase Implicates Active Site Tyrosines in Substrate Activation, The Journal of Biological Chemistry, 2000, pp. 15265-15270, vol. 275(20).
Aurora et al., Immune Modulation of Stem Cells and Regeneration, Cell Stem Cell, 2014, pp. 14-25, vol. 15(1).
Chen et al., Cardiovascular Molecular Imaging: Focus on Clinical Translation, Circulation, 2011, pp. 425-443, vol. 123(4).
Chiamvimonvat et al., The Soluble Epoxide Hydrolase as a Pharmaceutical Target for Hypertension, J Cardiovasc Pharmacol, 2007, pp. 225-237, vol. 50(3).
Chimenti et al., Relative Roles of Direct Regeneration Versus Paracrine Effects of Human Cardiosphere-Derived Cells Transplanted Into Infarcted Mice, Circ Res, 2010, pp. 971-980, vol. 106(5).
Cohn et al., Effect of Vasodilator Therapy on Mortality in Chronic Costive Heart Failure: Results of a Veterans Administration Cooperative Study, N Engl J Medthe New England Journal of Medicine, 1986, pp. 1547-1552, vol. 314, No. 24.
Dimmeler et al., Cell Therapy of Acute Myocardial Infarction: Open Questions, Cardiology, 2009, pp. 155-160, vol. 113(3).
Dimmeler et al., Stem Cells Review Series: AI introduction, Circ Res, 2011, pp. 907-909, vol. 109(8).
Dominguez et al., Trends of congestive heart failure epidemiology: contrast with clinical trial results, Cardiologia. 1999, pp. 801-808, vol. 44(9).
Don et al., Improving survival and efficacy of pluripotent stem cell-derived cardiac grafts, Journal of Cellular and Molecular Medicine, 2013, pp. 1355-1362, vol. 17(11).
Garriga et al., Insights into the structure of urea-like compounds as inhibitors of the juvenile hormone epoxide hydrolase (JHEH) of the tobacco hornworm *Manduca sexta*: Analysis of the binding modes and structure-activity relationships of the inhibitors by docking and CoMFA calculations, Chemosphere, 2011, pp. 1604-1613, vol. 82(11).
Gerbin et al., The winding road to regenerating the human heart, Cardiovascular Pathology, 2015, pp. 133-140, vol. 24(3).
Giordano, Oxygen, oxidative stress, hypoxia, and heart failure, The Journal of Clinical Investigation, 2005, pp. 500-508, vol. 115(3).
Gomez et al., Structure of Human Epoxide Hydrolase Reveals Mechanistic Inferences on Bifunctional Catalysis in Epoxide and Phosphate Ester Hydrolysis, Biochemistry, 2004, pp. 4716-4723, vol. 43(16).
Gomez, et al., Human soluble poxide hydrolase: Structural basis of inhibition by 4-(3-cyclohexylureido)-carboxylic acids, Protein Science, 2006, pp. 58-64, vol. 15(1).
Harris et al., The Potential of Soluble Epoxide Hydrolase Inhibition in the Treatment of Cardiac Hypertrophy, Congest Heart Fail., 2008, pp. 219-224, vol. 14(4).
Ho et al., The Epidemiology of Heart Failure: Tthe Framingham Study, Journal of the American College of Cardiology, 1993, pp. 6A-13A, vol. 22(4 Suppl A).
Hwang et al., Orally Bioavailable Potent Soluble Epoxide Hydrolaselnhibitors, J Med Chem, 2007, pp. 3825-3840, vol. 50(16).
Hwang et al., Synthesis and Structure-Activity Relationship Studies of Urea-Containing Pyrazoles as Dual Inhibitors of Cyclooxygenase-2 and Soluble Epoxide Hydrolase, J Med Chem, Apr. 28, 2011, pp. 3037-3050, vol. 54(8).
Laflamme et al., Cardiomyocytes derived from human embryonic stem cells in pro-survival factors enhance function of infarcted rat hearts, Nature Biotechnology, Sep. 2007, pp. 1015-1024, vol. 25(9).
Lalit et al., iPS Cells for Post-myocardial Infarction Repair: Remarkable Opportunities and Challenges, Circ Res., 2014, pp. 1328-1345, vol. 114(8).
Lee et al., Imaging of Embryonic Stem Cell Migration In Vivo, Methods Mol Biol, 2011, pp. 101-114, vol. 750.
Levy et al., Prognostic Implications of Echocardiographically Determined Left Ventricular Mass in the Framingham Heart Study, New England Journal of Medicine, 1990, pp. 1561-1566, vol. 322(22).
Li et al., Beneficial Effects of Soluble Epoxide Hydrolase Inhibitors in Myocardial Infarction Model: Insight Gained Using Metabolomic Approaches, J Mol Cell Cardiol., 2009, pp. 835-845, vol. 47(6).
Li et al., Use of Metabolomic Profiling in the Study of Arachidonic Acid Metabolism in Cardiovascular Disease, Congest Heart Fail., 2011, pp. 42-46, vol. 17(1).
Lian et al., Robust cardiomyocyte differentiation from human pluripotent stem cells via temporal modulation of canonical Wnt signaling, Proc Natl Acad Sci U S A, 2012, pp. E1848-E1857, vol. 109(27).
Lian et al., Directed cardiomyocyte differentiation from human pluripotent stem cells by modulating Wnt/β-catenin signaling under fully defined conditions, Nature protocols, 2013, pp. 162-175, vol. 8(1).
Liu et al., Inhibition of soluble epoxide hydrolase enhances the anti-inflammatory effects of aspirin and 5-lipoxygenase activation protein inhibitor in a murine model, Biochem Pharmacol, 2010, pp. 880-887, vol. 79(6).
Liu et al., Metabolic profiling of murine plasma reveals an unexpected biomarker in rofecoxib-mediated cardiovascular events, Proc Natl Acad Sci U S A, 2010, pp. 17017-17022, vol. 107(39).
Maekawa et al., Survival and Cardiac Remodeling After Myocardial Infarction are Critically Ddependent on the Host Innate Immune Interleukin-1 Receptor-Associated Kinase-4 Signaling: A Regulator of Bone Marrow-Derived Dendritic Cells, Circulation, 2009, pp. 1401-1414, vol. 120(14).
Morisseau et al., Epoxide Hydrolases: Mechanisms, Inhibitor Designs, and Bbiological Roles, Annu. Rev. Pharmacol. Toxicol., 2005, pp. 311-333, vol. 45.
Morisseau et al., Potent urea and carbamate inhibitors of soluble epoxide hydrolases, Proc Natl Acad Sci U S A, 1999, pp. 8849-8854, vol. 96(16).
Moser et al., Evaluation of structure-derived pharmacophore of soluble epoxide hydrolase inhibitors by virtual screening, Bioorganic & Medicinal Chemistry Letters, 2012, pp. 6762-6765, vol. 22(21).
Mozaffarian et al., Heart Disease and Stroke Statistics—2016 Update: A Report From the American Heart Association, Circulation, 2016, pp. e38-360, vol. 133(4).
Qiu et al., Soluble Epoxide Hydrolase Inhibitors and Heart Failure, Cardiovasc Ther., Apr. 2011, pp. 99-111, vol. 29(2).
Robey, et al., Systems approaches to preventing transplanted cell death in cardiac repair, J Mol Cell Cardiol, 2008, pp. 567-581, vol. 45(4).
Rodrigues et al., Production of Reactive Oxygen Species by Multipotent Stromal Cells/Mesenchymal Stem Cells Upon Exposure to Fas Ligand, Cell Transplant., 2012, pp. 2171-2187, vol. 21(10).
Sarkissian et al., Optimizing stem cells for cardiac repair: Current status and new frontiers in regenerative cardiology, World Journal of Stem Cells, Jan. 26, 2017, pp. 9-25, vol. 9(1).

(56) References Cited

OTHER PUBLICATIONS

Shi et al., Improving outcome of transplanted mesenchymal stem cells for ischemic heart disease, Biochemical and Biophysical Research Communications, 2008, pp. 247-250, vol. 376(2).

Singla et al., Transplantation of embryonic stem cells into the infarcted mouse heart: formation of multiple cell types, Journal of Molecular and Cellular Cardiology, 2006, pp. 195-200, vol. 40(1).

Sirish et al., Unique mechanistic insights into the beneficial effects of soluble epoxide hydrolase inhibitors in the prevention of cardiac fibrosis, Proc Natl Acad Sci U S A, Apr. 2, 2013, pp. 5618-5623, vol. 110(14).

Sirish et al., Molecular Mechanisms and New Treatment Paradigm for Atrial Fibrillation, Circulation Arrhythmia and Electrophysiology, May 2016, vol. 9(5).

Spector et al., Epoxyeicosatrienoic acids (EETs): metabolism and biochemical function, Progress in Lipid Research, 2004, pp. 55-90, vol. 43(1).

Takahashi et al., Induction of Pluripotent Stem Cells from Mouse Embryonic and Adult Fibroblast Cultures by Defined Factors, Cell, 2006, pp. 663-676, vol. 126(4).

Takai et al., Three-dimensional rational approach to the discovery of potent substituted cyclopropyl urea soluble epoxide hydrolase inhibitors, Bioorganic & Medicinal Chemistry Letters, 2015, pp. 1705-1708, vol. 25(8).

Ulu et al., Pharmacokinetics and in vivo potency of soluble epoxide hydrolase inhibitors in cynomolgus monkeys, British Journal of Pharmacology, 2012, pp. 1401-1412, vol. 165(5).

Wollert et al., Clinical Applications of Stem Cells for the Heart, Circulation Research, 2005, pp. 151-163, vol. 96.

Xing et al., Discovery of Potent Inhibitors of Soluble Epoxide Hydrolase by Combinatorial Library Design and Structure-Based Virtual Screening, Journal of Medicinal Chemistry, 2011, pp. 1211-1222, vol. 54(5).

Xu et al., Prevention and reversal of cardiac hypertrophy by soluble epoxide hydrolase inhibitors, Proc Natl Acad Sci U S A, 2006, pp. 18733-18738, vol. 103(49).

Ye et al., Cardiac repair in a porcine model of acute myocardial infarction with human induced pluripotent stem cell-derived cardiovascular cells, Cell Stem Cell., Dec. 4, 2014, pp. 750-761, vol. 15(6).

Zhang et al., Imaging Cardiac Stem Cell Therapy: Translations to Human Clinical Studies, Journal of Cardiovascular Translational Research, 2011, pp. 514-522, vol. 4(4).

\* cited by examiner

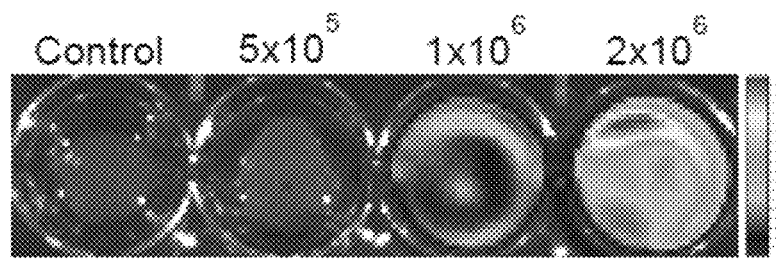
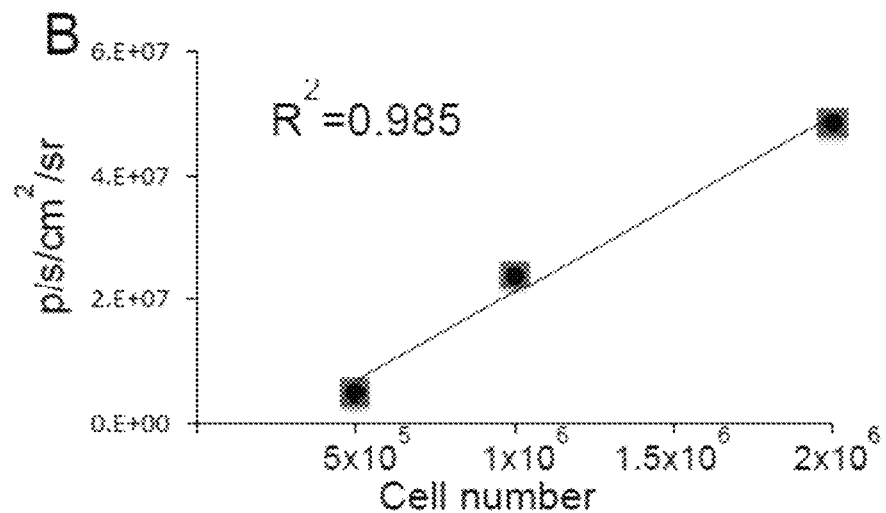
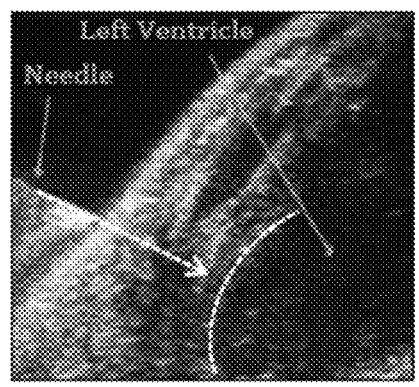
*Figure 4*

METHODS OF IMPROVING CELL-BASED THERAPY

CROSS-REFERENCE TO RELATED APPLICATIONS

This application is the U.S. National Stage Entry under § 371 of International Application PCT/US2018/036891, filed Jun. 11, 2018, which claims priority benefit to U.S. Provisional Application No. 62/519,092, filed on Jun. 13, 2017, which is hereby incorporated herein by reference in its entirety for all purposes.

FIELD

Provided are methods for improving the efficacy and success of cell-based therapies by administration of stem cells which have been preconditioned with an inhibitor of soluble epoxide hydrolase (sEHI), as well as kits, stents and patches for administering sEHI-preconditioned stem cells, as sole active agent or in combination with an agent that increases the production and or levels of EETs.

BACKGROUND

Cardiovascular disease (CVD) is the leading cause of death for both men and women in the United States. Since cardiac myocytes have limited ability to regenerate, their malfunction or significant loss due to aging or diseases can lead to lethal consequences. Recent studies have provided exciting evidence to support the notion that stem cells may offer an enormous potential for regenerative therapy.

Inflammatory responses and fibrosis arising from cardiac tissue injury remain barriers to cell therapy. Acute inflammatory responses result in the release of arachidonic acid which is metabolized into epoxyeicosatrienoic acids (EETs) with anti-inflammatory and pro-fibrinolytic effects. However, EETs are further metabolized by soluble epoxide hydrolases (sEH) to products with a significant reduction in anti-inflammatory properties.

SUMMARY

In one aspect, provided are methods of increasing, improving and/or promoting the survival, engraftment (e.g., in cardiac tissue), and/or integration of transplanted stem cells in a tissue of a subject in need thereof. In another aspect, provided are methods of reversing, mitigating and/or improving one or more symptoms associated with cardiomyopathy or cardiac arrhythmia in a subject in need thereof. In some embodiments, the methods comprise: a) exposing a population of stem cells in vitro to an agent that increases the production and/or level of epoxy fatty acids (EpFA), or mimics thereof, under conditions and for a time sufficient to increase epoxy fatty acids (EpFA) and/or inhibit soluble epoxide hydrolase in the stem cells, thereby producing preconditioned stem cells; and b) administering to the subject the preconditioned stem cells. In some embodiments, the stem cells are exposed in vitro to the agent at a concentration between about 0.1 nM to about 20 μM, e.g., at least about 0.1 nM to about 0.5 nM, 1 nM, 2 nM, nM, 10 nM, 25 nM, 50 nM, 100 nM, 250 nM, 500 nM, 750 nM, 1 μM, 2 μM, 5 μM, μM, or 20 μM. In some embodiments, the stem cells are exposed in vitro to the agent for a time period between about 0.5 days to about 10 days, e.g., at least about 0.5 days to about 1, 2, 3, 4, 5, 6, 7, 8, 9 or 10 days. In some embodiments, the preconditioned stem cells are further co-administered with an agent that increases the production and/or level of epoxy fatty acids (EpFA), or mimics thereof, (e.g., an inhibitor of soluble epoxide hydrolase).

The methods are useful in treating subject suffering a cardiomyopathy or heart failure. In some embodiments, the cardiomyopathy is hypertrophic cardiomyopathy. In some embodiments, the cardiomyopathy is hypertensive cardiomyopathy. In some embodiments, the cardiomyopathy is diabetic cardiomyopathy. In some embodiments, the cardiomyopathy is due to valvular heart disease. In some embodiments, the valvular heart disease is secondary to rheumatic fever, myxomatous degeneration of the valve, or papillary muscle dysfunction. In some embodiments, the cardiomyopathy is due to myocardial infarction. In some embodiments, the cardiomyopathy is due to ischemic cardiomyopathy. In some embodiments, the cardiomyopathy is due to restrictive cardiomyopathy. In some embodiments, the cardiomyopathy is due to familial hypertrophic cardiomyopathy. In some embodiments, the cardiomyopathy is due to arrhythmogenic right ventricular cardiomyopathy (ARVC). In some embodiments, the cardiomyopathy is dilated cardiomyopathy. In some embodiments, the dilated cardiomyopathy is alcohol- or drug-induced cardiomyopathy. In some embodiments, the dilated cardiomyopathy is viral-induced cardiomyopathy. In some embodiments, the dilated cardiomyopathy is familial dilated cardiomyopathy. In some embodiments, the dilated cardiomyopathy is idiopathic cardiomyopathy. In some embodiments, the dilated cardiomyopathy is caused by administration of an anti-cancer drug or exposure to a toxic agent. In some embodiments, the administration of said stem cells and said agent or agents inhibits cardiac arrhythmia. In some embodiments, the arrhythmia is atrial fibrillation, atrial flutter, or atrial arrhythmia. In some embodiments, the arrhythmia is ventricular fibrillation. In some embodiments, the arrhythmia is ventricular tachycardia.

In some embodiments of the methods, the agent for conditioning or exposing to the stem cells in vitro or for co-administering with the stem cells in vivo comprises one or more epoxy fatty acids (EpFA). In some embodiments, the epoxy fatty acids (EpFA) are selected from the group consisting of cis-epoxyeicosantrienoic acids ("EETs"), epoxides of linoleic acid, epoxides of eicosapentaenoic acid ("EPA"), epoxides of docosahexaenoic acid ("DHA"), epoxides of the arachidonic acid ("AA"), epoxides of cis-7,10,13,16,19-docosapentaenoic acid, and mixtures thereof. In some embodiments, the agent increases the production and/or levels of cis-epoxycicosantrienoic acids ("EETs"), or mimics thereof. In some embodiments of the methods, the agent that increases the production and/or level of EETs is an inducing agent that increases EETs biosynthesis, e.g., omeprazole. In some embodiments of the methods, the agent that increases the production and/or level of EETs is an inhibitor of soluble epoxide hydrolase ("sEH"). In some embodiments, the inhibitor of sEH (sEHI) comprises a cyclohexyl moiety, aromatic moiety, substituted aromatic moiety or alkyl moiety attached to the pharmacophore. In some embodiments, the sEHI comprises a primary or central pharmacophore selected from the group consisting of a urea, a carbamate, and an amide, or these functionalities in a nitrogen heterocycle. In some embodiments, the sEHI comprises a primary or central pharmacophore that comprises a piperidin-4-yl urea. In some embodiments, the sEHI does not comprise 1-trifluoromethoxyphenyl-3-(1-propionylpiperidin-4-yl) urea (TPPU). In some embodiments, the sEHI is selected from the group consisting of 1-(3-fluoro-4-(trifluoromethoxy)phenyl)-3-(1-(tetrahydro-2H-pyran-4-carbo-nyl)

piperidin-4-yl)urea (Compound 29 of Table 3) and 1-trifluoromethoxyphenyl-3-(1-propionylpiperidin-4-yl) urea (TPPU). In some embodiments, the sEHI does not comprise one or both of an adamantyl moiety or an azetidine moiety. In some embodiments, the inhibitor of sEH has an IC50 of less than about 100 μM. In some embodiments of the methods, the inhibitor of sEH is selected from the group consisting of:

a) 3-(4-chlorophenyl)-1-(3,4-dichlorphenyl)urea or 3,4,4'-trichlorocarbanilide (TCC; compound 295);
b) 12-(3-adamantan-1-yl-ureido) dodecanoic acid (AUDA; compound 700);
c) 1-adamantanyl-3-{5-[2-(2-ethoxyethoxy)ethoxy]pentyl}urea (AEPU; compound 950);
d) 1-(1-acetypiperidin-4-yl)-3-adamantanylurea (APAU; compound 1153);
e) trans-4-[4-(3-Adamantan-1-yl-ureido)-cyclohexyloxy]-benzoic acid (tAUCB; compound 1471);
f) cis-4-[4-(3-Adamantan-1-yl-ureido)-cyclohexyloxy]-benzoic acid (cAUCB; compound 1686);
g) 1-(1-methylsulfonyl-piperidin-4-yl)-3-(4-trifluoromethoxy-phenyl)-urea (TUPS; compound 1709);
h) trans-4-(4-[3-(4-Trifluoromethoxy-phenyl)-ureido]-cyclohexyloxy)-benzoic acid (tTUCB; compound 1728);
i) 1-trifluoromethoxyphenyl-3-(1-propionylpiperidin-4-yl) urea (TPPU; compound 1770);
j) 1-(1-ethylsulfonyl-piperidin-4-yl)-3-(4-trifluoromethoxy-phenyl)-urea (TUPSE; compound 2213);
k) 1-(1-(cyclopropanecarbonyl)piperidin-4-yl)-3-(4-(trifluoromethoxy)phenyl)urea (CPTU; compound 2214);
l) trans-N-methyl-4-[4-(3-Adamantan-1-yl-ureido)-cyclohexyloxy]-benzamide (tMAUCB; compound 2225);
m) trans-N-methyl-4-[4-((3-trifluoromethyl-4-chlorophenyl)-ureido)-cyclohexyloxy]-benzamide (tMTCUCB; compound 2226);
n) cis-N-methyl-4-(4-[3-(4-trifluoromethoxy-phenyl)-ureido]-cyclohexyloxy)-benzamide (cMTUCB; compound 2228);
o) 1-cycloheptyl-3-(3-(1,5-diphenyl-1H-pyrazol-3-yl)propyl)urea (HDP₃U; compound 2247);
p) trans-2-(4-(4-(3-(4-trifluoromethoxy-phenyl)-ureido)-cyclohexyloxy)-benzamido)-acetic acid (compound 2283);
q) N-(methylsulfonyl)-4-(trans-4-(3-(4-trifluoromethoxy-phenyl)-ureido)-cyclohexyloxy)-benzamide (compound 2728);
r) 1-(trans-4-(4-(1H-tetrazol-5-yl)-phenoxy)-cyclohexyl)-3-(4-(trifluoromethoxy)-phenyl)-urea (compound 2806);
s) 4-(trans-4-(3-(2-fluorophenyl)-ureido)-cyclohexyloxy)-benzoic acid (compound 2736);
t) 4-(4-(3-(4-(trifluoromethoxy)-phenyl)-ureido)-phenoxy)-benzoic acid (compound 2803);
u) 4-(3-fluoro-4-(3-(4-(trifluoromethoxy)-phenyl)-ureido)-phenoxy)-benzoic acid (compound 2807);
v) N-hydroxy-4-(trans-4-(3-(4-(trifluoromethoxy)-phenyl)-ureido)-cyclohexyloxy)-benzamide (compound 2761);
w) (5-methyl-2-oxo-1,3-dioxol-4-yl)methyl 4-((1r,4r)-4-(3-(4-(trifluoromethoxy)-phenyl)-ureido)-cyclohexyloxy)-benzoate (compound 2796);
x) 1-(4-oxocyclohexyl)-3-(4-(trifluoromethoxy)-phenyl)-urea (compound 2809);
y) methyl 4-(4-(3-(4-(trifluoromethoxy)-phenyl)-ureido)-cyclohexylamino)-benzoate (compound 2804);
z) 1-(4-(pyrimidin-2-yloxy)-cyclohexyl)-3-(4-(trifluoromethoxy)-phenyl)-urea (compound 2810);
aa) 4-(trans-4-(3-(4-(difluoromethoxy)-phenyl)-ureido)-cyclohexyloxy)-benzoic acid (compound 2805);
bb) (1R,3S)—N-(4-cyano-2-(trifluoromethyl)benzyl)-3-((4-methyl-6-(methylamino)-1,3,5-triazin-2-yl)amino)cyclohexane-1-carboxamide (GSK2256294A);
cc) sorafenib (4-(4-(3-(4-chloro-3-4-[[4-chloro-3-(trifluoromethyl)phenyl]carbamoylamino]phenoxy]-N-methylpyridine-2-carboxamide);
dd) regorafenib (4-[4-[[4-chloro-3-(trifluoromethyl)phenyl]carbamoylamino]-3-fluorophenoxy]-N-methylpyridine-2-carboxamide);
ee) triclocarban (3-(4-chlorophenyl)-1-(3,4-dichlorphenyl)urea or 3,4,4'-trichlorocarbanilide); and mixtures thereof. In some embodiments, the sEHI comprises a dual inhibitor of sEH and COX-2. In some embodiments, a dual inhibitor of sEH and COX-2 is administered as the sole active agent. In some embodiments, the dual inhibitor of sEH and COX-2 is 4-(5-phenyl-3-{3-[3-(4-trifluoromethyl-phenyl)-ureido]-propyl}-pyrazol-1-yl)-benzenesulfonamide (PTUPB). In some embodiments, the dual inhibitor of sEH and COX 2 is a compound in Table 4 selected from the group consisting of:

a) compound 1860 (1-Adamantan-1-yl-3-[1-(4-methanesulfonyl-phenyl)-5-phenyl-1H-pyrazol-3-ylmethyl]-urea),
b) compound 2321 (1-Cycloheptyl-3-[1-(4-methanesulfonyl-phenyl)-5-phenyl-1H-pyrazol-3-ylmethyl]-urea),
c) compound 2322 (1-[1-(4-Methanesulfonyl-phenyl)-5-phenyl-1H-pyrazol-3-ylmethyl]-3-phenyl-urea),
d) compound 2323 (1-[1-(4-Methanesulfonyl-phenyl)-5-phenyl-1H-pyrazol-3-ylmethyl]-3-(4-trifluoromethoxy-phenyl)-urea),
e) compound 2324 (1-[1-(4-Methanesulfonyl-phenyl)-5-phenyl-1H-pyrazol-3-ylmethyl]-3-(4-trifluoromethyl-phenyl)-urea),
f) compound 1861 (1-[1-(4-Methanesulfonyl-phenyl)-5-phenyl-1H-pyrazol-3-ylmethyl]-3-(3-trifluoromethyl-phenyl)-urea),
g) compound 2107 (4-{5-Phenyl-3-[3-(3-trifluoromethyl-phenyl)-ureidomethyl]-pyrazol-1-yl}-benzenesulfonamide),
h) compound 2106 (1-[5-tert-Butyl-1-(4-methanesulfonyl-phenyl)-1H-pyrazol-3-ylmethyl]-3-(3-trifluoromethyl-phenyl)-urea),
i) compound 2121 (4-{5-Phenyl-3-[3-(3-trifluoromethyl-phenyl)-ureido]-pyrazol-1-yl}-benzenesulfonamide),
j) compound 2313 (4-(5-Phenyl-3-(2-[3-(3-trifluoromethyl-phenyl)-ureido]-ethyl)-pyrazol-1-yl)-benzenesulfonamide),
compound 1862 (1-{3-[1-(4-Methanesulfonyl-phenyl)-5-phenyl-1H-pyrazol-3-yl]-propyl}-3-(3-trifluoromethyl-phenyl)-urea),
k) compound 2246 (4-(5-Phenyl-3-{3-[3-(3-trifluoromethyl-phenyl)-ureido]-propyl}-pyrazol-1-yl)-benzenesulfonamide),
l) compound 2152 (4-(5-p-Tolyl-3-{3-[3-(3-trifluoromethyl-phenyl)-ureido]-propyl}-pyrazol-1-yl)-benzenesulfonamide),
m) compound 2325 (4-(3-{3-[3-(2,6-Diisopropyl-phenyl)-ureido]-propyl}-5-phenyl-pyrazol-1-yl)-benzenesulfonamide),
n) compound 2245 (4-{5-Phenyl-3-[3-(3-phenyl-ureido)-propyl]-pyrazol-1-yl}-benzenesulfonamide),
o) compound 2326 (4-{3-[3-(3-Adamantan-1-yl-ureido)-propyl]-5-phenyl-pyrazol-1-yl}-benzenesulfonamide),
p) compound 2247 (4-{3-[3-(3-Cycloheptyl-ureido)-propyl]-5-phenyl-pyrazol-1-yl}-benzenesulfonamide),
q) compound 2327 (4-(3-{3-[3-(4-Chloro-phenyl)-ureido]-propyl}-5-phenyl-pyrazol-1-yl)-benzenesulfonamide), r) compound 2328 (4-(5-Phenyl-3-{3-[3-(4-trifluoromethyl-phenyl)-ureido]-propyl}-pyrazol-1-yl)-benzenesulfonamide); and
s) compound 2329 (4-(5-Phenyl-3-{3-[3-(4-trifluoromethoxy-phenyl)-ureido]-propyl}-pyrazol-1-yl)-benzenesulfonamide). In some embodiments, the sEHI comprises a dual inhibitor of phosphodiesterase 4 (PDE4) and sEH. In some embodiments, a dual inhibitor of sEH and PDE4 is administered as the sole active agent. In some embodiments, the dual inhibitor of PDE4 and sEH is a compound in Table 5 selected from the group consisting of:
a) compound 1; 3-(Cyclopentyloxy)-4-methoxy-N-(4-methoxy-2-(trifluoromethyl)benzyl)benzamide;
b) compound 2; 3-(Cyclopentyloxy)-4-methoxy-N-(2-(trifluoromethyl)benzyl)benzamide;
c) compound 3; 3-(Cyclopentyloxy)-4-methoxy-N-(2-methylbenzyl)benzamide;
d) compound 4; N-(4-Methoxy-2-(trifluoromethyl)benzyl) benzamide;
e) compound 5; 4-Fluoro-N-(4-methoxy-2-(trifluoromethyl) benzyl)benzamide;
f) compound 6; 3-Acetamido-N-(4-methoxy-2-(trifluoromethyl)benzyl)benzamide;
g) compound 7; N-(4-Methoxy-2-(trifluoromethyl)benzyl)-3-propionamidobenzamide;
h) compound 8; 3-Acetamido-N-(4-methoxy-2-(trifluoromethyl)benzyl)-4-methylbenzamide;
i) compound 9; N-(4-Methoxy-2-(trifluoromethyl)benzyl)-2-oxoindoline-6-carboxamide;
j) compound 10; 4-Acetamido-N-(4-methoxy-2-(trifluoromethyl)benzyl)benzamide;
k) compound 11; 4-Methoxy-N-(4-methoxy-2-(trifluoromethyl)benzyl)benzamide;
l) compound 14; 4-(Difluoromethoxy)-N-(4-methoxy-2-(trifluoromethyl)benzyl)benzamide;
m) compound 19; 3-(Cyclopentyloxy)-N-(4-methoxy-2-(trifluoromethyl)benzyl)benzamide;
n) compound 20; 3-(Cyclopentyloxy)-4-fluoro-N-(4-methoxy-2-(trifluoromethyl)benzyl)benzamide;
o) compound 21; tert-Butyl 4-((4-methoxy-2-(trifluoromethyl)benzyl)carbamoyl)piperidine-1-carboxylate;
p) compound 22; N-(4-Methoxy-2-(trifluoromethyl)benzyl) piperidine-4-carboxamide;
q) compound 23; N-(4-methoxy-2-(trifluoromethyl)benzyl)-1-propionylpiperidine-4-carboxamide (MPPA);
r) compound 24; 1-Butyryl-N-(4-methoxy-2-(trifluoromethyl)benzyl)piperidine-4-carboxamide;
s) compound 25; N-(4-Methoxy-2-(trifluoromethyl)benzyl)-1-(2-methylbutanoyl)piperidine-4-carboxamide;
t) compound 26; 1-Ethyl-N-(4-methoxy-2-(trifluoromethyl) benzyl)piperidine-4-carboxamide; and
u) compound 27; N-(4-Methoxy-2-(trifluoromethyl)benzyl)-1-propylpiperidine-4-carboxamide.

In some embodiments of the methods, the inhibitor of sEH (sEHI) is co-administered at a therapeutice or subtherapeutic dose with the sEHI-preconditioned stem cells. In some embodiments, the subject is a human. In some embodiments, the stem cells are selected from multipotent stem cells, pluripotent stem cells, and induced pluripotent stem cells. In some embodiments, the stem cells comprise mesenchymal stem cells. In some embodiments, the stem cells comprise myocyte stem cells. In some embodiments, the stem cells comprise cardiomyocyte stem cells. In some embodiments, the stem cells comprise adult cardiac stem cells or cardiac progenitor cells derived from human cardiac tissues. In some embodiments, the stem cells are selected from the group consisting of cardiomyocytes or cardiac progenitor cells derived from multipotent stem cells, cardiomyocytes or cardiac progenitor cells derived from pluripotent stem cells, cardiomyocytes or cardiac progenitor cells derived from induced pluripotent stem cells, adult cardiac progenitor cells and cardiac stem cells. In some embodiments, the stem cells are human induced pluripotent stem cells (hiPSCs)—derived cardiomyocytes (hiPSC-CMs). In some embodiments, the stem cells are human induced pluripotent stem cells (hiPSCs)—derived cardiac progenitor cells (hiPSC-CPCs). In some embodiments, the stem cells are transdifferentiated from dermal fibroblasts or cardiac fibroblasts. In some embodiments, the stem cells are syngeneic to the subject. In some embodiments, the stem cells are allogeneic to the subject. In some embodiments, the stem cells are xenogeneic to the subject. In some embodiments, at least about 1 million ($1\times10^6$) to about 1 billion ($1\times10^9$) stem cells are administered. In some embodiments, the stem cells are administered intravenously, intra-arterially or intralesionally. In some embodiments, the stem cells and the agent that increases the production and/or level of epoxy fatty acids (EpFA), or mimics thereof, are administered by the same route of administration. In some embodiments, the stem cells and the agent that increases the production and/or level of epoxy fatty acids (EpFA), or mimics thereof, are administered by different routes of administration. In some embodiments, the stem cells and the inhibitor of sEH are concurrently co-administered. In some embodiments, the stem cells and the inhibitor of sEH are sequentially co-administered. In some embodiments, the tissue is cardiac tissue.

In another aspect, provided are kits, stents and patches. In some embodiments, the kits, stents and patches comprise a population of stem cells preconditioned with one or more agents that increase the production and/or level of epoxy fatty acids (EpFA), or mimics thereof. In some embodiments, of the stents, the stent is a coronary artery stent. In some embodiments of the patches, the patch is a cardiac patch.

In some embodiments of the kits, stents and patches, the agent comprises one or more epoxy fatty acids (EpFA). In some embodiments, the epoxy fatty acids (EpFA) are selected from the group consisting of cis-epoxyeicosantrienoic acids ("EETs"), epoxides of linoleic acid, epoxides of eicosapentaenoic acid ("EPA"), epoxides of docosahexaenoic acid ("DHA"), epoxides of the arachidonic acid ("AA"), epoxides of cis-7,10,13,16,19-docosapentaenoic acid, and mixtures thereof. In some embodiments, the agent increases the production and/or levels of cis-epoxyeicosantrienoic acids ("EETs"). In some embodiments of the methods, the agent that increases the production and/or level of EETs is an inducing agent that increases EETs biosynthesis, e.g., omeprazole. In some embodiments of the kits, stents and patches, the agent that increases the production and/or level of EETs is an inhibitor of soluble epoxide hydrolase ("sEH"). In some embodiments, the inhibitor of sEH comprises a cyclohexyl moiety, aromatic moiety, substituted aromatic moiety or alkyl moiety attached to the pharmacophore. In some embodiments, the inhibitor of sEH comprises a cyclohexyl ether moiety attached to the pharmacophore. In some embodiments, the sEHI comprises a primary or central pharmacophore selected from the group consisting of a urea, a carbamate, and an amide, or these functionalities in a nitrogen heterocycle. In some embodiments, the sEHI comprises a primary or central pharmacophore that comprises a piperidin-4-yl urea. In some embodiments, the sEHI does not comprise 1-trifluoromethoxyphenyl-3-(1-propionylpiperidin-4-yl) urea (TPPU). In some embodiments, the sEHI is selected from the group consisting of 1-(3-fluoro-4-(trifluoromethoxy) phenyl)-3-(1-(tetrahydro-2H-pyran-4-carbo-nyl)piperidin-4-yl)urea (Compound 29 of Table 3) and 1-trifluoromethoxyphenyl-3-(1-propionylpiperidin-4-yl) urea (TPPU). In some embodiments, the sEHI does not comprise one or both of an adamantyl moiety or an azetidine moiety. In some embodiments, the inhibitor of sEH has an IC50 of less than about 100 IM. In some embodiments of the kits, stents and patches, the inhibitor of sEH is selected from the group consisting of:

a) 3-(4-chlorophenyl)-1-(3,4-dichlorphenyl)urea or 3,4,4'-trichlorocarbanilide (TCC; compound 295);
b) 12-(3-adamantan-1-yl-ureido) dodecanoic acid (AUDA; compound 700);
c) 1-adamantanyl-3-{5-[2-(2-ethoxyethoxy)ethoxy]pentyl}urea (AEPU; compound 950);
d) 1-(1-acetypiperidin-4-yl)-3-adamantanylurea (APAU; compound 1153);
e) trans-4-[4-(3-Adamantan-1-yl-ureido)-cyclohexyloxy]-benzoic acid (tAUCB; compound 1471);
f) cis-4-[4-(3-Adamantan-1-yl-ureido)-cyclohexyloxy]-benzoic acid (cAUCB; compound 1686);
g) 1-(1-methylsulfonyl-piperidin-4-yl)-3-(4-trifluoromethoxy-phenyl)-urea (TUPS; compound 1709);
h) trans-4-{4-[3-(4-Trifluoromethoxy-phenyl)-ureido]-cyclohexyloxy}-benzoic acid (tTUCB; compound 1728);
i) 1-trifluoromethoxyphenyl-3-(1-propionylpiperidin-4-yl) urea (TPPU; compound 1770);
j) 1-(1-ethylsulfonyl-piperidin-4-yl)-3-(4-trifluoromethoxy-phenyl)-urea (TUPSE; compound 2213);
k) 1-(1-(cyclopropanecarbonyl)piperidin-4-yl)-3-(4-(trifluoromethoxy)phenyl)urea (CPTU; compound 2214);
l) trans-N-methyl-4-[4-(3-Adamantan-1-yl-ureido)-cyclohexyloxy]-benzamide (tMAUCB; compound 2225);
m) trans-N-methyl-4-[4-((3-trifluoromethyl-4-chlorophenyl)-ureido)-cyclohexyloxy]-benzamide (tMTCUCB; compound 2226);
n) cis-N-methyl-4-{4-[3-(4-trifluoromethoxy-phenyl)-ureido]-cyclohexyloxy}-benzamide (cMTUCB; compound 2228);
o) 1-cycloheptyl-3-(3-(1,5-diphenyl-1H-pyrazol-3-yl)propyl)urea (HDP$_3$U; compound 2247);
p) trans-2-(4-(4-(3-(4-trifluoromethoxy-phenyl)-ureido)-cyclohexyloxy)-benzamido)-acetic acid (compound 2283);
q) N-(methylsulfonyl)-4-(trans-4-(3-(4-trifluoromethoxy-phenyl)-ureido)-cyclohexyloxy)-benzamide (compound 2728);
r) 1-(trans-4-(4-(1H-tetrazol-5-yl)-phenoxy)-cyclohexyl)-3-(4-(trifluoromethoxy)-phenyl)-urea (compound 2806);
s) 4-(trans-4-(3-(2-fluorophenyl)-ureido)-cyclohexyloxy)-benzoic acid (compound 2736);
t) 4-(4-(3-(4-(trifluoromethoxy)-phenyl)-ureido)-phenoxy)-benzoic acid (compound 2803);
u) 4-(3-fluoro-4-(3-(4-(trifluoromethoxy)phenyl)-ureido)-phenoxy)-benzoic acid (compound 2807);
v) N-hydroxy-4-(trans-4-(3-(4-(trifluoromethoxy)-phenyl)-ureido)-cyclohexyloxy)-benzamide (compound 2761);
w) (5-methyl-2-oxo-1,3-dioxol-4-yl)methyl 4-((1r,4r)-4-(3-(4-(trifluoromethoxy)-phenyl)-ureido)-cyclohexyloxy)-benzoate (compound 2796);
x) 1-(4-oxocyclohexyl)-3-(4-(trifluoromethoxy)-phenyl)-urea (compound 2809);
y) methyl 4-(4-(3-(4-(trifluoromethoxy)-phenyl)-ureido)-cyclohexylamino)-benzoate (compound 2804);
z) 1-(4-(pyrimidin-2-yloxy)-cyclohexyl)-3-(4-(trifluoromethoxy)-phenyl)-urea (compound 2810);
aa) 4-(trans-4-(3-(4-(difluoromethoxy)-phenyl)-ureido)-cyclohexyloxy)-benzoic acid (compound 2805);
bb) (1R,3S)—N-(4-cyano-2-(trifluoromethyl)benzyl)-3-((4-methyl-6-(methylamino)-1,3,5-triazin-2-yl)amino)cyclohexane-1-carboxamide (GSK2256294A);
cc) sorafenib (4-(4-(3-(4-chloro-3-4-[[4-chloro-3-(trifluoromethyl)phenyl]carbamoylamino]phenoxy]-N-methylpyridine-2-carboxamide);
dd) regorafenib (4-[4-[[4-chloro-3-(trifluoromethyl)phenyl]carbamoylamino]-3-fluorophenoxy]-N-methylpyridine-2-carboxamide);
ee) triclocarban (3-(4-chlorophenyl)-1-(3,4-dichlorphenyl) urea or 3,4,4-trichlorocarbanilide); and mixtures thereof. In some embodiments, the sEHI comprises a dual inhibitor of sEH and COX-2. In some embodiments, a dual inhibitor of sEH and COX-2 is administered as the sole active agent. In some embodiments, the dual inhibitor of sEH and COX-2 is 4-(5-phenyl-3-{3-[3-(4-trifluoromethyl-phenyl)-ureido]-propyl}-pyrazol-1-yl)-benzenesulfonamide (PTUPB). In some embodiments, the dual inhibitor of sEH and COX 2 is a compound in Table 4 selected from the group consisting of:

a) compound 1860 (1-Adamantan-1-yl-3-[1-(4-methanesulfonyl-phenyl)-5-phenyl-1H-pyrazol-3-ylmethyl]-urea),
b) compound 2321 (1-Cycloheptyl-3-[1-(4-methanesulfonyl-phenyl)-5-phenyl-1H-pyrazol-3-ylmethyl]-urea),
c) compound 2322 (1-[1-(4-Methanesulfonyl-phenyl)-5-phenyl-1H-pyrazol-3-ylmethyl]-3-phenyl-urea),
d) compound 2323 (1-[1-(4-Methanesulfonyl-phenyl)-5-phenyl-1H-pyrazol-3-ylmethyl]-3-(4-trifluoromethoxy-phenyl)-urea),
e) compound 2324 (1-[1-(4-Methanesulfonyl-phenyl)-5-phenyl-1H-pyrazol-3-ylmethyl]-3-(4-trifluoromethyl-phenyl)-urea),
f) compound 1861 (1-[1-(4-Methanesulfonyl-phenyl)-5-phenyl-1H-pyrazol-3-ylmethyl]-3-(3-trifluoromethyl-phenyl)-urea),
g) compound 2107 (4-{5-Phenyl-3-[3-(3-trifluoromethyl-phenyl)-ureidomethyl]-pyrazol-1-yl}-benzenesulfonamide),
h) compound 2106 (1-[5-tert-Butyl-1-(4-methanesulfonyl-phenyl)-1H-pyrazol-3-ylmethyl]-3-(3-trifluoromethyl-phenyl)-urea),
i) compound 2121 (4-{5-Phenyl-3-[3-(3-trifluoromethyl-phenyl)-ureido]-pyrazol-1-yl}-benzenesulfonamide),
j) compound 2313 (4-(5-Phenyl-3-{2-[3-(3-trifluoromethyl-phenyl)-ureido]-ethyl}-pyrazol-1-yl)-benzenesulfonamide),
compound 1862(1-{3-[1-(4-Methanesulfonyl-phenyl)-5-phenyl-1H-pyrazol-3-yl]-propyl}-3-(3-trifluoromethyl-phenyl)-urea),
k) compound 2246 (4-(5-Phenyl-3-{3-[3-(3-trifluoromethyl-phenyl)-ureido]-propyl}-pyrazol-1-yl)-benzenesulfonamide),
l) compound 2152 (4-(5-p-Tolyl-3-{3-[3-(3-trifluoromethyl-phenyl)-ureido]-propyl}-pyrazol-1-yl)-benzenesulfonamide),
m) compound 2325 (4-(3-{3-[3-(2,6-Diisopropyl-phenyl)-ureido]-propyl}-5-phenyl-pyrazol-1-yl)-benzenesulfonamide),
n) compound 2245 (4-{5-Phenyl-3-[3-(3-phenyl-ureido)-propyl]-pyrazol-1-yl}-benzenesulfonamide),
o) compound 2326 (4-{3-[3-(3-Adamantan-1-yl-ureido)-propyl]-5-phenyl-pyrazol-1-yl}-benzenesulfonamide), p) compound 2247 (4-{3-[3-(3-Cycloheptyl-ureido)-propyl]-5-phenyl-pyrazol-1-yl}-benzenesulfonamide),
q) compound 2327 (4-(3-{3-[3-(4-Chloro-phenyl)-ureido]-propyl}-5-phenyl-pyrazol-1-yl)-benzenesulfonamide),
r) compound 2328 (4-(5-Phenyl-3-{3-[3-(4-trifluoromethyl-phenyl)-ureido]-propyl}-pyrazol-1-yl)-benzenesulfonamide); and
s) compound 2329 (4-(5-Phenyl-3-{3-[3-(4-trifluoromethoxy-phenyl)-ureido]-propyl}-pyrazol-1-yl)-benzenesulfonamide). In some embodiments, the sEHI comprises a dual inhibitor of phosphodiesterase 4 (PDE4) and sEH. In some embodiments, a dual inhibitor of sEH and PDE4 is administered as the sole active agent. In some embodiments, the dual inhibitor of PDE4 and sEH is a compound in Table 5 selected from the group consisting of:

a) compound 1; 3-(Cyclopentyloxy)-4-methoxy-N-(4-methoxy-2-(trifluoromethyl)benzyl)benzamide;
b) compound 2; 3-(Cyclopentyloxy)-4-methoxy-N-(2-(trifluoromethyl)benzyl)benzamide;
c) compound 3; 3-(Cyclopentyloxy)-4-methoxy-N-(2-methylbenzyl)benzamide;
d) compound 4; N-(4-Methoxy-2-(trifluoromethyl)benzyl)benzamide;
e) compound 5; 4-Fluoro-N-(4-methoxy-2-(trifluoromethyl)benzyl)benzamide;
f) compound 6; 3-Acetamido-N-(4-methoxy-2-(trifluoromethyl)benzyl)benzamide;
g) compound 7; N-(4-Methoxy-2-(trifluoromethyl)benzyl)-3-propionamidobenzamide;
h) compound 8; 3-Acetamido-N-(4-methoxy-2-(trifluoromethyl)benzyl)-4-methylbenzamide;
i) compound 9; N-(4-Methoxy-2-(trifluoromethyl)benzyl)-2-oxoindoline-6-carboxamide;
j) compound 10; 4-Acetamido-N-(4-methoxy-2-(trifluoromethyl)benzyl)benzamide;
k) compound 11; 4-Methoxy-N-(4-methoxy-2-(trifluoromethyl)benzyl)benzamide;
l) compound 14; 4-(Difluoromethoxy)-N-(4-methoxy-2-(trifluoromethyl)benzyl)benzamide;
m) compound 19; 3-(Cyclopentyloxy)-N-(4-methoxy-2-(trifluoromethyl)benzyl)benzamide;
n) compound 20; 3-(Cyclopentyloxy)-4-fluoro-N-(4-methoxy-2-(trifluoromethyl)benzyl)benzamide;
o) compound 21; tert-Butyl 4-((4-methoxy-2-(trifluoromethyl)benzyl)carbamoyl)piperidine-1-carboxylate;
p) compound 22; N-(4-Methoxy-2-(trifluoromethyl)benzyl) piperidine-4-carboxamide;
q) compound 23; N-(4-methoxy-2-(trifluoromethyl)benzyl)-1-propionylpiperidine-4-carboxamide (MPPA);
r) compound 24; 1-Butyryl-N-(4-methoxy-2-(trifluoromethyl)benzyl)piperidine-4-carboxamide;
s) compound 25; N-(4-Methoxy-2-(trifluoromethyl)benzyl)-1-(2-methylbutanoyl)piperidine-4-carboxamide;
t) compound 26; 1-Ethyl-N-(4-methoxy-2-(trifluoromethyl) benzyl)piperidine-4-carboxamide; and
u) compound 27; N-(4-Methoxy-2-(trifluoromethyl)benzyl)-1-propylpiperidine-4-carboxamide.

In some embodiments of the kits, stents and patches, the stem cells are selected from multipotent stem cells, pluripotent stem cells, and induced pluripotent stem cells. In some embodiments, the stem cells comprise mesenchymal stem cells. In some embodiments, the stem cells comprise myocyte stem cells. In some embodiments, the stem cells comprise cardiomyocyte stem cells. In some embodiments, the stem cells are selected from the group consisting of cardiomyocytes or cardiac progenitor cells derived from multipotent stem cells, cardiomyocytes or cardiac progenitor cells derived from pluripotent stem cells, cardiomyocytes or cardiac progenitor cells derived from induced pluripotent stem cells, adult cardiac progenitor cells and cardiac stem cells. In some embodiments, the stem cells are human induced pluripotent stem cells (hiPSCs)—derived cardiomyocytes (hiPSC-CMs). In some embodiments, the stem cells are human induced pluripotent stem cells (hiPSCs)—derived cardiac progenitor cells (hiPSC-CPCs). In some embodiments, the stem cells are transdifferentiated from dermal fibroblasts or cardiac fibroblasts. In some embodiments, the population of stem cells comprises at least about 1 million ($1 \times 10^6$) to about 1 billion ($1 \times 10^9$) stem cells.

Definitions

Units, prefixes, and symbols are denoted in their Systeme International de Unites (SI) accepted form. Numeric ranges are inclusive of the numbers defining the range. Unless otherwise indicated, nucleic acids are written left to right in 5' to 3' orientation; amino acid sequences are written left to right in amino to carboxy orientation. The headings provided herein are not limitations of the various aspects or embodiments, which can be had by reference to the specification as a whole. Accordingly, the terms defined immediately below are more fully defined by reference to the specification in its entirety. Terms not defined herein have their ordinary meaning as understood by a person of skill in the art.

"cis-Epoxyeicosatrienoic acids" ("EETs") are biomediators synthesized by cytochrome P450 oxidase. As discussed further in a separate section below, while the use of unmodified EETs is the most preferred, derivatives of EETs, such as amides and esters (both natural and synthetic), EETs analogs, and EETs optical isomers and corresponding EPA and DHA derivatives, including omega-3-derived epoxides epoxyeicosatetraenoic acids (EEQs) and epoxydocosapentaenoic acids (EDPs), and their mimics, can all be used in the methods, both in pure form and as mixtures of these forms. For convenience of reference, the term "EETs" as used herein refers to all of these forms unless otherwise required by context.

"Epoxide hydrolases" ("EH;" EC 3.3.2.3) are enzymes in the alpha beta hydrolase fold family that add water to 3-membered cyclic ethers termed epoxides.

"Soluble epoxide hydrolase" ("sEH") is an epoxide hydrolase which in endothelial and muscle cells converts EETs to dihydroxy derivatives called dihydroxyeicosatrienoic acids ("DHETs"). The cloning and sequence of the murine sEH is set forth in Grant et al., J. Biol. Chem. 268(23):17628-17633 (1993). The cloning, sequence, and accession numbers of the human sEH sequence are set forth in Beetham et al., Arch. Biochem. Biophys. 305(1):197-201 (1993). The amino acid sequence of human sEH is SEQ ID NO.:1, while the nucleic acid sequence encoding the human sEH is SEQ ID NO.:2. (The sequence set forth as SEQ ID NO.:2 is the coding portion of the sequence set forth in the Beetham et al. 1993 paper and in the NCBI Entrez Nucleotide Browser at accession number L05779, which include the 5' untranslated region and the 3' untranslated region.) The evolution and nomenclature of the gene is discussed in Beetham et al., DNA Cell Biol. 14(1):61-71 (1995). Soluble epoxide hydrolase represents a single highly conserved gene product with over 90/a homology between rodent and human (Arand et al., FEBS Lett., 338:251-256 (1994)). Unless otherwise specified, as used herein, the terms "soluble epoxide hydrolase" and "sEH" refer to human sEH.

Unless otherwise specified, as used herein, the term "sEH inhibitor" (also abbreviated as "sEHI") refers to an inhibitor of human sEH. Preferably, the inhibitor does not also inhibit the activity of microsomal epoxide hydrolase by more than 25% at concentrations at which the inhibitor inhibits sEH by at least 50%, and more preferably does not inhibit mEH by more than 10% at that concentration. For convenience of reference, unless otherwise required by context, the term "sEH inhibitor" as used herein encompasses prodrugs which are metabolized to active inhibitors of sEH. Further for convenience of reference, and except as otherwise required by context, reference herein to a compound as an inhibitor of sEH includes reference to derivatives of that compound (such as an ester of that compound) that retain activity as an sEH inhibitor.

"Valvular heart disease" refers to a disorder of any one of the four valves of the heart. More particularly, it refers to conditions in which the disorder increases pressure in a chamber or chambers of the heart. For example, mitral valve insufficiency permits some blood to flow back from the left ventricle into the left atrium rather than into the aorta, increasing the pressure in the atrium.

"Fibrillation," as defined on the website of the American College of Cardiology, is an abnormal, uncontrolled rapid contraction of the fibers in the heart. It further states: "When the process involves the two upper chambers of the heart (the atria), the condition is called 'atrial fibrillation.' When it involves the lower, ventricular chambers, the condition is called 'ventricular fibrillation.'"

An "arrhythmia" is a disorder of the regular rhythmic beating of the heart. As used herein, the term refers to atrial or ventricular fibrillation.

"Arrhythmogenic right ventricular cardiomyopathy" or "ARVC" is a recently recognized form of cardiomyopathy in which electrical disturbances affect the functioning of the right ventricle more than the left ventricle. According to the website of the Cardiomyopathy Association, it is defined as a heart muscle disease characterized by the replacement of heart muscle by fibrous scar and fatty tissue, and has acquired several names, all of which denote the same condition. In addition to ARVC, the most common term, it has also been called Arrhythmogenic Right Ventricular Dysplasia/Cardiomyopathy (ARVD/C) and Arrhythmogenic Right Ventricular Dysplasia (ARVD). It is thought to affect between 1:3,000 and 1:10,000 people.

With respect to cardiac arrhythmias, "inhibiting" means that the recurrence of such arrhythmias are reduced or eliminated, the arrhythmias are terminated or that the duration of such arrhythmias is reduced, or both. With respect to cardiac hypertrophy or dilated cardiomyopathy, "inhibiting" means (i) the prevention of the development of the condition in a subject at risk thereof or (ii) in the case of a subject with cardiac hypertrophy, the reversal of hypertrophy.

By "physiological conditions" is meant an extracellular milieu having conditions (e.g., temperature, pH, and osmolarity) which allows for the sustenance or growth of a cell of interest.

"Micro-RNA" ("miRNA") refers to small, noncoding RNAs of 18-25 nt in length that negatively regulate their complementary mRNAs at the posttranscriptional level in many eukaryotic organisms. See, e.g., Kurihara and Watanabe, Proc Natl Acad Sci USA 101(34):12753-12758 (2004). Micro-RNA's were first discovered in the roundworm C. elegans in the early 1990s and are now known in many species, including humans. As used herein, it refers to exogenously administered miRNA unless specifically noted or otherwise required by context.

Cytochrome P450 ("CYP450") metabolism produces cis-epoxydocosapentaenoic acids ("EpDPEs") and cis-epoxyeicosatetraenoic acids ("EpETEs") from docosahexaenoic acid ("DHA") and eicosapentaenoic acid ("EPA"), respectively. These epoxides are known endothelium-derived hyperpolarizing factors ("EDHFs"). These EDHFs, and others yet unidentified, are mediators released from vascular endothelial cells in response to acetylcholine and bradykinin, and are distinct from the NOS- (nitric oxide) and COX-derived (prostacyclin) vasodilators. Overall cytochrome P450 (CYP450) metabolism of polyunsaturated fatty acids produces epoxides, such as EETs, which are prime candidates for the active mediator(s). 14(15)-EpETE, for example, is derived via epoxidation of the 14,15-double bond of EPA and is the ω-3 homolog of 14(15)-EpETrE ("14(15)EET") derived via epoxidation of the 14,15-double bond of arachidonic acid.

"$IC_{50}$" refers to the concentration of an agent required to inhibit enzyme activity by 50%.

By "physiological conditions" is meant an extracellular milieu having conditions (e.g., temperature, pH, and osmolarity) which allows for the sustenance or growth of a cell of interest.

"Micro-RNA" ("miRNA") refers to small, noncoding RNAs of 18-25 nt in length that negatively regulate their complementary mRNAs at the posttranscriptional level in many eukaryotic organisms. See, e.g., Kurihara and Watanabe, Proc Natl Acad Sci USA 101(34):12753-12758 (2004). Micro-RNA's were first discovered in the roundworm C. elegans in the early 1990s and are now known in many species, including humans. As used herein, it refers to exogenously administered miRNA unless specifically noted or otherwise required by context.

The term "therapeutically effective amount" refers to that amount of the compound being administered sufficient to prevent or decrease the development of one or more of the symptoms of the disease, condition or disorder being treated (e.g., fibrosis and/or inflammation).

The terms "prophylactically effective amount" and "amount that is effective to prevent" refer to that amount of drug that will prevent or reduce the risk of occurrence of the biological or medical event that is sought to be prevented. In many instances, the prophylactically effective amount is the same as the therapeutically effective amount.

"Subtherapeutic dose" refers to a dose of a pharmacologically active agent(s), either as an administered dose of pharmacologically active agent, or actual level of pharmacologically active agent in a subject that functionally is insufficient to elicit the intended pharmacological effect in itself (e.g., to obtain analgesic, anti-inflammatory, and/or anti-fibrotic effects), or that quantitatively is less than the established therapeutic dose for that particular pharmacological agent (e.g., as published in a reference consulted by a person of skill, for example, doses for a pharmacological agent published in the Physicians' Desk Reference, 71st Ed., 2017 (PDR Network), Thomson Healthcare or Brunton, et al., Goodman & Gilman's The Pharmacological Basis of Therapeutics, 12th edition, 2010, McGraw-Hill Professional). A "subtherapeutic dose" can be defined in relative terms (i.e., as a percentage amount (less than 100%) of the amount of pharmacologically active agent conventionally administered). For example, a subtherapeutic dose amount can be about 1% to about 75% of the amount of pharmacologically active agent conventionally administered. In some embodiments, a subtherapeutic dose can be about 75%, 50%, 30%, 25%, 20%, 10% or less, than the amount of pharmacologically active agent conventionally administered.

The terms "controlled release," "sustained release," "extended release," and "timed release" are intended to refer interchangeably to any drug-containing formulation in which release of the drug is not immediate, i.e., with a "controlled release" formulation, oral administration does not result in immediate release of the drug into an absorption pool. The terms are used interchangeably with "nonimmediate release" as defined in Remington: The Science and Practice of Pharmacy, University of the Sciences in Philadelphia, Eds., 21$^{st}$ Ed., Lippencott Williams & Wilkins (2005).

The terms "sustained release" and "extended release" are used in their conventional sense to refer to a drug formulation that provides for gradual release of a drug over an extended period of time, for example, 12 hours or more, and that preferably, although not necessarily, results in substantially steady-state blood levels of a drug over an extended time period.

As used herein, the term "delayed release" refers to a pharmaceutical preparation that passes through the stomach intact and dissolves in the small intestine.

As used herein, "synergy" or "synergistic" interchangeably refer to the combined effects of two active agents that are greater than their additive effects. Synergy can also be achieved by producing an efficacious effect with combined inefficacious doses of two active agents. The measure of synergy is independent of statistical significance.

The terms "systemic administration" and "systemically administered" refer to a method of administering agent (e.g., stem cells, an agent that increases epoxy fatty acids (EpFA) (e.g., an inhibitor of sEH, an EET, an epoxy fatty acid, and mixtures thereof), optionally with an anti-inflammatory agent and/or an analgesic agent) to a mammal so that the agent/cells is delivered to sites in the body, including the targeted site of pharmaceutical action, via the circulatory system. Systemic administration includes, but is not limited to, oral, intranasal, rectal and parenteral (i.e., other than through the alimentary tract, such as intramuscular, intravenous, intra-arterial, transdermal and subcutaneous) administration.

The term "co-administration" refers to the presence of both active agents/cells in the blood or body at the same time. Active agents that are co-administered can be delivered concurrently (i.e., at the same time) or sequentially.

The phrase "cause to be administered" refers to the actions taken by a medical professional (e.g., a physician), or a person controlling medical care of a subject, that control and/or permit the administration of the agent(s)/compound(s)/cell(s) at issue to the subject. Causing to be administered can involve diagnosis and/or determination of an appropriate therapeutic or prophylactic regimen, and/or prescribing particular agent(s)/compounds/cell(s) for a subject. Such prescribing can include, for example, drafting a prescription form, annotating a medical record, and the like.

The term "mesenchymal stem cells" refers to stem cells defined by their capacity to differentiate into bone, cartilage, and adipose tissue. With respect to cell surface markers, MSCs generally express CD44, CD90 and CD105, and do not express CD4, CD34, CD45, CD80, CD86 or MHC-II.

The terms "patient," "subject" or "individual" interchangeably refers to a mammal, e.g., a human, a non-human mammal, including primates (e.g., macaque, pan troglodyte, pongo), a domesticated mammal (e.g., felines, canines), an agricultural mammal (e.g., bovine, ovine, porcine, equine) and a laboratory mammal or rodent (e.g., rattus, murine, lagomorpha, hamster).

The term "mitigating" refers to reduction or elimination of one or more symptoms of that pathology or disease, and/or a reduction in the rate or delay of onset or severity of one or more symptoms of that pathology or disease, and/or the prevention of that pathology or disease.

The terms "inhibiting," "reducing," "decreasing" refers to inhibiting the fibrosis and/or inflammation in a non-human mammalian subject by a measurable amount using any method known in the art. For example, inflammation is inhibited, reduced or decreased if an indicator of inflammation, e.g., swelling, blood levels of prostaglandin PGE2, is at least about 10%, 20%, 30%, 50%, 80%, or 100% reduced, e.g., in comparison to the same inflammatory indicator prior to administration of an agent that increases epoxy fatty acids (EpFA) (e.g., an inhibitor of sEH, an EET, an epoxy fatty acid, and mixtures thereof). In some embodiments, the fibrosis and/or inflammation is inhibited, reduced or decreased by at least about 1-fold, 2-fold, 3-fold, 4-fold, or more in comparison to the fibrosis and/or inflammation prior to administration of the agent that increases epoxy fatty acids (EpFA) (e.g., an inhibitor of sEH, an EET, an epoxy fatty acid, and mixtures thereof). Indicators of fibrosis and/or inflammation can also be qualitative.

As used herein, the phrase "consisting essentially of" refers to the genera or species of active pharmaceutical agents included in a method or composition, as well as any excipients inactive for the intended purpose of the methods or compositions. In some embodiments, the phrase "consisting essentially of" expressly excludes the inclusion of one or more additional active agents other than the listed active agents, e.g., an agent that increases epoxy fatty acids (EpFA) (e.g., an inhibitor of sEH, an EET, an epoxy fatty acid, and mixtures thereof) and/or an anti-inflammatory agent.

BRIEF DESCRIPTION OF THE DRAWINGS

FIGS. 4A-C illustrate expression of firefly luciferase (Fluc) in hiPSC-CMs. (A) Representative examples of in vitro bioluminescence imaging of hiPSC-CMs transduced with a double fusion construct of reporter genes; firefly luciferase (Fluc) for bioluminescence imaging and enhanced green fluorescent protein (GFP). (B) Quantification of cell numbers based on bioluminescence signals. (C) A representative two-dimensional image of ultrasound-guided delivery of hiPSC-CMs into border zone of myocardial infarct. The needle and the left ventricular cavity are labelled in the image.

FIGS. 6A-1 illustrate that hemodynamic monitoring demonstrates an improvement in contractility with hiPSC-CMs and TPPU treatment: (A) Recording traces of left ventricular pressure, volume and derivative of pressure with respect to time (dP/dt) from Sham-operated, MI and MI+Cells+TPPU mice. (B) Pressure-Volume (P-V) loop analysis. Pressure and volume have been calibrated. The volume calibration was performed using cuvette (P/N 910-1049, Millar, Inc) filled with fresh heparinized 37° C. mouse blood. Summary data for End-systolic pressure (ESP, C), Maximum dP/dt (D), and Slope for the end-systolic P-V relationship (Ees, E). (F) Representative images from magnetic resonance imaging (MRI) in diastole (top panel) and systole (bottom panel) from Sham-operated, MI and MI+Cells+TPPU animals. (G-I) Summary data of left ventricular anterior wall (LVAW, d) (G), posterior wall thickness (LVPW,d) (H) during diastole and ejection fraction (EF %) (I) as assessed by MRI. Mean±SEM. n=5 per group. *P<0.05 by ANOVA. Cells=hiPSC-CMs.

DETAILED DESCRIPTION

1. Introduction

Figure 1:
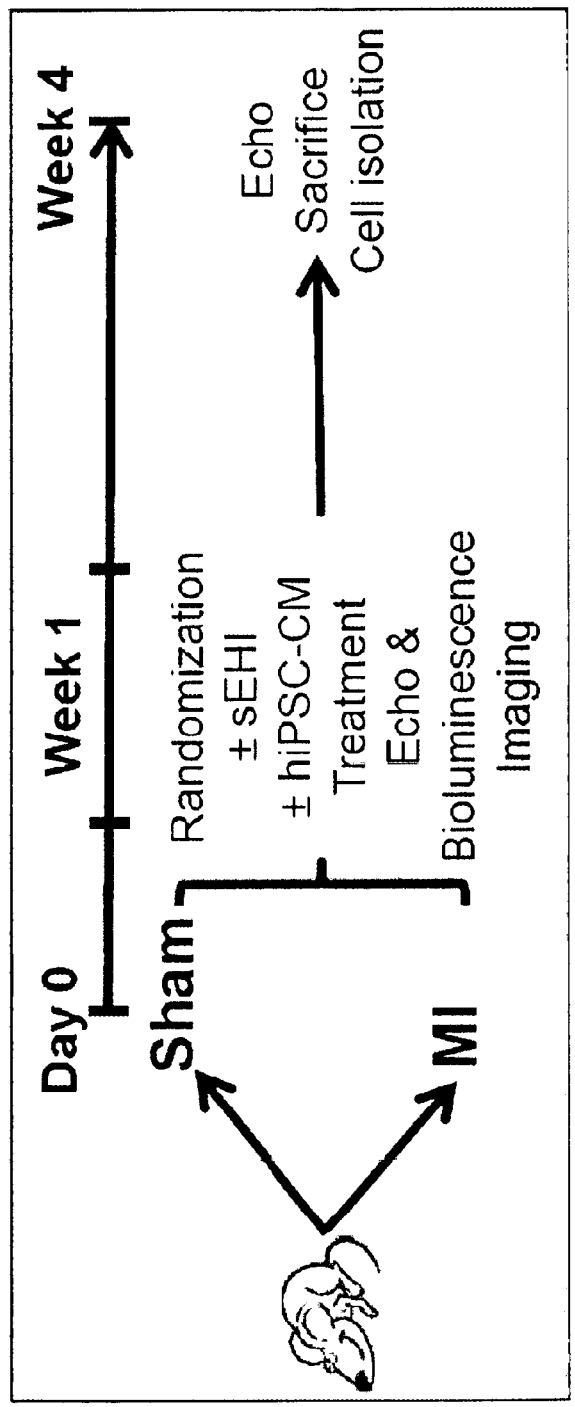
FIG. 1 illustrates a schematic of the treatment protocol in the in vivo animal model for treatment of myocardial infarction with sEHI-preconditioned stem cells in mice.

Heart failure is a life-threatening condition affecting millions of Americans. Indeed, once cardiac failure has developed, the condition is not reversible and only symptomatic treatment is available to ameliorate the symptoms. Cardiac cell-based therapy is currently undergoing extensive investigation as it can potentially replace cardiac transplantation which is the only available definitive therapy at this point in time.

We have previously discovered that inhibitors of soluble epoxide hydrolase can improve cardiac cell-based therapy and can potentially be offered to a large number of patients suffering from heart failure.

The present methods are based, in part, on the discovery that the survival and engraftment of stem cells (e.g., in cardiac tissue) can be increased by first exposing or conditioning the stem cells to an inhibitor of soluble epoxide hydrolase in vitro. In vitro drug-conditioning results in a significant reduction in stem cell apoptosis by reducing oxidative stress in the stem cells.

2. Conditions Subject to Treatment

The methods can facilitate, increase, improve and/or promote the survival, engraftment, and/or integration of transplanted stem cells in a tissue of an individual in need thereof, for any condition subject to treatment by administration of stem cells. For example, co-administration of stem cells with an agent that increases the production and/or level of cis-epoxyeicosantrienoic acids ("EETs") can facilitate, increase, improve and/or promote the survival, engraftment, and/or integration of transplanted stem cells to cardiac tissue, brain tissue, neurological tissue (e.g., central or peripheral), muscular tissue, bone tissue, renal tissue, skin, liver, pancreas, lung, inner ear, spinal cord, gingiva, or any other tissue that can be healed or repaired using stem cells.

In some embodiments, the subject has cardiomyopathy or cardiac arrhythmia. For example, the subject may have hypertrophic cardiomyopathy, e.g., due to valvular heart disease, familial hypertrophic cardiomyopathy, dilated cardiomyopathy, myocardial infarction, or secondary to administration of an anti-cancer drug or exposure to a toxic agent. Valvular heart disease can arise from any etiology, including, e.g., secondary to rheumatic fever, myxomatous degeneration of the valve, or papillary muscle dysfunction. In some embodiments, the subject has cardiac arrhythmia, e.g., due to atrial fibrillation, ventricular fibrillation, or ventricular tachycardia.

a. Cardiac Hypertrophy

Cardiomyocytes are terminally differentiated cells. In response to various extracellular stimuli, cardiomyocytes grow in a hypertrophic manner, an event that is characterized by enlargement of individual cell size, an increase in the content of contractile proteins such as myosin heavy chain, and expression of embryonic genes such as atrial natriuretic factor (ANF). (Chien et al., Faseb J.; 5:3037-46 (1991); Chien, Cardiologia.; 37:95-103 (1992); Chien, J Clin Invest.; 105:1339-42 (2000)) The collective result is cardiac hypertrophy, which is an adaptive and compensatory response in nature. The initial or compensated stage of hypertrophy normalizes wall stress per unit of myocardium and is thus a basic mechanism for maintaining normal chamber function. (Grossman et al, J Clin Invest.; 56:56-64 (1975)) However, this process is a double-edged sword: sustained cardiac hypertrophy will eventually lead to overt heart failure.

In most instances, heart failure is the final consequence of many underlying disease etiologies such as long-standing hypertension, coronary heart disease, valvular insufficiency, arrhythmia, viral myocarditis, and mutations in sarcomere-encoding genes. A compensatory enlargement of the myocardium, or hypertrophy, typically accompanies many of these predisposing insults and is a leading predictor for the development of more serious and life-threatening disease. Decompensated hypertrophy occurs if increased cardiac mass fails to normalize wall stress and the contractile function is not sufficient to maintain normal pump function. This is associated with clinical and pathological features of congestion.

Cardiac hypertrophy is characterized by an increase in heart-to-body weight ratio and an increase in the size of the individual cardiac myocytes, enhanced protein synthesis, and heightened organization of the sarcomere. Classically, two different hypertrophic phenotypes can be distinguished: (1) concentric hypertrophy due to pressure overload, which is characterized by parallel addition of sarcomeres and lateral growth of individual cardiomyocytes, and (2) eccentric hypertrophy due to volume overload or prior infarction, characterized by addition of sarcomeres in series and longitudinal cell growth. (Dorn et al., Circ Res.; 92:1171-5 (2003)). At the molecular level, these changes in cellular phenotype are accompanied by reinduction of the so-called fetal gene program, because patterns of gene expression mimic those seen during embryonic development. (Chien et al., Faseb J; 5:3037-46 (1991); Chien K R, Cardiologia.; 37:95-103 (1992)).

Hypertrophic transformation of the heart can be divided into three stages: (1) developing hypertrophy, in which load exceeds output, (2) compensatory hypertrophy, in which the workload/mass ratio is normalized and resting cardiac output is maintained, and (3) overt heart failure, with ventricular dilation and progressive declines in cardiac output despite continuous activation of the hypertrophic program. (Meerson F Z, Cor Vasa.; 3:161-77 (1961)). The late-phase "remodeling" process that leads to failure is associated with functional perturbations of cellular $Ca^{2+}$ homeostasis (Bers D M, Nature.; 415:198-205 (2002); Bers D M, Circ Res.; 90:14-7 (2002)) and ionic currents, (Ahmmed et al., Circ Res.; 86(5):558-70 (2000); Kaab et al., Circ Res.; 78:262-273 (1996); Kaab et al., Circulation.; 98:1383-93 (1998)) which contribute to an adverse prognosis by predisposing to ventricular dysfunction and malignant arrhythmia. Significant morphological changes include increased rates of apoptosis, (Haunstetter A and Izumo S, Circ Res.; 86:371-6 (2000)) fibrosis, and chamber dilation.

The dichotomy between adaptive and maladaptive hypertrophy has been appreciated for some time, and the mechanisms that determine how long-standing hypertrophy ultimately progresses to overt heart failure are in the process of being elucidated. One biochemical hallmark of left ventricular hypertrophy induced by pressure overload is a shift in myosin isoform from .alpha.- to .beta.-myosin heavy chains. (Delcayre C and Swynghedauw B, Pflugers Arch.; 355:39-47 (1975)). This alteration in myosin isoform expression result from transcriptionally mediated alteration in gene expression. (Boehler et al., J Biol. Chem.; 267:12979-12985 (1992)). Various lines of evidence suggest a decrease in the expression of the sarcoplasmic reticulum $Ca^{2+}$-cycling protein, $Ca^{2+}$ ATPase during the development of heart failure in several animal models, including humans with end-stage congestive heart failure, even though no changes can be detected during the compensated hypertrophied stage. (Kiss et al., Circ Res.; 77:759-764 (1995); Feldman et al., Circulation.; 75:331-9 (1987); Arai et al, Circ Res.; 72:463-469 (1993)). These changes are associated with a decrease in sarcoplasmic reticulum $Ca^{2+}$ transport. In addition, there are alterations in the level of phospholamban, sarcoplasmic reticulum $Ca^{2+}$-release channels and in $Ca^{2+}$ cycling proteins in the myofibrils and sarcolemma in different animal models with heart failure. (de la Bastie et al., Circ Res.; 66:554-564 (1990); Mercadier et al., J Clin Invest.; 85:305-309 (1990)). These studies suggest that critical components of the $Ca^{2+}$ cycling system may be responsible, in part, for the transitions between compensated pressure-overload hypertrophy and congestive heart failure.

Hypertrophy that occurs as a consequence of pressure overload is termed "compensatory" on the premise that it facilitates ejection performance by normalizing systolic wall stress. Recent experimental results, however, call into question the necessity of normalization of wall stress that results from hypertrophic growth of the heart. These findings, largely from studies in genetically engineered mice, raise the prospect of modulating hypertrophic growth of the myocardium to afford clinical benefit without provoking hemodynamic compromise. (Frey et al., supra, Dorn and Molkentin, supra; Frey et al., Circulation 109:1580-9 (2004)).

It is generally accepted that cardiac hypertrophy can be adaptive in some situations, for example, in athletes. However, it is less clear if a hypertrophic response to pathological situations, such as valvular heart disease, chronic arterial hypertension or a myocardial infarction, is initially a compensatory response and later becomes maladaptive or if this type of myocardial growth is detrimental from the outset.

It has been demonstrated that these different types of cardiac hypertrophy differ both at the morphological as well as the molecular level. Exercise-induced cardiac hypertrophy is generally not accompanied by an accumulation of collagen in the myocardium and usually does not exceed a modest increase in ventricular wall thickness. In addition, there are significantly differences in the expression levels for several hypertrophic genes, such as BNP or ET-1. Further, the isoform expression of $\alpha$-/$\beta$-MHCs is regulated in opposite directions in exercise versus pressure overload-induced cardiac hypertrophy. However, some hypertrophic pathways, such as calcincurin-dependent signaling, appear to be activated in both pathological and physiological exercise-induced hypertrophy, as demonstrated by the finding that the calcineurin inhibitor can attenuate both phenotypes. Taken together, these data indicate that exercise-associated (physiologic) versus pathologic hypertrophy differ at the molecular level, but this does not exclude the possibility that certain pathways may be involved in all phenotypes of cardiac hypertrophy.

Since adult cardiomyocytes are terminally differentiated cells, many of the same intracellular signaling pathways that regulate proliferation in cancer cells or immune cells instead regulate hypertrophic growth of cardiomyocytes. The hypertrophic growth can be initiated by endocrine, paracrine, and autocrine factors that stimulate a wide array of membrane-bound receptors. Their activation results in the triggering of multiple cytoplasmic signal transduction cascades, which ultimately affects nuclear factors and the regulation of gene expression. It has previously been documented that no single intracellular transduction cascade regulates cardiomyocyte hypertrophy in isolation, but instead each pathway operates as an integrated component between interdependent and cross-talking networks. Therefore, blockade of specific intracellular signaling pathways in the heart can dramatically affect the entire hypertrophic response and effectively decrease cardiac hypertrophy. Furthermore, specific activation of a number of discrete signal transduction pathways may be sufficient to activate the entire hypertrophic response through effects on other cross-talking signaling networks.

b. Valvular Heart Disease

The heart has four valves: the mitral valve (the only valve with two flaps), the tricuspid, with three differently sized flaps, the aortic valve, which opens to allow blood from the heart into the aorta, and the pulmonary valve. A number of disorders affecting the valves can result in increased pressure in the chambers of the heart, which in turn can result in cardiac hypertrophy. These conditions include mitral valve stenosis, mitral valve insufficiency, aortic valve insufficiency, aortic valve stenosis, and tricuspid valve insufficiency. Several of these conditions occur in persons who had undiagnosed or incompletely treated rheumatic fever as a child. Rheumatic fever occurs most often in children who have a streptococcal throat infection ("strep throat"), and can result in mitral stenosis, tricuspid stenosis, aortic insufficiency, aortic stenosis, multivalvular involvement or, less commonly, pulmonic stenosis. Unlike stenosis of blood vessels, which is typically caused by a build-up of lipids and cells on the interior of the vessel lumen, stenosis of heart valves is typically due to fusing of the flaps, to a build-up of calcium on the flap, causing it to harden, to a congenital deformity, a weakening of valve tissue ("myxomatous degeneration"), or use of certain medicines, such as fenfluramine and dexfenfluramine.

3. Preparation and Administration of Stem Cells

The administered stem cells will be appropriate to the tissue being targeted and treated or repaired. In some embodiments, the stem cells are multipotent or pluripotent, and can be isolated or induced. In some embodiments, the stem cells are mesenchymal stem cells, or stem cells derived or induced from the tissue of interest (e.g., muscle tissue, particularly cardiac muscle tissue, nerve tissue). In some embodiments, the stem cells are isolated, derived or induced from myocyte cells. In some embodiments, the stem cells are isolated, derived or induced from cardiomyocyte cells. In some embodiments, are isolated, derived or induced from cardiomyocytes or cardiac progenitor cells derived from multipotent stem cells, cardiomyocytes or cardiac progenitor cells derived from pluripotent stem cells, cardiomyocytes or cardiac progenitor cells derived from induced pluripotent stem cells, adult cardiac progenitor cells or cardiac stem cells. Isolation, derivation and/or production of cardiac progenitor cells (Sca-1+/CD31– cells) and cardiac stem cells is known in the art, as published in, e.g., Wang, et al., *PLoS One.* 2014 Jun. 11; 9(6):e95247; Pagliari, et al., *Front Physiol.* 2014 Jun. 3; 5:210; Beltrami, et al., *Cell.* 2003 Sep. 19; 114(6):763-76; Bolli, et al., *Lancet.* 2011 Nov. 26; 378(9806):1847-57; Chugh, et al., *Circulation.* 2012 Sep. 11; 126(11 Suppl 1):S54-64; Makkar, et al., *Lancet.* 2012 Mar. 10; 379(9819):895-904; Malliaras, et al., *J Am Coll Cardiol.* 2014 Jan. 21; 63(2):110-22; Delewi, *Heart.* 2013 February; 99(4):225-32; Clifford, et al., *Cochrane Database Syst Rev.* 2012 Feb. 15; 2:CD006536; Dan, et al., *Am J Stem Cells.* 2014 Mar. 13; 3(1):37-45; Wickham, et al., *J Biomed Mater Res B Appl Biomater.* 2014 Mar. 24; and other references cited herein.

a. Mesenchymal Stem Cells

In some embodiments, the stem cells are mesenchymal stem cells. The bone marrow and adipose tissue of an adult mammal is a repository of mesenchymal stem cells (MSCs). Bone marrow MSCs are self-renewing, clonal precursors of non-hematopoietic tissues. MSCs for use in the present methods can be isolated from a variety of tissues, including bone marrow, muscle, fat (i.e., adipose), liver, dermis, gingiva and periodontal ligament, using techniques known in the art. Depending on the stimulus and the culture conditions employed, these cells can form bone, cartilage, tendon/ligament, muscle, marrow, adipose, and other connective tissues.

In some embodiments, the MSCs are derived from adipose tissue. Adipose-derived MSCs (AdMSCs) can be obtained from either autologous (self) and allogeneic (non-self) sources. The use of allogeneic MSCs in patients is possible due to their low immunogenicity. However, autologous adMSCs are non-immunogeneic and considered to be safe in people and animals. AdMSCs can be administered either systematically (e.g., intravenous or intraarterially) or locally (e.g., directly to cardiac tissue, e.g., via the coronary artery) in the treatment of disorders. MSCs can be generated more efficiently and rapidly from adipose tissue than from bone marrow. Fat- or adipose-derived MSCs are present in higher number and have a significantly higher proliferation rate then bone-marrow derived MSCs.

Generally, the MSCs useful for administration express on their cell surface CD44, CD90 and CD105 and do not express on their cell surface CD4, CD34, CD45, CD80, CD86 or MHC-II. In various embodiments, the MSCs are adipose-derived mesenchymal stem cells (Ad-MSC). Ad-MSCs can be characterized by the surface expression of CD5, CD44, CD90 (Thy-1) and CD105; and by the non-expression of CD3, CD4, CD18, CD34, CD45, CD49d, CD80, CD86 and MHC class II. In other embodiments, the MSCs are derived from a non-adipose tissue, for example, bone marrow, liver, periodontal ligament, gingiva and/or dermal tissues. In some embodiments, the MSCs are non-hematopoietic stem cells derived from bone marrow (e.g., do not express CD34 or CD45). Cell surface markers of cardiac progenitor cells can include cKit, P-glycoprotein (a member of the multidrug resistance protein family), and Sca-1 (stem cell antigen 1), Sca-1-like, ISL LIM homeobox 1 (ISL1), and/or kinase insert domain receptor (a type II receptor tyrosine kinase) (KDR). See, e.g., Barile, et al., *Nat Clin Pract Cardiovasc Med.* 2007 February; 4 Suppl 1:S9-S14.

As appropriate, the MSCs can be autologous (i.e., from the same subject), syngeneic (i.e., from a subject having an identical or closely similar genetic makeup); allogeneic (i.e., from a subject of the same species) or xenogeneic to the subject (i.e., from a subject of a different species).

In various embodiments, the MSCs may be altered to enhance the viability of engrafted or transplanted cells. For example, the MSCs can be engineered to overexpress or to constitutively express Akt. See, e.g., U.S. Patent Publication No. 2011/0091430.

b. Preparation

Tissue comprising mesenchymal stem cells (MSCs) is obtained and processed. As appropriate the tissue can be adipose, bone marrow, periodontal ligament, gingiva, muscle, liver or dermis. The obtained MSCs can be autologous, syngeneic, allogeneic or xenogeneic to the subject mammal. The tissue is processed to isolate the MSCs such that they can be cultured in vitro. Solid tissues can be minced and digested with a proteinase (e.g., collagenase), as appropriate. In some embodiments, the isolated MSCs can be cultured in vitro for at least 1 passage, e.g., from about 2 passages to about 8 passages, e.g. for 2, 3, 4, 5, 6, 7, 8 passages, as appropriate. At least 24 hours prior to injection into the subject, e.g., 24, 36 or 48 hours prior to injection, the cultured MSCs are washed and then cultured in media comprising serum of the same species of the subject mammal (e.g., autologous, syngeneic and/or allogeneic serum) and in the absence of serum xenogeneic to the subject mammal to wash out serum proteins allogeneic to the subject mammal in order to avoid or minimize the risk of a potential transfusion reaction. For example, the present MSCs are substantially free of bovine and/or equine serum proteins prior to injection.

Prior to injection or engraftment into the subject mammal, the MSCs are rinsed and resuspended in a serum-free isotonic buffered solution (e.g., phosphate-buffered saline, 0.9% sodium chloride, lactated Ringer's solution (LRS), Hank's Balanced Salt Solution (HBSS), Earle's Balanced Salt Solution (EBSS), etc.).

In some embodiments, the MSCs administered to the subject are fresh (i.e., not frozen) and viable. In some embodiments, the MSCs have been cultured in vitro for one or more passages prior to injection, so the administered MSCs have never been frozen. The MSCs are evaluated for viability prior to administration. In some embodiments, the population of administered MSCs are at least about 50% viable, e.g., at least about 55%, 60%, 65%, 70%, 75%, 80%, 85%, 90%, 95%, 98%, 99%, 100% viable.

c. Preconditioning of Stem Cells

Prior to administration, the stem cells are exposed in vitro to an agent that increases the production and/or level of epoxy fatty acids (EpFA), or mimics thereof, under conditions and for a time sufficient to increase epoxy fatty acids (EpFA) and/or inhibit soluble epoxide hydrolase in the stem cells, thereby producing preconditioned stem cells Generally, the preconditioning or exposing step entails culturing the stem cells under normal culture conditions in the presence of the agent that increases the production and/or level of epoxy fatty acids (EpFA) (e.g., an inhibitor of sEH), or mimics thereof. In some embodiments, the stem cells are exposed in vitro to the agent at a concentration between about 0.1 nM to about 20 µM, e.g., at least about 0.1 nM to about 0.5 nM, 1 nM, 2 nM, 5 nM, 10 nM, 25 nM, 50 nM, 100 nM, 250 nM, 500 nM, 750 nM, 1 µM, 2 µM, 5 µM, 10 µM, or 20 µM. In some embodiments, the stem cells are exposed in vitro to the agent for a time period between about 0.5 days to about 10 days, e.g., at least about 0.5 day to about 1, 2, 3, 4, 5, 6, 7, 8, 9 or 10 days.

When using induced pluripotent stem cells, preconditioning of the stem cells can be performed before, concurrently with or after induction of the stem cells to promote differentiation to the desired tissue type, e.g., induction of differentiation into cardiomyocytes. In some embodiments, the stem cells are human induced pluripotent stem cells (hiPSCs)—derived cardiomyocytes (hiPSC-CMs), pluripotent stem cells (hiPSCs)—derived cardiac progenitor cells (hiPSC-CPCs) or cells transdifferentiated from dermal fibroblasts or cardiac fibroblasts.

d. Administration of Stem Cells

The stem cells can be administered by any appropriate route. In various embodiments, the stem cells are systemically administered, e.g., intravenously, intra-arterially, or administered directly to the tissue of interest for treatment or repair.

In some embodiments, the stem cells are administered locally, e.g., directly to cardiac tissue. As appropriate, the stem cells can be engrafted or transplanted into and/or around the tissue of interest, e.g., cardiac tissues. When engrafted or transplanted into and/or in the vicinity of one or more tissues of interest (e.g., cardiac tissues), the stem cells are administered within or within sufficient proximity of inflamed or damaged lesions in tissue to mitigate and/or reverse of damage and/or destruction of the tissue. For example, the stem cells are engrafted or transplanted into or within sufficient proximity to the tissue of interest to prevent, reduce or inhibit damage and/or destruction to the tissues.

As appropriate, injections of stem cells can be done after local anesthetics (e.g., lidocaine, bupivacaine) have been administered. It is also possible to inject the stem cells in conjunction with local anesthetics added to the cell suspension. Injections can also be made with the subject under general anesthesia with or without the use of local anesthetic agents (e.g., lidocaine).

In various embodiments, engraftment or transplantation of the stem cells can be facilitated using a matrix or caged depot. For example, the stem cells can be engrafted or transplanted in a "caged cell" delivery device wherein the cells are integrated into a biocompatible and/or biologically inert matrix (e.g. a hydrogel or other polymer or any device) that restricts cell movement while allowing the cells to remain viable. Synthetic extracellular matrix and other biocompatible vehicles for delivery, retention, growth, and differentiation of stem cells are known in the art and find use in the present methods. See, e.g., Prestwich, *J Control*

*Release.* 2011 Apr. 14, PMID 21513749; Perale, et al., *Int J Artif Organs.* (2011) 34(3):295-303; Suri, et al., *Tissue Eng Part A.* (2010) 16(5):1703-16; Khetan, et al., *J Vis Exp.* (2009) Oct. 26; (32). pii: 1590; Salinas, et al., *J Dent Res.* (2009) 88(8):681-92; Schmidt, et al., *J Biomed Mater Res A.* (2008) 87(4):1113-22 and Xin, et al., *Biomaterials* (2007) 28:316-325.

As appropriate or desired, the engrafted or transplanted stem cells can be modified to facilitate retention of the stem cells at the region of interest or the region of delivery. In other embodiments, the region of interest for engraftment or transplantation of the cells is modified in order to facilitate retention of the stem cells at the region of interest or the region of delivery. In one embodiment, this can be accomplished by introducing stromal cell derived factor-1 (SDF-1) into the region of interest, e.g., using a linkage chemistry or integrated biodegradable matrix (e.g., Poly(D,L-lactide-co-glycolide (PLGA) beads) that would provide a tunable temporal presence of the desired ligand up to several weeks. Stem cells bind to the immobilized SDF-1, thereby facilitating the retention of stem cells that are delivered to the region of interest for engraftment or transplantation. In other embodiments, integrating cyclic arginine-glycine-aspartic acid peptide into the region of interest can facilitate increased stem cell binding and retention at the region of interest for engraftment or transplantation. See, e.g., Ratliff, et al., *Am J Pathol.* (2010) 177(2):873-83.

In some embodiments, at least about 1 million stem cells/kg subject are administered or engrafted, e.g., at least about 2 million, 2.5 million, 3 million, 3.5 million, 4 million, 5 million, 6 million, 7 million, 8 million, 9 million or 10 million stem cells/kg subject are administered. In some embodiments, about 1 million to about 10 million stem cells/kg subject, e.g., about 2 million to about 8 million stem cells/kg are administered or grafted.

In some embodiments, at least about 5 million stem cells are administered or engrafted, e.g., at least about 10 million, 15 million, 20 million, 25 million, 30 million, 35 million, 40 million, 45 million, 50 million, 55 million, 60 million, 65 million, 70 million, 75 million, 80 million, 85 million, 90 million, 95 million or 100 million stem cells are administered or engrafted. In some embodiments, about 5 million to about 100 million stem cells are administered or engrafted, e.g., about 10 million to about 80 million stem cells are administered or engrafted. In some embodiments, at least about 50 million stem cells are administered or engrafted, e.g., at least about 100 million, 150 million, 200 million, 250 million, 300 million, 350 million, 400 million, 450 million, 500 million, 550 million, 600 million, 650 million, 700 million, 750 million, 800 million, 850 million, 900 million, 950 million or 1 billion stem cells are administered or engrafted.

In some embodiments, the stem cells are administered, e.g., intravenously, at a rate of about 1 million to about 10 million cells per minute, e.g., at a rate of about 2 million to about 4 million cells per minute, e.g., at a rate of about 2.5 million to about 3.5 million cells per minute.

A regime of treatment or prevention may involve one or multiple injections. For example, stem cells may be administered to the subject 1, 2, 3, 4, 5, 6, 7, 8, 9, 10, or more times, as appropriate. Subsequent administrations of stem cells may be administered systemically or locally. If administered locally, multiple injections of stem cells may be administered to the same or different locations. Multiple injections of stem cells can be administered daily, weekly, bi-weekly, monthly, bi-monthly, every 3, 4, 5, or 6 months, or annually, or more or less often, as needed by the subject. The frequency of administration of the stem cells can change over a course of treatment, e.g., depending on how well the engrafted or transplanted stem cells establish themselves at the site of administration and the responsiveness of the subject. The stem cells may be administered multiple times over a regime course of several weeks, several months, several years, or for the remainder of the life of the subject, as needed or appropriate.

The total amount of cells that are envisioned for use depend upon the desired effect, patient state, and the like, and may be determined by one skilled within the art. Dosages for any one patient depends upon many factors, including the patient's species, size, body surface area, age, the particular stem cells to be administered, sex, scheduling and route of administration, general health, and other drugs being administered concurrently.

4. Agents that Increase the Production and/or Level of Epoxy Fatty Acids (EpFA)

Agents that increase epoxy-fatty acids include epoxy-fatty acids (e.g., including EETs), and inhibitors of soluble epoxide hydrolase (sEH).

a. Inhibitors of Soluble Epoxide Hydrolase (sEH)

Scores of sEH inhibitors are known, of a variety of chemical structures. Derivatives in which the urea, carbamate or amide pharmacophore are particularly useful as sEH inhibitors. As used herein, "pharmacophore" refers to the section of the structure of a ligand that binds to the sEH. Derivatives that are metabolically stable are of use, as they are expected to have greater activity in vivo. Selective and competitive inhibition of sEH in vitro by a variety of urea, carbamate, and amide derivatives is taught, for example, by Morisseau et al., Proc. Natl. Acad. Sci. U.S.A, 96:8849-8854 (1999).

Derivatives of urea are transition state mimetics that form a group of sEH inhibitors. Within this group, N, N'-dodecyl-cyclohexyl urea (DCU), is an inhibitor, while N-cyclohexyl-N'-dodecylurea (CDU) is a particular embodiment. Some compounds, such as dicyclohexylcarbodiimide (a lipophilic diimide), can decompose to an active urea inhibitor such as DCU. Any particular urea derivative or other compound can be easily tested for its ability to inhibit sEH by standard assays, such as those discussed herein. The production and testing of urea and carbamate derivatives as sEH inhibitors is set forth in detail in, for example, Morisseau et al., Proc Natl Acad Sci (USA) 96:8849-8854 (1999).

N-Adamantyl-N'-dodecyl urea ("ADU") is both metabolically stable and has particularly high activity on sEH. Both the 1- and the 2-adamantyl ureas have been tested and have about the same high activity as an inhibitor of sEH. Adamantyl ureas of use include, e.g., 12-(3-Adamantan-1-yl-ureido)dodecanoic acid (AUDA), 12-(3-Adamantan-1-yl-ureido)dodecanoic acid butyl ester (AUDA-BE), and Adamantan-1-yl-3-{5-[2-(2-ethoxyethoxy)ethoxy]pentyl}urea (AEPU).

Another group of inhibitors are piperidines. The following Tables sets forth some exemplar inhibitors of sEH and their ability to inhibit sEH activity of the human enzyme and sEH from equine, ovine, porcine, feline and canine, expressed as the amount needed to reduce the activity of the enzyme by 50% (expressed as "$IC_{50}$").

TABLE 1

IC$_{50}$ values for selected alkylpiperidine-based sEH inhibitors against human sEH

| R: | | n = 0 | | n = 1 | |
|---|---|---|---|---|---|
| | | Compound | IC$_{50}$ (μM)$^a$ | Compound | IC$_{50}$ (μM)$^a$ |
| | H | I | 0.30 | II | 4.2 |
| | ethyl | 3a | 3.8 | 4a | 3.9 |
| | propyl | 3b | 0.81 | 4b | 2.6 |
| | butyl | 3c | 1.2 | 4c | 0.61 |
| | benzyl | 3d | 0.01 | 4d | 0.11 |

$^a$As determined via a kinetic fluorescent assay.

TABLE 2 sEH inhibitors

| Structure | Name | sEHi # |
|---|---|---|
| 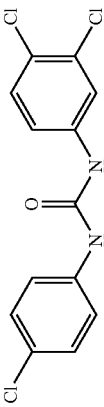 | 3-(4-chlorophenyl)-1-(3,4-dichlorphenyl)urea or 3,4,4'-trichlorocarbanilide | 295 (TCC) |
| 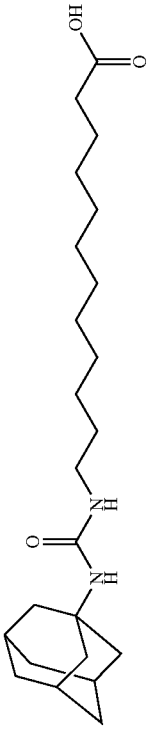 | 12-(3-adamantan-1-yl-ureido) dodecanoic acid | 700 (AUDA) |
| 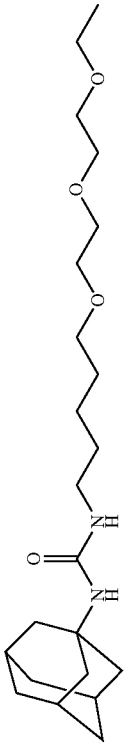 | 1-adamantanyl-3-{5-[2-(2-ethoxyethoxy)ethoxy]pentyl]}urea | 950 (AEPU) |
| 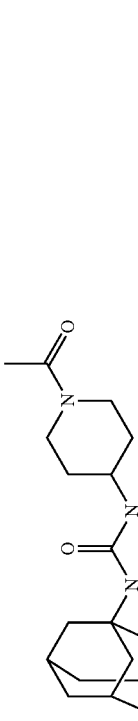 | 1-(1-acetypiperidin-4-yl)-3-adamantanylurea | 1153 (APAU) |
| 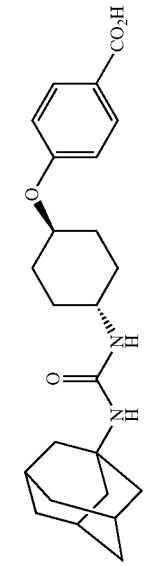 | trans-4-[4-(3-Adamantan-1-yl-ureido)-cyclohexyloxy]-benzoic acid | 1471 (tAUCB) |
| 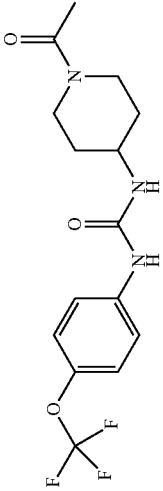 | 1-trifluoromethoxyphenyl-3-(1-acetylpiperidin-4-yl) urea | 1555 (TPAU) |

TABLE 2-continued sEH inhibitors

| Structure | Name | sEHi # |
|---|---|---|
| 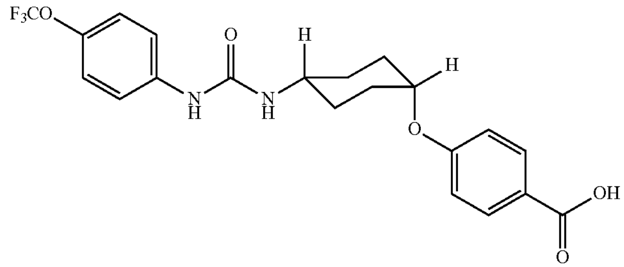 [SMILES: O=C(Nc1ccc(OC(F)(F)F)cc1)NC1CCC(Oc2ccc(C(=O)O)cc2)CC1] | cis-4-[4-(3-Adamantan-1-yl-ureido)-cyclohexyloxy]-benzoic acid | 1686 (cAUCB) |
| 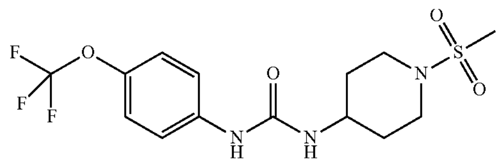 [SMILES: CS(=O)(=O)N1CCC(NC(=O)Nc2ccc(OC(F)(F)F)cc2)CC1] | 1-(1-methylsulfonyl-piperidin-4-yl)-3-(4-trifluoromethoxy-phenyl)-urea | 1709 (TUPS) |
| 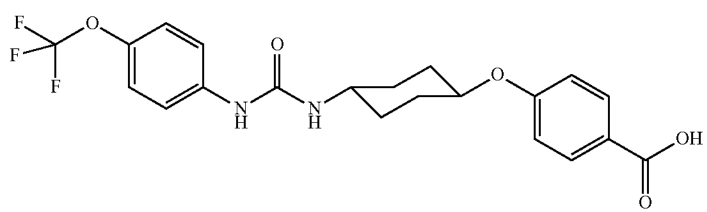 [SMILES: O=C(Nc1ccc(OC(F)(F)F)cc1)NC1CCC(Oc2ccc(C(=O)O)cc2)CC1] | trans-4-{4-[3-(4-Trifluoromethoxy-phenyl)-ureido]-cyclohexyloxy}-benzoic acid | 1728 (tTUCB) |
| 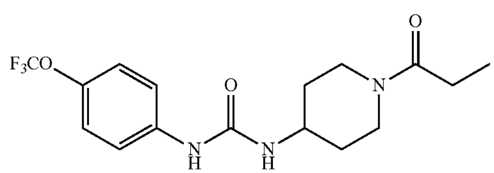 [SMILES: CCC(=O)N1CCC(NC(=O)Nc2ccc(OC(F)(F)F)cc2)CC1] | 1-trifluoromethoxyphenyl-3-(1-propionylpiperidin-4-yl) urea | 1770 (TPPU) |
| 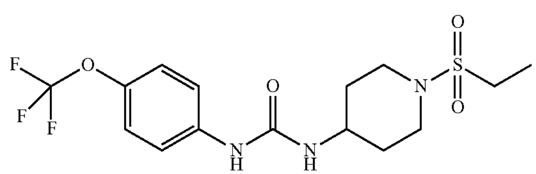 [SMILES: CCS(=O)(=O)N1CCC(NC(=O)Nc2ccc(OC(F)(F)F)cc2)CC1] | 1-(1-ethylsulfonyl-piperidin-4-yl)-3-(4-trifluoromethoxy-phenyl)-urea | 2213 (TUPSE) |

TABLE 2-continued sEH inhibitors

| Structure | Name | sEHi # |
|---|---|---|
| 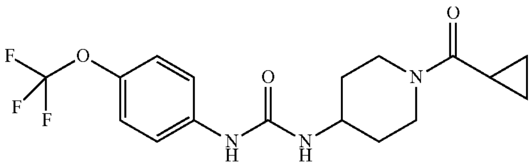 [SMILES: O=C(Nc1ccc(OC(F)(F)F)cc1)NC1CCN(C(=O)C2CC2)CC1] | 1-(1-(cyclopropanecarbonyl)piperidin-4-yl)-3-(4-(trifluoromethoxy)phenyl)urea | 2214 (CPTU) |
| 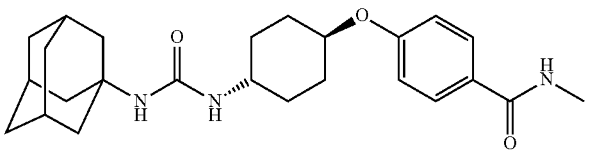 | trans-N-methyl-4-[4-(3-Adamantan-1-yl-ureido)-cyclohexyloxy]-benzamide | 2225 (tMAUCB) |
| 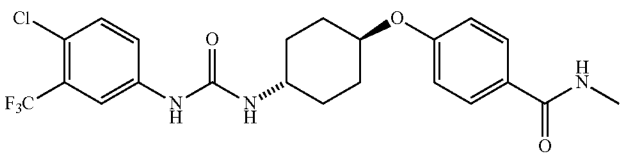 | trans-N-methyl-4-[4-((3-trifluoromethyl-4-chlorophenyl)-ureido)-cyclohexyloxy]-benzamide | 2226 (tMTCUCB) |
| 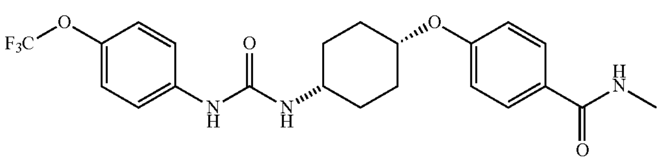 | cis-N-methyl-4-{4-[3-(4-trifluoromethoxy-phenyl)-ureido]-cyclohexyloxy}-benzamide | 2228 (cMTUCB) |
| 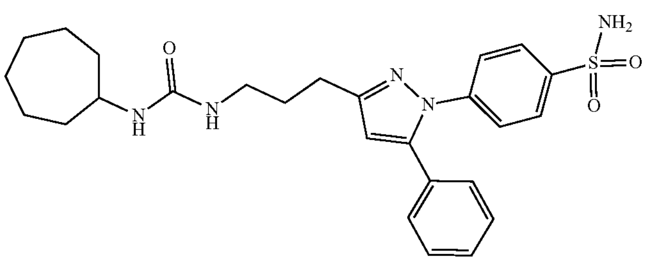 [SMILES: NS(=O)(=O)c1ccc(-n2nc(CCCNC(=O)NC3CCCCCC3)cc2-c2ccccc2)cc1] | 1-cycloheptyl-3-(3-(1,5-diphenyl-1H-pyrazol-3-yl)propyl)urea | 2247 (HDP3U) |

A number of other sEH inhibitors which can be used in the methods and compositions are described in published International Application Nos PCT/US2015/023048, PCT/US2013/024396, PCT/US2012/025074, PCT/US2011/064474, PCT/US2011/022901, PCT; US2008/072199, PCT/US2007/006412, PCT/US2005/038282, PCT/US2005/08765, PCT/US2004/010298; U.S. Published Patent Application Publication Nos: 2016/0200683, 2015/0011586, 2014/0088156, 2014/0038923, 2013/0274476, 2013/0143925, 2013/0137726, 2011/0098322, 2005/0026844, and U.S. Pat. No. 9,850,207 each of which is hereby incorporated herein by reference in its entirety for all purposes.

Additional piperidine inhibitors of sEH that find use in the present methods are described in U.S. Pat. No. 9,850,207 and WO 2015/148954. Piperidine compounds of interest are provided in Table 3. In some embodiments, the inhibitor of sEH is a piperidine compound from Table 3 selected from the group consisting of 1-(3-fluoro-4-(trifluoromethoxy)phenyl)-3-(1-isobutyrylpiperidin-4-yl)urea (Compound 19); 1-(1-(tetrahydro-2H-pyran-4-carbonyl)piperidin-4-yl)-3-(4-(trifluorometho-xy)phenyl)urea (Compound 1); 1-(1-(cyclopropanecarbonyl)piperidin-4-yl)-3-(3-fluoro-4-(trifluoromethox-y)phenyl)urea (Compound 24); (S)-1-(3-fluoro-4-(trifluoromethoxy)phenyl)-3-(1-(2-methylbutanoyl)piperidin-4-yl)urea (Compound 26); and 1-(3-fluoro-4-(trifluoromethoxy)phenyl)-3-(1-(tetrahydro-2H-pyran-4-carbo-nyl)piperidin-4-yl)urea (Compound 29). Compound 29 has been demonstrated to cross the blood-brain barrier in a Pentylenetetrazol (PTZ) Induced Seizure Model (See, Example 52 and FIG. 7 of WO 2015/148954).

A further inhibitor of soluble epoxide hydrolase useful in the present methods is GSK2256294A (IUPAC/Chemical Name: (1R,3S)—N-(4-cyano-2-(trifluoromethyl)benzyl)-3-((4-methyl-6-(methylamino)-1,3,5-triazin-2-yl)amino)cyclohexane-1-carboxamide; CAS #: 1142090-23-0), described in Podolin, et al., Prostaglandins Other Lipid Medial. (2013) 104-105:25-31, the structure of which is provided below:

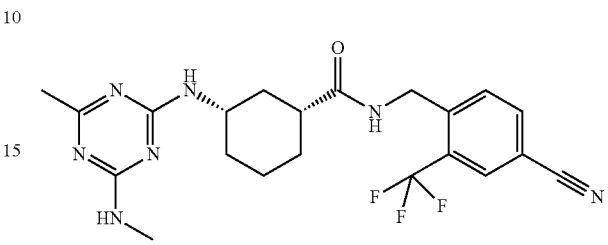

U.S. Pat. No. 5,955,496 (the '496 patent) also sets forth a number of sEH inhibitors which can be used in the methods. One category of these inhibitors comprises inhibitors that mimic the substrate for the enzyme. The lipid alkoxides (e.g., the 9-methoxide of stearic acid) are an exemplar of this group of inhibitors. In addition to the inhibitors discussed in the '496 patent, a dozen or more lipid alkoxides have been tested as sEH inhibitors, including the methyl, ethyl, and propyl alkoxides of oleic acid (also known as stearic acid alkoxides), linoleic acid, and arachidonic acid, and all have been found to act as inhibitors of sEH.

TABLE 3

| POTENT PIPERIDINE INHIBITORS OF SHE | | | | | |
|---|---|---|---|---|---|
| Structure and Compound No. | Mol. Weight | Exp. logP$^a$ | Cal. logP$^b$ | Ki (nM) (human sEH) | $t_{1/2}$ (min) (human sEH) |
| Compound 1 | 415.11 | 3.26 | 0.6 | 1.43 ± 0.01 | 14 |
| Compound 2 | 396.14 | 3.34 | 1.8 | 0.64 ± 0.17 | 15 |
| Compound 3 | 397.12 | 3.63 | 2.0 | 0.33 ± 0.34 | 17 |

TABLE 3-continued
POTENT PIPERIDINE INHIBITORS OF sEH
| Structure and Compound No. | Mol. Weight | Exp. logP[a] | Cal. logP[b] | Ki (nM) (human sEH) | t$_{1/2}$ (min) (human sEH) |
|---|---|---|---|---|---|
| 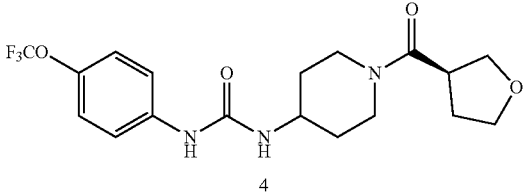 [SMILES: O=C(Nc1ccc(OC(F)(F)F)cc1)NC1CCN(C(=O)[C@@H]2CCOC2)CC1] 4 | 401.16 | 3.38 | 1.4 | 1.41 ± 0.11 | 17 |
| 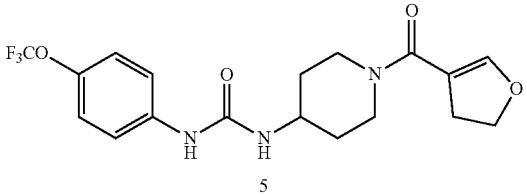 [SMILES: O=C(Nc1ccc(OC(F)(F)F)cc1)NC1CCN(C(=O)C2=COCC2)CC1] 5 | 399.14 | 3.49 | 2.6 | 0.77 ± 0.02 | 13 |
| 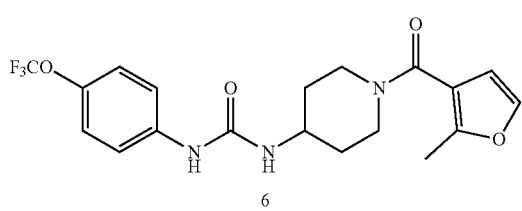 [SMILES: Cc1occc1C(=O)N1CCC(NC(=O)Nc2ccc(OC(F)(F)F)cc2)CC1] 6 | 411.14 | 4.30 | 2.5 | 0.55 ± 0.06 | 15 |
| 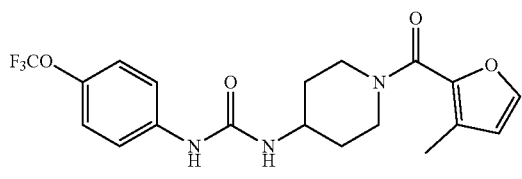 [SMILES: Cc1ccoc1C(=O)N1CCC(NC(=O)Nc2ccc(OC(F)(F)F)cc2)CC1] 7 | 411.14 | 4.48 | 2.5 | 0.26 ± 0.11 | 21 |
| 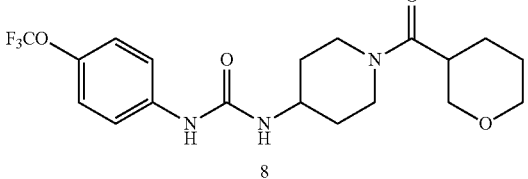 8 | 415.17 | 3.42 | 1.8 | 1.99 ± 0.23 | 13 |
| 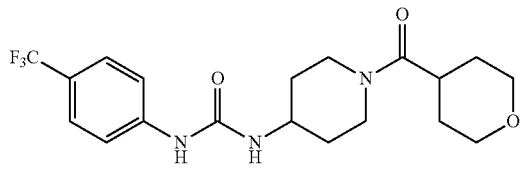 9 | 399.18 | 3.16 | 0.8 | 1.73 ± 0.01 | 11 |
| 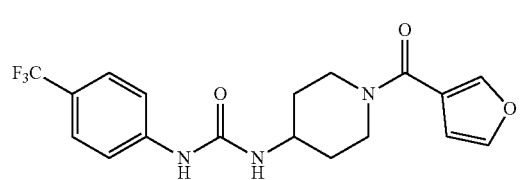 10 | 381.13 | 3.50 | 1.6 | 1.21 ± 0.2 | 11 |

TABLE 3-continued

POTENT PIPERIDINE INHIBITORS OF sEH

| Structure and Compound No. | Mol. Weight | Exp. logP[a] | Cal. logP[b] | Ki (nM) (human sEH) | $t_{1/2}$ (min) (human sEH) |
|---|---|---|---|---|---|
| 11 | 385.16 | 3.27 | 2.2 | 1.19 ± 0.08 | 13 |
| 12 | 383.15 | 3.37 | 2.8 | 1.03 ± 0.20 | 8 |
| 13 | 395.15 | 4.19 | 2.7 | 0.51 ± 0.03 | 11 |
| 14 | 395.15 | 4.29 | 2.7 | 0.22 ± 0.01 | 15 |
| 15 | 399.18 | 3.41 | 2.0 | 2.40 ± 0.08 | 11 |
| 16 | 380.15 | 3.26 | 2.0 | 0.50 ± 0.01 | 10 |
| 17 | 401.16 | 3.22 | 1.4 | 1.70 ± 0.01 | 12 |

TABLE 3-continued
POTENT PIPERIDINE INHIBITORS OF SHE
| Structure and Compound No. | Mol. Weight | Exp. logP[a] | Cal. logP[b] | Ki (nM) (human sEH) | $t_{1/2}$ (min) (human sEH) |
|---|---|---|---|---|---|
| 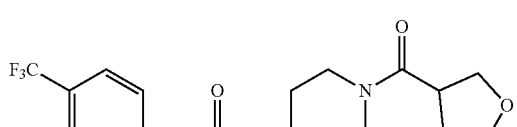 18 | 385.16 | 3.16 | 1.6 | 1.74 ± 0.11 | 10 |
| 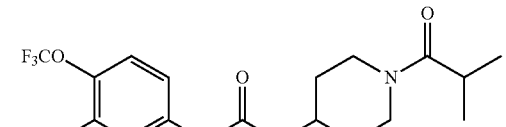 19 | 391.15 | 4.73 | 2.0 | 0.31 ± 0.01 | 22 |
| 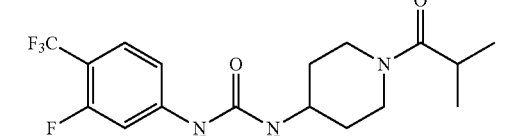 20 | 375.16 | 4.40 | 2.3 | 0.49 ± 0.4 | 12 |
| 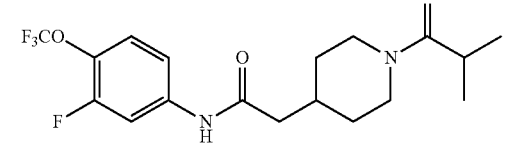 21 | 390.38 | 5.81 | 2.6 | 4.72 ± 0.70 | 3.4 |
| 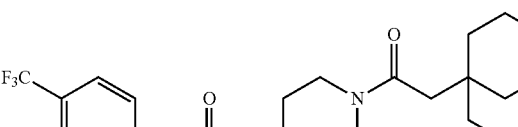 22 | 469.22 | — | — | 10.2 ± 1.1 | — |
| 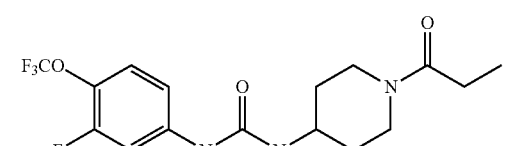 23 | 377.34 | 4.00 | 1.7 | 0.87 ± 0.13 | 11 |

TABLE 3-continued
POTENT PIPERIDINE INHIBITORS OF SHE
| Structure and Compound No. | Mol. Weight | Exp. logP[a] | Cal. logP[b] | Ki (nM) (human sEH) | $t_{1/2}$ (min) (human sEH) |
|---|---|---|---|---|---|
| 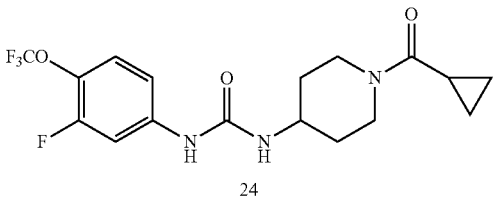 [SMILES: O=C(Nc1ccc(OC(F)(F)F)c(F)c1)NC1CCN(C(=O)C2CC2)CC1] 24 | 389.35 | 4.19 | 1.7 | 0.15 ± 0.04 | 19 |
| 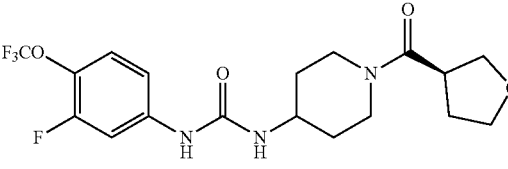 25 | 419.38 | 3.59 | 1.6 | 0.70 ± 0.01 | 13 |
| 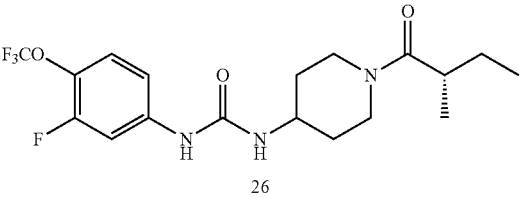 [SMILES: CC[C@H](C)C(=O)N1CCC(NC(=O)Nc2ccc(OC(F)(F)F)c(F)c2)CC1] 26 | 405.39 | 4.16 | 2.5 | <0.05 | 22 |
| 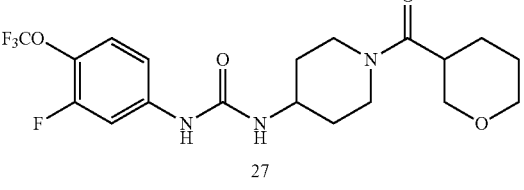 27 | 433.40 | 4.09 | 2.0 | 0.78 ± 0.19 | 12 |
| 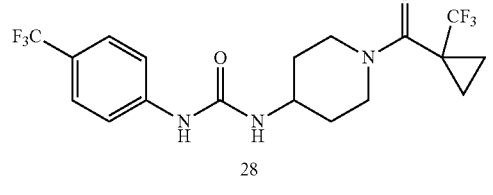 28 | 439.36 | 4.63 | 2.0 | 0.05 ± 0.04 | 24 |
| 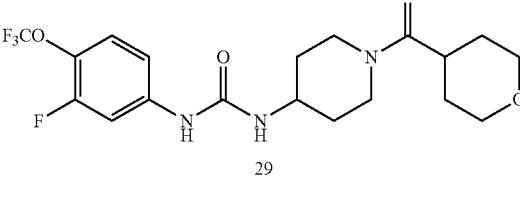 29 | 433.4 | 3.73 | 0.8 | 0.75 ± 0.05 | 11 |
| 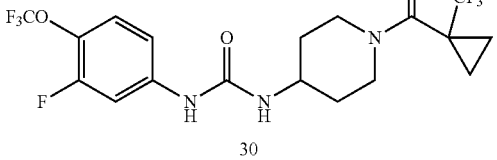 30 | 457.35 | 5.94 | 2.0 | <0.05 | 18 |

TABLE 3-continued
POTENT PIPERIDINE INHIBITORS OF SHE
| Structure and Compound No. | Mol. Weight | Exp. logP[a] | Cal. logP[b] | Ki (nM) (human sEH) | t$_{1/2}$ (min) (human sEH) |
|---|---|---|---|---|---|
| 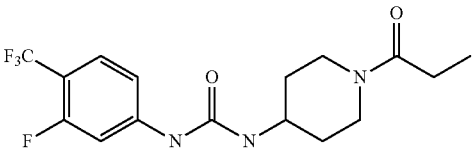 31 | 361.33 | 3.76 | 1.9 | 2.94 ± | 0.01 |
| 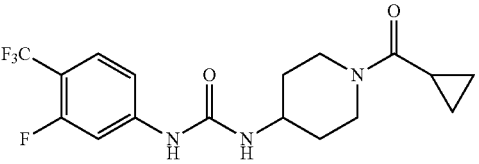 32 | 389.34 | 3.94 | 2.0 | 0.38 ± 0.08 | 8.2 |
| 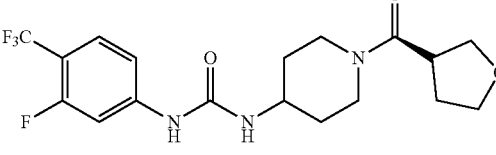 33 | 403.37 | 3.41 | 1.9 | 2.09 ± 0.24 | 5.3 |
| 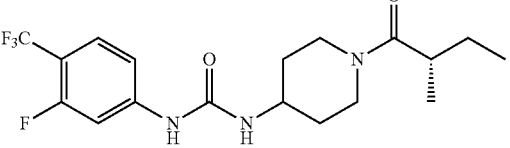 34 | 389.39 | 5.48 | 2.8 | 0.37 ± 0.03 | 13 |
| 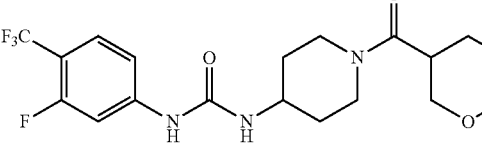 35 | 417.40 | 3.84 | 2.3 | 2.66 ± 0.19 | 6.8 |
| 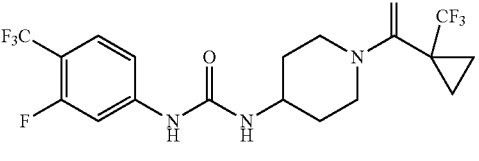 36 | 441.34 | 5.52 | 2.5 | 0.08 ± 0.01 | 21 |

TABLE 3-continued
POTENT PIPERIDINE INHIBITORS OF SHE
| Structure and Compound No. | Mol. Weight | Exp. logP[a] | Cal. logP[b] | Ki (nM) (human sEH) | t$_{1/2}$ (min) (human sEH) |
|---|---|---|---|---|---|
| 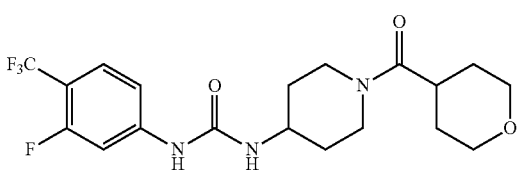 37 | 417.40 | 3.52 | 1.1 | 3.83 ± 0.41 | 6.9 |
| 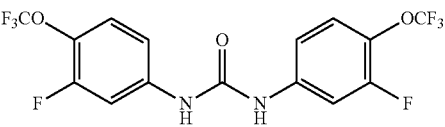 38 | 416.23 | ND | ND | 1.95 ± 0.30 | ND |
| 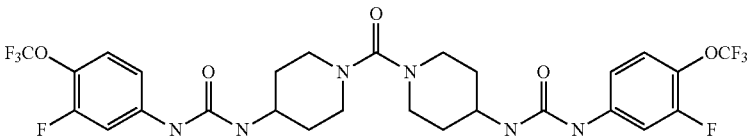 39 | 668.50 | ND | ND | 10.1 ± 1.8 | ND |
| 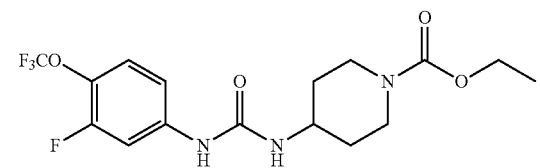 40 | 393.34 | 5.94 | 3.3 | <0.05 | 18 |
| 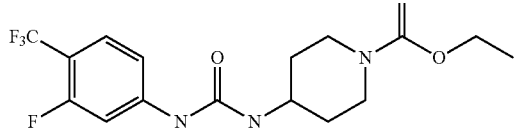 41 | 3.77.34 | 5.46 | 3.6 | 0.38 ± 0.03 | 7.6 |
| 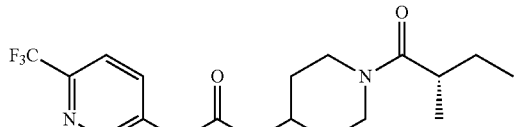 42 | 372.39 | 3.22 | 1.7 | 45.0 ± 2.3 | 3.7 |
| 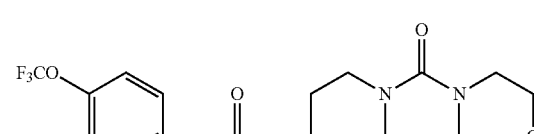 43 | 434.39 | 3.93 | 2.6 | 0.70 ± 0.06 | 15 |

TABLE 3-continued
POTENT PIPERIDINE INHIBITORS OF sEH
| Structure and Compound No. | Mol. Weight | Exp. logP[a] | Cal. logP[b] | Ki (nM) (human sEH) | t$_{1/2}$ (min) (human sEH) |
|---|---|---|---|---|---|
| 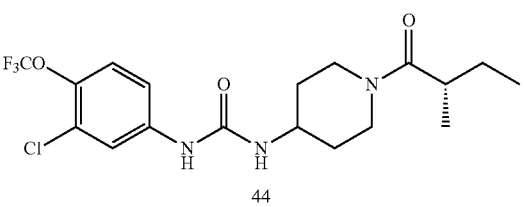 [SMILES: CC[C@H](C)C(=O)N1CCC(NC(=O)Nc2ccc(OC(F)(F)F)c(Cl)c2)CC1] 44 | 421.85 | 7.70 | 3.0 | 3.35 ± 0.42 | 10 |
| 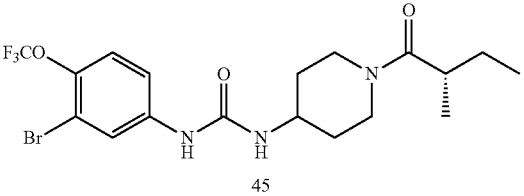 [SMILES: CC[C@H](C)C(=O)N1CCC(NC(=O)Nc2ccc(OC(F)(F)F)c(Br)c2)CC1] 45 | 465.29 | 8.07 | 3.2 | 3.40 ± 1.38 | 9.3 |
| 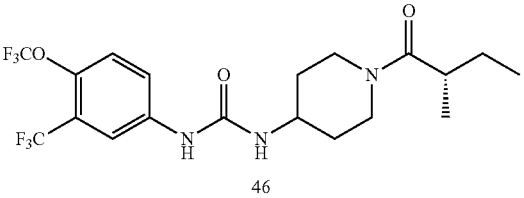 [SMILES: CC[C@H](C)C(=O)N1CCC(NC(=O)Nc2ccc(OC(F)(F)F)c(C(F)(F)F)c2)CC1] 46 | 455.40 | 9.02 | 3.7 | 9.91 ± 3.37 | 5.9 |
| 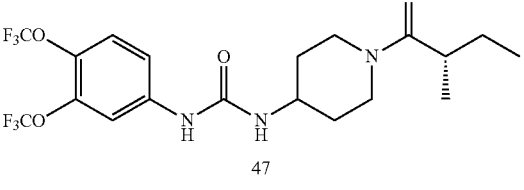 47 | 471.40 | 10.62 | 3.1 | 9.07 ± 0.36 | 11 |
| 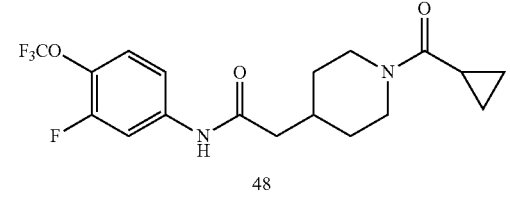 [SMILES: O=C(CC1CCN(C(=O)C2CC2)CC1)Nc1ccc(OC(F)(F)F)c(F)c1] 48 | 388.36 | 5.11 | 2.3 | 6.60 ± 0.01 | 3.3 |
| 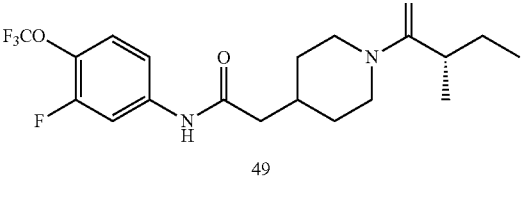 49 | 404.41 | 7.68 | 3.1 | 3.14 ± 0.70 | 4.5 |

TABLE 3-continued

POTENT PIPERIDINE INHIBITORS OF SHE

| Structure and Compound No. | Mol. Weight | Exp. logP$^a$ | Cal. logP$^b$ | Ki (nM) (human sEH) | t$_{1/2}$ (min) (human sEH) |
|---|---|---|---|---|---|
| [Structure of compound 51: F$_3$CO- and F-substituted phenyl urea linked to piperidine with butanoyl group] 51 | 405.39 | ND | 2.5 | 0.06 ± 0.01 | ND |

In another group of embodiments, the '496 patent sets forth sEH inhibitors that provide alternate substrates for the enzyme that are turned over slowly. Exemplars of this category of inhibitors are phenyl glycidols (e.g., S, S-4-nitrophenylglycidol), and chalcone oxides. The '496 patent notes that suitable chalcone oxides include 4-phenylchalcone oxide and 4-fluourochalcone oxide. The phenyl glycidols and chalcone oxides are believed to form stable acyl enzymes.

Additional inhibitors of sEH suitable for use in the methods are set forth in U.S. Pat. No. 6,150,415 (the '415 patent) and U.S. Pat. No. 6,531,506 (the '506 patent).

Derivatives of the sEHI can be designed. For example, dicyclohexyl thio urea can be oxidized to dicyclohexylcarbodiimide which, with enzyme or aqueous acid (physiological saline), will form an active dicyclohexylurea. Alternatively, the acidic protons on carbamates or ureas can be replaced with a variety of substituents which, upon oxidation, hydrolysis or attack by a nucleophile such as glutathione, will yield the corresponding parent structure. These materials are known as prodrugs or protoxins (*Goodman and Gilman's The Pharmacological Basis of Therapeutics*, 13th Edition, 2017, McGraw-Hill). Esters, for example, are common prodrugs which are released to give the corresponding alcohols and acids enzymatically (Yoshigae et al., Chirality, 9:661-666 (1997)). The drugs and prodrugs can be chiral for greater specificity. These derivatives have been extensively used in medicinal and agricultural chemistry to alter the pharmacological properties of the compounds such as enhancing water solubility, improving formulation chemistry, altering tissue targeting, altering volume of distribution, and altering penetration. They also have been used to alter toxicology profiles.

There are many prodrugs possible, but replacement of one or both of the two active hydrogens in the ureas described here or the single active hydrogen present in carbamates is particularly attractive. Such derivatives have been extensively described by Fukuto and associates. These derivatives have been extensively described and are commonly used in agricultural and medicinal chemistry to alter the pharmacological properties of the compounds. (Black et al., Journal of Agricultural and Food Chemistry, 21(5):747-751 (1973); Fahmy et al, J. Agricultural and Food Chemistry, 26(3):550-556 (1978); Jojima et al., Journal of Agricultural and Food Chemistry, 31(3):613-620 (1983); and Fahmy et al., Journal of Agricultural and Food Chemistry, 29(3):567-572 (1981).)

Such active proinhibitor derivatives are contemplated, and the just-cited references are incorporated herein by reference. Without being bound by theory, it is believed that suitable inhibitors mimic the enzyme transition state so that there is a stable interaction with the enzyme catalytic site. The inhibitors appear to form hydrogen bonds with the nucleophilic carboxylic acid and a polarizing tyrosine of the catalytic site.

In some embodiments, the sEH inhibitor used in the methods taught herein is a "soft drug." Soft drugs are compounds of biological activity that are rapidly inactivated by enzymes as they move from a chosen target site. EETs and simple biodegradable derivatives administered to an area of interest may be considered to be soft drugs in that they are likely to be enzymatically degraded by sEH as they diffuse away from the site of interest following administration. Some sEHI, however, may diffuse or be transported following administration to regions where their activity in inhibiting sEH may not be desired. Thus, multiple soft drugs for treatment have been prepared. These include but are not limited to carbamates, esters, carbonates and amides placed in the sEHI, approximately 7.5 angstroms from the carbonyl of the central pharmacophore. These are highly active sEHI that yield biologically inactive metabolites by the action of esterase and/or amidase. Groups such as amides and carbamates on the central pharmacophores can also be used to increase solubility for applications in which that is desirable in forming a soft drug. Similarly, easily metabolized ethers may contribute soft drug properties and also increase the solubility.

In some embodiments, sEH inhibition can include the reduction of the amount of sEH. As used herein, therefore, sEH inhibitors can therefore encompass nucleic acids that inhibit expression of a gene encoding sEH. Many methods of reducing the expression of genes, such as reduction of transcription and siRNA, are known, and are discussed in more detail below.

In various embodiments, the inhibitor inhibits sEH without also significantly inhibiting microsomal epoxide hydrolase ("mEH"). In various embodiments, at concentrations of 100 μM, the inhibitor inhibits sEH activity by at least 50% while not inhibiting mEH activity by more than 10%. Compounds have an IC$_{50}$ (inhibition potency or, by definition, the concentration of inhibitor which reduces enzyme activity by 50%) of less than about 100 μM. Inhibitors with IC$_{50}$s of less than 100 μM are of use, e.g., compounds with IC$_{50}$s of less than 75 μM e.g., compounds with an IC$_{50}$ of 50 μM, 40 μM, μM, 25 μM, 20 μM, 15 μM, 10 μM, 5 μM, 3 μM, 2 μM, 1 μM, 100 nM, 10 nM, 1.0 nM, or even less. Assays for determining sEH activity are known in the art and described elsewhere herein. The IC$_{50}$ determination of the inhibitor can be made with respect to an sEH enzyme from the species subject to treatment (e.g., the subject receiving the inhibitor of sEH).

b. cis-epoxyeicosantrienoic acids ("EETs"), epoxyeicosatetraenoic acids (EEQs) and epoxydocosapentaenoic acids (EDPs)

EETs, which are epoxides of arachidonic acid, are known to be effectors of blood pressure, regulators of inflammation, and modulators of vascular permeability. Hydrolysis of the epoxides by sEH diminishes this activity. Inhibition of sEH raises the level of EETs since the rate at which the EETs are hydrolyzed into dihydroxyeicosatrienoic acids ("DHETs") is reduced.

It has long been believed that EETs administered systemically would be hydrolyzed too quickly by endogenous sEH to be helpful. For example, in one prior report of EETs administration, EETs were administered by catheters inserted into mouse aortas. The EETs were infused continuously during the course of the experiment because of concerns over the short half-life of the EETs. See, Liao and Zeldin, International Publication WO 01/10438 (hereafter "Liao and Zeldin"). It also was not known whether endogenous sEH could be inhibited sufficiently in body tissues to permit administration of exogenous EET to result in increased levels of EETs over those normally present. Further, it was thought that EETs, as epoxides, would be too labile to survive the storage and handling necessary for therapeutic use.

Studies from the laboratory of the present inventors, however, showed that systemic administration of EETs in conjunction with inhibitors of sEH had better results than did administration of sEH inhibitors alone. EETs were not administered by themselves in these studies since it was anticipated they would be degraded too quickly to have a useful effect. Additional studies from the laboratory of the present inventors have since shown, however, that administration of EETs by themselves has had therapeutic effect. Without wishing to be bound by theory, it is surmised that the exogenous EET overwhelms endogenous sEH, and allows EETs levels to be increased for a sufficient period of time to have therapeutic effect. Thus, EETs can be exposed to the stem cells in vitro or co-administered in vivo with or without also preconditioning with or administering an sEHI to provide a therapeutic effect. Moreover, EETs, if not exposed to acidic conditions or to sEH are stable and can withstand reasonable storage, handling and administration.

In short, sEHI, EETs, EEQs and EDPs, or co-administration of sEHIs and one or more of EETs, EEQs and EDPs, can be used for in vitro preconditioning of stem cells or in vivo co-administration with stem cells in the present methods. In some embodiments, one or more EETs, EEQs and/or EDPs are administered to the patient without also administering an sEHI. In some embodiments, one or more EETs, EEQs and/or EDPs are administered shortly before or concurrently with administration of an sEH inhibitor to slow hydrolysis of the EETs, EEQs and/or EDPs. In some embodiments, one or more EETs, EEQs and/or EDPs are administered after administration of an sEH inhibitor, but before the level of the sEHI has diminished below a level effective to slow the hydrolysis of the EETs, EEQs and/or EDPs.

EETs useful in the methods include 14,15-EET, 8,9-EET and 11,12-EET, and 5,6 EETs. Preferably, the EETs are provided in vitro or administered in vivo as the methyl ester, which is more stable. Persons of skill will recognize that the EETs are regioisomers, such as 8S,9R- and 14R,15S-EET. 8,9-EET, 11,12-EET, and 14R,15S-EET, are commercially available from, for example, Sigma-Aldrich (catalog nos. E5516, E5641, and E5766, respectively, Sigma-Aldrich Corp., St. Louis, Mo.). EEQs of use for preconditioning exposure in vitro or co-administration in vivo include without limitation 17,18-epoxyeicosatetraenoic acid (17,18-EEQ). EDPs of use for preconditioning exposure in vitro or co-administration in vivo include without limitation 19,20-epoxydocosapentaenoic (19,20-EDP).

If desired, EETs, EEQs and/or EDPs, analogs, or derivatives that retain activity can be used in place of or in combination with unmodified EETs, EEQs and/or EDPs. EETs, EEQs and/or EDPs analogs are defined herein as compounds with structural substitutions or alterations in an EETs, EEQs and/or EDPs, and include structural analogs in which one or more EETs, EEQs and/or EDPs olefins are removed or replaced with acetylene or cyclopropane groups, analogs in which the epoxide moiety is replaced with oxitane or furan rings and heteroatom analogs. In other analogs, the epoxide moiety is replaced with ether, alkoxides, urea, amide, carbamate, difluorocycloprane, or carbonyl, while in others, the carboxylic acid moiety is stabilized by blocking beta oxidation or is replaced with a commonly used mimic, such as a nitrogen heterocycle, a sulfonamide, or another polar functionality. In some embodiments, olefins not critical for biological activity are removed and omega oxidation is reduced. In preferred forms, the analogs or derivatives are relatively stable as compared to an unmodified EETs, EEQs and/or EDPs because they are more resistant than an unmodified EETs, EEQs and/or EDPs to sEH and to chemical breakdown. "Relatively stable" means the rate of hydrolysis by sEH is at least 25% less than the hydrolysis of the unmodified EETs, EEQs and/or EDPs in a hydrolysis assay, and more preferably 50% or more lower than the rate of hydrolysis of an unmodified EETs, EEQs and/or EDPs. Liao and Zeldin show, for example, episulfide and sulfonamide EETs derivatives. In some embodiments, amide and ester derivatives of EETs, EEQs and/or EDPs and that are relatively stable are provided for preconditioning exposure in vitro or co-administration in vivo. Whether or not a particular EETs, EEQs and/or EDPs analog or derivative has the biological activity of the unmodified EETs, EEQs and/or EDPs can be readily determined by using it in standard assays.

In some embodiments, the EETs, EEQs and/or EDPs are embedded or otherwise placed in a material that releases the EETs, EEQs and/or EDPs over time. Materials suitable for promoting the slow release of compositions such as EETs, EEQs and/or EDPs are known in the art. Optionally, one or more sEH inhibitors may also be placed in the slow release material.

Conveniently, the EETs, EEQs and/or EDPs can be administered orally. Since EETs are subject to degradation under acidic conditions, EETs intended for oral administration can be coated with a coating resistant to dissolving under acidic conditions, but which dissolve under the mildly basic conditions present in the intestines. Suitable coatings, commonly known as "enteric coatings" are widely used for products, such as aspirin, which cause gastric distress or which would undergo degradation upon exposure to gastric acid. By using coatings with an appropriate dissolution profile, the coated substance can be released in a chosen section of the intestinal tract. For example, a substance to be released in the colon is coated with a substance that dissolves at pH 6.5-7, while substances to be released in the duodenum can be coated with a coating that dissolves at pH values over 5.5. Such coatings are commercially available from, for example, Rohm Specialty Acrylics (Rohm America LLC, Piscataway, N.J.) under the trade name "Eudragit®". The choice of the particular enteric coating is not critical to the practice.

c. Phosphodiesterase Inhibitors (PDEi)

Phosphodiesterase inhibitors (PDEi) are well known anti-inflammatory agents. Many different classes of isozyme selective PDEi lead to remarkable increases in the plasma levels of a broad range of epoxy-fatty acids (EFA). The magnitude of this increase is so dramatic that PDEi can elevate epoxy-fatty acids as well as highly potent inhibitors of soluble epoxide hydrolase. Accordingly, levels of epoxy-fatty acids (e.g., in blood, plasma, serum) can be increased by administration of a phosphodiesterase inhibitor (PDEi).

The PDEi may or may not be selective, specific or preferential for cAMP. Exemplary PDEs that degrade cAMP include without limitation PDE3, PDE4, PDE7, PDE8 and PDE10. Exemplary cAMP selective hydrolases include PDE4, 7 and 8. Exemplary PDEs that hydrolyse both cAMP and cGMP include PDE1, PDE2, PDE3, PDE10 and PDE11. Isoenzymes and isoforms of PDEs are well known in the art. See, e.g., Boswell-Smith et al., Brit. J. Pharmacol. 147: S252-257 (2006), and Reneerkens, et al., Psychopharmacology (2009) 202:419-443, the contents of which are incorporated herein by reference.

In some embodiments, the PDE inhibitor is a non-selective inhibitor of PDE. Exemplary non-selective PDE inhibitors that find use include without limitation caffeine, theophylline, isobutylmethylxanthine, aminophylline, pentoxifylline, vasoactive intestinal peptide (VIP), secretin, adrenocorticotropic hormone, pilocarpine, alpha-melanocyte stimulating hormone (MSH), beta-MSH, gamma-MSH, the ionophore A23187, prostaglandin E1.

In some embodiments, the PDE inhibitor used specifically or preferentially inhibits PDE4. Exemplary inhibitors that selectively inhibit PDE4 include without limitation rolipram, roflumilast, cilomilast, ariflo, HT0712, ibudilast and mesembrine.

In some embodiments, the PDE inhibitor used specifically or preferentially inhibits a cAMP PDE, e.g., PDE4, PDE7 or PDE8. In some embodiments, the PDE inhibitor used inhibits a cAMP PDE, e.g., PDE1, PDE2, PDE3, PDE4, PDE7, PDE8, PDE10 or PDE11. Exemplary agents that inhibit a cAMP phosphodiesterase include without limitation rolipram, roflumilast, cilomilast, ariflo, HT0712, ibudilast, mesembrine, cilostamide, enoxamone, milrinone, siguazodan and BRL-50481.

In some embodiments, the PDE inhibitor used specifically inhibits PDE5. Exemplary inhibitors that selectively inhibit PDE5 include without limitation sildenafil, zaprinast, tadalafil, udenafil, avanafil and vardenafil.

d. Assays for Epoxide Hydrolase Activity

Any of a number of standard assays for determining epoxide hydrolase activity can be used to determine inhibition of sEH. For example, suitable assays are described in Gill. et al., Anal Biochem 131:273-282 (1983); and Borhan, et al., Analytical Biochemistry 231:188-200 (1995)). Suitable in vitro assays are described in Zeldin et al., J Biol. Chem. 268:6402-6407 (1993). Suitable in vivo assays are described in Zeldin et al., Arch Biochem Biophys 330:87-96 (1996). Assays for epoxide hydrolase using both putative natural substrates and surrogate substrates have been reviewed (see, Hammock, ct al. In: Methods in Enzymology, Volume III, Steroids and Isoprenoids, Part B, (Law, J. H. and H. C. Rilling, eds. 1985), Academic Press, Orlando, Fla., pp. 303-311 and Wixtrom et al., In: Biochemical Pharmacology and Toxicology, Vol. 1: Methodological Aspects of Drug Metabolizing Enzymes, (Zakim, D. and D. A. Vessey, eds. 1985), John Wiley & Sons, Inc., New York, pp. 1-93. Several spectral based assays exist based on the reactivity or tendency of the resulting diol product to hydrogen bond (see, e.g., Wixtrom, supra, and Hammock. Anal. Biochem. 174: 291-299 (1985) and Dietze, et al. Anal. Biochem. 216:176-187 (1994)).

The enzyme also can be detected based on the binding of specific ligands to the catalytic site which either immobilize the enzyme or label it with a probe such as dansyl, fluoracein, luciferase, green fluorescent protein or other reagent. The enzyme can be assayed by its hydration of EETs, its hydrolysis of an epoxide to give a colored product as described by Dietze et al., 1994, supra, or its hydrolysis of a radioactive surrogate substrate (Borhan et al., 1995, supra). The enzyme also can be detected based on the generation of fluorescent products following the hydrolysis of the epoxide. Numerous methods of epoxide hydrolase detection have been described (see, e.g., Wixtrom, supra).

The assays are normally carried out with a recombinant enzyme following affinity purification. They can be carried out in crude tissue homogenates, cell culture or even in vivo, as known in the art and described in the references cited above.

5. Co-Inhibition Strategies

In various embodiments, the sEHI is co-administered with an enhancing or synergizing agent. Illustrative agents that enhance the activity or efficaciousness of directly inhibiting soluble epoxide hydrolase include without limitation inhibitors of cyclooxygenase-2 (COX-2), inhibitors of phosphodiesterase, agonists of peroxisome proliferator activated receptor alpha (PPARα) and agonists of peroxisome proliferator activated receptor gamma (PPARγ).

Illustrative selective or preferential inhibitors of COX-2 that may be co-administered with an inhibitor of soluble epoxide hydrolase include without limitation celecoxib, valdecoxib, lumiracoxib, etoricoxib, and rofecoxib. Illustrative inhibitors of phosphodiesterase 4 that may be co-administered with an inhibitor of soluble epoxide hydrolase include without limitation rolipram, roflumilast, cilomilast, ariflo, HT0712, ibudilast and mesembrine. Illustrative inhibitors of phosphodiesterase 5 that may be co-administered with an inhibitor of soluble epoxide hydrolase include without limitation sildenafil, zaprinast, tadalafil, udenafil, avanafil and vardenafil. Illustrative agonists of PPARα that may be co-administered with an inhibitor of soluble epoxide hydrolase include without limitation clofibrate. gemfibrozil, ciprofibrate, bezafibrate, and fenofibrate. Illustrative agonists of PPARγ that may be co-administered with an inhibitor of soluble epoxide hydrolase include without limitation thiazolidinediones (TZDs).

In various embodiments, a compound with combined functionality to concurrently inhibit sEH and COX-2 is administered. Urea-containing pyrazoles that function as dual inhibitors of cyclooxygenase-2 and soluble epoxide hydrolase are described, e.g., in Hwang, et al., *J Med Chem.* (2011) 28; 54(8):3037-50 and WO 2012/082647.

A general structure of inhibitors that inhibit both COX-2 and sEH are provided below.

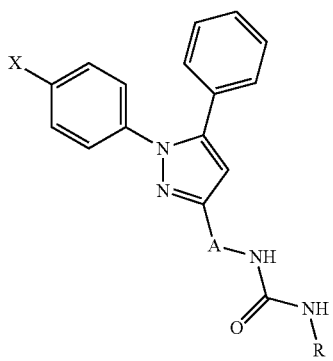

general structure may have different functional groups on:
X: MeSO₂ or H₂NSO₂
A: various carbon linkers
R: carbocyclic, aryl groups, or heterocyclic groups Inhibitory activities against sEH, COX-1 and COX-2 of illustrative dual inhibitors of COX-2 and sEH are provided in Table 4 below.

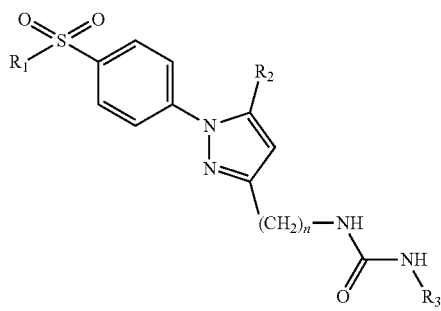

In some embodiments, the dual inhibitor of sEH and COX-2 is 4-(5-phenyl-3-{3-[3-(4-trifluoromethyl-phenyl)-ureido]-propyl}-pyrazol-1-yl)-benzenesulfonamide (PTUPB). In some embodiments, the dual inhibitor of sEH and COX 2 is a compound in Table 4 selected from the group consisting of:
a) compound 1860 (1-Adamantan-1-yl-3-[1-(4-methane-sulfonyl-phenyl)-5-phenyl-1H-pyrazol-3-ylmethyl]-urea),
b) compound 2321 (1-Cycloheptyl-3-[1-(4-methanesulfo-nyl-phenyl)-5-phenyl-1H-pyrazol-3-ylmethyl]-urea),
c) compound 2322 (1-[1-(4-Methanesulfonyl-phenyl)-5-phenyl-1H-pyrazol-3-ylmethyl]-3-phenyl-urea),
d) compound 2323 (1-[1-(4-Methanesulfonyl-phenyl)-5-phenyl-1H-pyrazol-3-ylmethyl]-3-(4-trifluoromethoxy-phenyl)-urea),
e) compound 2324 (1-[1-(4-Methanesulfonyl-phenyl)-5-phenyl-1H-pyrazol-3-ylmethyl]-3-(4-trifluoromethyl-phenyl)-urea),
f) compound 1861 (1-[1-(4-Methanesulfonyl-phenyl)-5-phenyl-1H-pyrazol-3-ylmethyl]-3-(3-trifluoromethyl-phenyl)-urea),
g) compound 2107 (4-{5-Phenyl-3-[3-(3-trifluoromethyl-phenyl)-ureidomethyl]-pyrazol-1-yl}-benzenesulfona-mide),
h) compound 2106 (1-[5-tert-Butyl-1-(4-methanesulfonyl-phenyl)-1H-pyrazol-3-ylmethyl]-3-(3-trifluoromethyl-phenyl)-urea),
i) compound 2121 (4-{5-Phenyl-3-[3-(3-trifluoromethyl-phenyl)-ureido]-pyrazol-1-yl}-benzenesulfonamide),
j) compound 2313 (4-(5-Phenyl-3-{2-[3-(3-trifluoromethyl-phenyl)-ureido]-ethyl}-pyrazol-1-yl)-benzenesulfona-mide),
compound 1862 (1-{3-[1-(4-Methanesulfonyl-phenyl)-5-phenyl-1H-pyrazol-3-yl]-propyl}-3-(3-trifluoromethyl-phenyl)-urea),
k) compound 2246 (4-(5-Phenyl-3-{3-[3-(3-trifluorom-ethyl-phenyl)-ureido]-propyl}-pyrazol-1-yl)-benzene-sulfonamide),

TABLE 4

Inhibitory activities against sEH, COX-1 and COX-2.

| sEH-COX-2 dual inhibitor | $R_1$ | $R_2$ | $R_3$ | n | COX-2 (μM) | COX-1 (% inhibition at 100 mM) | sEH (nM) |
|---|---|---|---|---|---|---|---|
| 1860 | Me | Ph | Adamantyl | 1 | >10 | 12.7 | 25 ± 1 |
| 2321 | Me | Ph | cHep | 1 | >10 | 3.4 | 2.6 ± 0.3 |
| 2322 | Me | Ph | Ph | 1 | >10 | 9.9 | 47 ± 4 |
| 2323 | Me | Ph | p-CF₃O—Ph | 1 | 7 | 10.4 | 6.0 ± 0.5 |
| 2324 | Me | Ph | p-CF₃—Ph | 1 | >10 | 10.7 | 110 ± 5 |
| 1861 | Me | Ph | m-CF₃—Ph | 1 | 2.5 | 7.8 | 72 ± 8 |
| 2107 | NH₂ | Ph | m-CF₃—Ph | 1 | 1 | 16.9 | 84 ± 6 |
| 2106 | Me | t-butyl | m-CF₃—Ph | 1 | >10 | 2.4 | 32 ± 3 |
| 2121 | NH₂ | Ph | m-CF₃—Ph | 0 | 2 | 33.9 | 88 ± 5 |
| 2313 | NH₂ | Ph | m-CF₃—Ph | 2 | 1 | 22.0 | 26 ± 3 |
| 1862 | Me | Ph | m-CF₃—Ph | 3 | 3 | 6.4 | 3.4 ± 0.2 |
| 2246 | NH₂ | Ph | m-CF₃—Ph | 3 | 0.71 | 27.2 | 4.1 ± 0.4 |
| 2152 | NH₂ | p-Me—Ph | m-CF₃—Ph | 3 | 2.8 | 12.1 | 10 ± 1 |
| 2325 | NH₂ | Ph | 2,6-diMe—Ph | 3 | >10 | 6.2 | 1550 ± 70 |
| 2245 | NH₂ | Ph | Ph | 3 | >10 | 15.8 | 0.8 ± 0.1 |
| 2326 | NH₂ | Ph | 1-Adamantyl | 3 | 7 | 6.7 | 0.5 ± 0.1 |
| 2247 | NH₂ | Ph | c-Hep | 3 | 2 | 10.2 | 0.5 ± 0.1 |
| 2327 | NH₂ | Ph | p-Cl—Ph | 3 | 6 | 15.2 | 0.8 ± 0.1 |
| 2328 (SHH07009A) | NH₂ | Ph | p-CF₃—Ph | 3 | 1.26 | 22.7 | 0.9 ± 0.1 |
| 2329 (SHH07009B) | NH₂ | Ph | p-CF₃O—Ph | 3 | 0.92 | 13.8 | 0.5 ± 0.1 | l) compound 2152 (4-(5-p-Tolyl-3-{3-[3-(3-trifluoromethyl-phenyl)-ureido]-propyl}-pyrazol-1-yl)-benzenesulfonamide), m) compound 2325 (4-(3-{3-[3-(2,6-Diisopropyl-phenyl)-ureido]-propyl}-5-phenyl-pyrazol-1-yl)-benzenesulfonamide), n) compound 2245 (4-{5-Phenyl-3-[3-(3-phenyl-ureido)-propyl]-pyrazol-1-yl}-benzenesulfonamide), o) compound 2326 (4-{3-[3-(3-Adamantan-1-yl-ureido)-propyl]-5-phenyl-pyrazol-1-yl}-benzenesulfonamide), p) compound 2247 (4-{3-[3-(3-Cycloheptyl-ureido)-propyl]-5-phenyl-pyrazol-1-yl}-benzenesulfonamide), q) compound 2327 (4-(3-{3-[3-(4-Chloro-phenyl)-ureido]-propyl}-5-phenyl-pyrazol-1-yl)-benzenesulfonamide), r) compound 2328 (4-(5-Phenyl-3-{3-[3-(4-trifluoromethyl-phenyl)-ureido]-propyl}-pyrazol-1-yl)-benzenesulfonamide); and s) compound 2329 (4-(5-Phenyl-3-{3-[3-(4-trifluoromethoxy-phenyl)-ureido]-propyl}-pyrazol-1-yl)-benzenesulfonamide).

In various embodiments, a compound with combined functionality to concurrently inhibit sEH and phosphodiesterase 4 (PDE4) is administered. Dual inhibitors of PDE4 and soluble epoxide hydrolase are described, e.g., in co-pending and co-owned U.S. Provisional Appl. No. 62/574,908, filed on Oct. 20, 2017 and entitled "ORALLY AVAILABLE sEH/PDE4 DUAL INHIBITORS FOR TREATMENT OF INFLAMMATORY PAIN," which is hereby incorporated herein by reference in its entirety for all purposes.

A general structure of inhibitors that inhibit both PDE4 and sEH are provided below, in Table 5.

TABLE 5

Evaluation of dual sEH/PDE4 inhibitors in vitro activity

| ID | $R_1$ | $R_2$ | $IC_{50}{}^a$ [nM] | cAMP increase[b] (% of Rolipram) | w.s.[c] [μM] |
|---|---|---|---|---|---|
| 1 | $CF_3$ | OMe | 0.6 ± 0.1 | 240 ± 14 | 37.5 |
| 2 | $CF_3$ | — | 15 ± 3 | 180 ± 12 | 37.5 |
| 3 | Me | — | 180 ± 40 | 200 ± 11 | 37.5 |

| ID | $R_3$ | $R_4$ | $IC_{50}{}^a$ [nM] | cAMP increase[b] (% of Rolipram) | w.s.[c] [μM] |
|---|---|---|---|---|---|
| 4 | — | — | 2 ± 0.9 | 160 ± 12 | 100 |
| 5 | F | — | 2.8 ± 0.4 | 110 ± 13 | 100 |
| 6 | — | NHCOMe | 2.9 ± 1.1 | 140 ± 15 | 100 |
| 7 | — | NHCOEt | 3.7 ± 1 | 150 ± 18 | 50 |
| 8 | Me | NHCOMe | 13 ± 2 | 140 ± 15 | 20 |
| 9 | pyrrolidin-2-one | | 3 ± 3 | 130 ± 25 | 100 |

TABLE 5-continued

| 10 | NHCOMe | — | 44 ± 5 | 100 ± 19 | 50 |
| 11 | OMe | — | 1 ± 0.2 | 160 ± 17 | 100 |
| 14 | $OCHF_2$ | — | 1.5 ± 0.4 | 150 ± 14 | 10 |
| 19 | — | $OcC_5H_9$ | 0.4 ± 0.1 | 147 ± 9 | 10 |
| 20 | F | $OcC_5H_9$ | 0.4 ± 0 | 222 ± 8 | 100 |

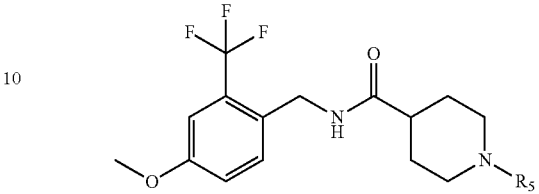

| ID | $R_5$ | $IC_{50}{}^a$ [nM] | cAMP increase[b] (% of Rolipram) | w.s.[c] [μM] |
|---|---|---|---|---|
| TPPU[D] | — | 3.7 | 40 ± 10 | 200 |
| 21 | BOC | 1.7 ± 0.7 | 100 ± 12 | 100 |
| 22 | — | 370 ± 170 | 138 ± 5 | 1000 |
| 23/MPPA | COEt | 2.1 ± 0.5 | 200 ± 19 | 100 |
| 24 | COPr | 4 ± 2 | 110 ± 16 | 50 |
| 25 | s-Bu | 7 ± 3 | 160 ± 11 | 0.5 |
| 26 | Et | 109 ± 16 | 60 ± 10 | 1000 |
| 27 | n-Pr | 190 ± 20 | 60 ± 14 | 1000 |

In vitro evaluation of sEH/PDE4 dual inhibitors Group 1: 1-3, Group 2: 4-11, 14, 19-20 and Group 3: 21-27.
[a]The sEH IC50 values were recorded on recombinant human sEH protein (hsEH) using PHOME as substrate at 5 μM concentration30;
[b]PDE4 inhibition was evaluated by cAMP increase in live human embryonic kidney (HEK) cells, transfected with a PKA biosensor and visualized relative to Rolipram at 1 μM;
[c]water solubility (w.s.) is measured in sodium phosphate buffer (0.1M, pH 7.4) with 1% DMSO by precipitation.

In some embodiments, the dual inhibitor of PDE4 and sEH is a compound in Table 5 selected from the group consisting of:

a) compound 1; 3-(Cyclopentyloxy)-4-methoxy-N-(4-methoxy-2-(trifluoromethyl)benzyl)benzamide;

b) compound 2; 3-(Cyclopentyloxy)-4-methoxy-N-(2-(trifluoromethyl)benzyl)benzamide;

c) compound 3; 3-(Cyclopentyloxy)-4-methoxy-N-(2-methylbenzyl)benzamide;

d) compound 4; N-(4-Methoxy-2-(trifluoromethyl)benzyl) benzamide;

e) compound 5; 4-Fluoro-N-(4-methoxy-2-(trifluoromethyl) benzyl)benzamide;

f) compound 6; 3-Acetamido-N-(4-methoxy-2-(trifluoromethyl)benzyl)benzamide;

g) compound 7; N-(4-Methoxy-2-(trifluoromethyl)benzyl)-3-propionamidobenzamide;

h) compound 8; 3-Acetamido-N-(4-methoxy-2-(trifluoromethyl)benzyl)-4-methylbenzamide;

i) compound 9; N-(4-Methoxy-2-(trifluoromethyl)benzyl)-2-oxoindoline-6-carboxamide;

j) compound 10; 4-Acetamido-N-(4-methoxy-2-(trifluoromethyl)benzyl)benzamide;

k) compound 11; 4-Methoxy-N-(4-methoxy-2-(trifluoromethyl)benzyl)benzamide;

l) compound 14; 4-(Difluoromethoxy)-N-(4-methoxy-2-(trifluoromethyl)benzyl)benzamide;

m) compound 19; 3-(Cyclopentyloxy)-N-(4-methoxy-2-(trifluoromethyl)benzyl)benzamide;

n) compound 20; 3-(Cyclopentyloxy)-4-fluoro-N-(4-methoxy-2-(trifluoromethyl)benzyl)benzamide;

o) compound 21; tert-Butyl 4-((4-methoxy-2-(trifluoromethyl)benzyl)carbamoyl)piperidine-1-carboxylate;

p) compound 22; N-(4-Methoxy-2-(trifluoromethyl)benzyl) piperidine-4-carboxamide;

q) compound 23; N-(4-methoxy-2-(trifluoromethyl)benzyl)-1-propionylpiperidine-4-carboxamide (MPPA);
r) compound 24; 1-Butyryl-N-(4-methoxy-2-(trifluoromethyl)benzyl)piperidine-4-carboxamide;
s) compound 25; N-(4-Methoxy-2-(trifluoromethyl)benzyl)-1-(2-methylbutanoyl)piperidine-4-carboxamide;
t) compound 26; 1-Ethyl-N-(4-methoxy-2-(trifluoromethyl)benzyl)piperidine-4-carboxamide; and
u) compound 27; N-(4-Methoxy-2-(trifluoromethyl)benzyl)-1-propylpiperidine-4-carboxamide.

e. Other Means of Inhibiting sEH Activity

Other means of inhibiting sEH activity or gene expression can also be used in the methods. For example, a nucleic acid molecule complementary to at least a portion of the human sEH gene can be used to inhibit sEH gene expression. Means for inhibiting gene expression using short RNA molecules, for example, are known. Among these are short interfering RNA (siRNA), small temporal RNAs (stRNAs), and micro-RNAs (miRNAs). Short interfering RNAs silence genes through a mRNA degradation pathway, while stRNAs and miRNAs are approximately 21 or 22 nt RNAs that are processed from endogenously encoded hairpin-structured precursors, and function to silence genes via translational repression. Sec, e.g., McManus et al., RNA, 8(6):842-50 (2002); Morris et al., Science, 305(5688):1289-92 (2004); He and Hannon, Nat Rev Genet. 5(7):522-31 (2004).

"RNA interference," a form of post-transcriptional gene silencing ("PTGS"), describes effects that result from the introduction of double-stranded RNA into cells (reviewed in Fire, A. Trends Genet 15:358-363 (1999); Sharp, P. Genes Dev 13:139-141 (1999); Hunter, C. Curr Biol 9:R440-R442 (1999); Baulcombe. D. Curr Biol 9:R599-R601 (1999); Vaucheret et al. Plant J 16: 651-659 (1998)). RNA interference, commonly referred to as RNAi, offers a way of specifically inactivating a cloned gene, and is a powerful tool for investigating gene function.

The active agent in RNAi is a long double-stranded (antiparallel duplex) RNA, with one of the strands corresponding or complementary to the RNA which is to be inhibited. The inhibited RNA is the target RNA. The long double stranded RNA is chopped into smaller duplexes of approximately 20 to 25 nucleotide pairs, after which the mechanism by which the smaller RNAs inhibit expression of the target is largely unknown at this time. While RNAi was shown initially to work well in lower eukaryotes, for mammalian cells, it was thought that RNAi might be suitable only for studies on the oocyte and the preimplantation embryo.

In mammalian cells other than these, however, longer RNA duplexes provoked a response known as "sequence non-specific RNA interference," characterized by the non-specific inhibition of protein synthesis.

Further studies showed this effect to be induced by dsRNA of greater than about 30 base pairs, apparently due to an interferon response. It is thought that dsRNA of greater than about 30 base pairs binds and activates the protein PKR and 2',5'-oligonucleotide synthetase (2',5'-AS). Activated PKR stalls translation by phosphorylation of the translation initiation factors eIF2α, and activated 2',5'-AS causes mRNA degradation by 2',5'-oligonucleotide-activated ribonuclease L. These responses are intrinsically sequence-nonspecific to the inducing dsRNA; they also frequently result in apoptosis, or cell death. Thus, most somatic mammalian cells undergo apoptosis when exposed to the concentrations of dsRNA that induce RNAi in lower eukaryotic cells.

More recently, it was shown that RNAi would work in human cells if the RNA strands were provided as pre-sized duplexes of about 19 nucleotide pairs, and RNAi worked particularly well with small unpaired 3' extensions on the end of each strand (Elbashir et al. Nature 411: 494-498 (2001)). In this report, siRNA were applied to cultured cells by transfection in oligofectamine micelles. These RNA duplexes were too short to elicit sequence-nonspecific responses like apoptosis, yet they efficiently initiated RNAi. Many laboratories then tested the use of siRNA to knock out target genes in mammalian cells. The results demonstrated that siRNA works quite well in most instances.

For purposes of reducing the activity of sEH, siRNAs to the gene encoding sEH can be specifically designed using computer programs. The cloning, sequence, and accession numbers of the human sEH sequence are set forth in Beetham et al., Arch. Biochem. Biophys. 305(1):197-201 (1993). An exemplary amino acid sequence of human sEH (GenBank Accession No. L05779; SEQ ID NO:1) and an exemplary nucleotide sequence encoding that amino acid sequence (GenBank Accession No. AAA02756; SEQ ID NO:2) are set forth in U.S. Pat. No. 5,445,956. The nucleic acid sequence of human sEH is also published as GenBank Accession No. NM_001979.4; the amino acid sequence of human sEH is also published as GenBank Accession No. NP_001970.2.

A program, siDESIGN from Dharmacon, Inc. (Lafayette, Colo.), permits predicting siRNAs for any nucleic acid sequence, and is available on the World Wide Web at dharmacon.com. Programs for designing siRNAs are also available from others, including Genscript (available on the Web at genscript.com/ssl-bin/app/mai) and, to academic and non-profit researchers, from the Whitehead Institute for Biomedical Research found on the worldwide web at "jura.wi.mit.edu/pubint/http://iona.wi.mit.edu/siRNAext/."

For example, using the program available from the Whitehead Institute, the following sEH target sequences and siRNA sequences can be generated:

```
1) Target:
                                    (SEQ ID NO: 3)
CAGTGTTCATTGGCCATGACTGG Sense-siRNA:
                                    (SEQ ID NO: 4)
5'-GUGUUCAUUGGCCAUGACUTT-3'

Antisense-siRNA:
                                    (SEQ ID NO: 5)
5'-AGUCAUGGCCAAUGAACACTT-3'

2) Target:
                                    (SEQ ID NO: 6)
GAAAGGCTATGGAGAGTCATCTG Sense-siRNA:
                                    (SEQ ID NO: 7)
5'-AAGGCUAUGGAGAGUCAUCTT-3'

Antisense-siRNA:
                                    (SEQ ID NO: 8)
5'-GAUGACUCUCCAUAGCCUUTT-3'

3) Target
                                    (SEQ ID NO: 9)
AAAGGCTATGGAGAGTCATCTGC Sense-siRNA:
                                    (SEQ ID NO: 10)
5'-AGGCUAUGGAGAGUCAUCUTT-3'
```

-continued

Antisense-siRNA:
(SEQ ID NO: 11)
5'-AGAUGACUCUCCAUAGCCUTT-3'

4) Target:
(SEQ ID NO: 12)
CAAGCAGTGTTCATTGGCCATGA

Sense-siRNA:
(SEQ ID NO: 13)
5'-AGCAGUGUUCAUUGGCCAUTT-3'

Antisense-siRNA:
(SEQ ID NO: 14)
5'-AUGGCCAAUGAACACUGCUTT-3'

5) Target:
(SEQ ID NO: 15)
CAGCACATGGAGGACTGGATTCC

Sense-siRNA:
(SEQ ID NO: 16)
5'-GCACAUGGAGGACUGGAUUTT-3'

Antisense-siRNA:
(SEQ ID NO: 17)
5'-AAUCCAGUCCUCCAUGUGCTT-3'

Alternatively, siRNA can be generated using kits which generate siRNA from the gene. For example, the "Dicer siRNA Generation" kit (catalog number T510001, Gene Therapy Systems, Inc., San Diego, Calif.) uses the recombinant human enzyme "dicer" in vitro to cleave long double stranded RNA into 22 bp siRNAs. By having a mixture of siRNAs, the kit permits a high degree of success in generating siRNAs that will reduce expression of the target gene. Similarly, the Silencer™ siRNA Cocktail Kit (RNase III) (catalog no. 1625, Ambion, Inc., Austin, Tex.) generates a mixture of siRNAs from dsRNA using RNase III instead of dicer. Like dicer, RNase III cleaves dsRNA into 12-30 bp dsRNA fragments with 2 to 3 nucleotide 3' overhangs, and 5'-phosphate and 3'-hydroxyl termini. According to the manufacturer, dsRNA is produced using T7 RNA polymerase, and reaction and purification components included in the kit. The dsRNA is then digested by RNase III to create a population of siRNAs. The kit includes reagents to synthesize long dsRNAs by in vitro transcription and to digest those dsRNAs into siRNA-like molecules using RNase III. The manufacturer indicates that the user need only supply a DNA template with opposing T7 phage polymerase promoters or two separate templates with promoters on opposite ends of the region to be transcribed.

The siRNAs can also be expressed from vectors. Typically, such vectors are administered in conjunction with a second vector encoding the corresponding complementary strand. Once expressed, the two strands anneal to each other and form the functional double stranded siRNA. One exemplar vector suitable for use is pSuper, available from OligoEngine, Inc. (Seattle, Wash.). In some embodiments, the vector contains two promoters, one positioned downstream of the first and in antiparallel orientation. The first promoter is transcribed in one direction, and the second in the direction antiparallel to the first, resulting in expression of the complementary strands. In yet another set of embodiments, the promoter is followed by a first segment encoding the first strand, and a second segment encoding the second strand. The second strand is complementary to the palindrome of the first strand. Between the first and the second strands is a section of RNA serving as a linker (sometimes called a "spacer") to permit the second strand to bend around and anneal to the first strand, in a configuration known as a "hairpin."

The formation of hairpin RNAs, including use of linker sections, is well known in the art. Typically, an siRNA expression cassette is employed, using a Polymerase III promoter such as human U6, mouse U6, or human H1. The coding sequence is typically a 19-nucleotide sense siRNA sequence linked to its reverse complementary antisense siRNA sequence by a short spacer. Nine-nucleotide spacers are typical, although other spacers can be designed. For example, the Ambion website indicates that its scientists have had success with the spacer TTCAAGAGA (SEQ ID NO:18). Further, 5-6 T's are often added to the 3' end of the oligonucleotide to serve as a termination site for Polymerase III. See also, Yu et al., Mol Ther 7(2):228-36 (2003); Matsukura et al., Nucleic Acids Res 31(15):e77 (2003).

As an example, the siRNA targets identified above can be targeted by hairpin siRNA as follows. To attack the same targets by short hairpin RNAs, produced by a vector (permanent RNAi effect), sense and antisense strand can be put in a row with a loop forming sequence in between and suitable sequences for an adequate expression vector to both ends of the sequence. The following are non-limiting examples of hairpin sequences that can be cloned into the pSuper vector:

1) Target:
(SEQ ID NO: 19)
CAGTGTTCATTGGCCATGACTGG

Sense strand:
(SEQ ID NO: 20)
5'-GATCCCCGTGTTCATTGGCCATGACTTTC

AAGAGAAGTCATGGCCAATGAACACTTTTT-3'

Antisense strand:
(SEQ ID NO: 21)
5'-AGCTAAAAAGTGTTCATTGGCCATGACTTC

TCTTGAAAGTCATGGCCAATGAACACGGG-3'

2) Target:
(SEQ ID NO: 22)
GAAAGGCTATGGAGAGTCATCTG

Sense strand:
(SEQ ID NO: 23)
5'-GATCCCCAAGGCTATGGAGAGTCATCTTCA

AGAGAGATGACTCTCCATAGCCTTTTTTT-3'

Antisense strand:
(SEQ ID NO: 24)
5'-AGCTAAAAAAAGGCTATGGAGAGTCATCTC

TCTTGAAGATGACTCTCCATAGCCTTGGG-3'

3) Target:
(SEQ ID NO: 25)
AAAGGCTATGGAGAGTCATCTGC

Sense strand:
(SEQ ID NO: 26)
5'-GATCCCCAGGCTATGGAGAGTCATCTTTC

AAGAGAAGATGACTCTCCATAGCCTTTTTT-3'

Antisense strand:
(SEQ ID NO: 27)
5'-AGCTAAAAAGGCTATGGAGAGTCATCATC

TCTTGAAAGATGACTCTCCATAGCCTGGG-3'

4) Target:
(SEQ ID NO: 28)
CAAGCAGTGTTCATTGGCCATGA

Sense strand:
(SEQ ID NO: 29)
5'-GATCCCCAGCAGTGTTCATTGGCCATTTC

AAGAGAATGGCCAATGAACACTGCTTTTTT-3'

Antisense strand:
(SEQ ID NO: 30)
5'-AGCTAAAAAAGCAGTGTTCATTGGCCATT

CTCTTGAAATGGCCAATGAACACTGCTGGG-3'

5) Target:
(SEQ ID NO: 31)
CAGCACATGGAGGACTGGATTCC

Sense strand
(SEQ ID NO: 32)
5'-GATCCCCGCACATGGAGGACTGGATTTTCA

AGAGAAATCCAGTCCTCCATGTGCTTTTT-3'

Antisense strand:
(SEQ ID NO: 33)
5'-AGCTAAAAAGCACATGGAGGACTGGATTTC

TCTTGAAAATCCAGTCCTCCATGTGCGGG-3'

In addition to siRNAs, other means are known in the art for inhibiting the expression of antisense molecules, ribozymes, and the like are well known to those of skill in the art. The nucleic acid molecule can be a DNA probe, a riboprobe, a peptide nucleic acid probe, a phosphorothioate probe, or a 2'-O methyl probe.

Generally, to assure specific hybridization, the antisense sequence is substantially complementary to the target sequence. In certain embodiments, the antisense sequence is exactly complementary to the target sequence. The antisense polynucleotides may also include, however, nucleotide substitutions, additions, deletions, transitions, transpositions, or modifications, or other nucleic acid sequences or non-nucleic acid moieties so long as specific binding to the relevant target sequence corresponding to the sEH gene is retained as a functional property of the polynucleotide. In one embodiment, the antisense molecules form a triple helix-containing, or "triplex" nucleic acid. Triple helix formation results in inhibition of gene expression by, for example, preventing transcription of the target gene (see, e.g., Cheng et al., 1988, J. Biol. Chem. 263:15110; Ferrin and Camerini-Otero, 1991, Science 354:1494; Ramdas et al., 1989, J. Biol. Chem. 264:17395; Strobel et al., 1991, Science 254:1639; and Rigas et al., 1986, Proc. Natl. Acad. Sci. U.S.A. 83:9591)

Antisense molecules can be designed by methods known in the art. For example, Integrated DNA Technologies (Coralville, Iowa) makes available a program found on the worldwide web "biotools.idtdna.com/antisense/AntiSense.aspx", which will provide appropriate antisense sequences for nucleic acid sequences up to 10,000 nucleotides in length. Using this program with the sEH gene provides the following exemplar sequences:

1)
(SEQ ID NO: 34)
UGUCCAGUGCCCACAGUCCU 2)
(SEQ ID NO: 35)
UUCCCACCUGACACGACUCU 3)
(SEQ ID NO: 36)
GUUCAGCCUCAGCCACUCCU 4)
(SEQ ID NO: 37)
AGUCCUCCCGCUUCACAGA 5)
(SEQ ID NO: 38)
GCCCACUUCCAGUUCCUUUCC

In another embodiment, ribozymes can be designed to cleave the mRNA at a desired position. (See, e.g., Cech, 1995, Biotechnology 13:323; and Edgington, 1992, Biotechnology 10:256 and Hu et al., PCT Publication WO 94/03596).

The antisense nucleic acids (DNA, RNA, modified, analogues, and the like) can be made using any suitable method for producing a nucleic acid, such as the chemical synthesis and recombinant methods disclosed herein and known to one of skill in the art. In one embodiment, for example, antisense RNA molecules may be prepared by de novo chemical synthesis or by cloning. For example, an antisense RNA can be made by inserting (ligating) a sEH gene sequence in reverse orientation operably linked to a promoter in a vector (e.g., plasmid). Provided that the promoter and, preferably termination and polyadenylation signals, are properly positioned, the strand of the inserted sequence corresponding to the noncoding strand are transcribed and act as an antisense oligonucleotide.

It are appreciated that the oligonucleotides can be made using nonstandard bases (e.g., other than adenine, cytidine, guanine, thymine, and uridine) or nonstandard backbone structures to provides desirable properties (e.g., increased nuclease-resistance, tighter-binding, stability or a desired Tm). Techniques for rendering oligonucleotides nuclease-resistant include those described in PCT Publication WO 94/12633. A wide variety of useful modified oligonucleotides may be produced, including oligonuclotides having a peptide-nucleic acid (PNA) backbone (Nielsen et al., 1991, Science 254:1497) or incorporating 2'-O-methyl ribonucleotides, phosphorothioate nucleotides, methyl phosphonate nucleotides, phosphotriester nucleotides, phosphorothioate nucleotides, phosphoramidates.

Proteins have been described that have the ability to translocate desired nucleic acids across a cell membrane. Typically, such proteins have amphiphilic or hydrophobic subsequences that have the ability to act as membrane-translocating carriers. For example, homeodomain proteins have the ability to translocate across cell membranes. The shortest internalizable peptide of a homeodomain protein, Antennapedia, was found to be the third helix of the protein, from amino acid position 43 to 58 (see, e.g., Prochiantz, Current Opinion in Neurobiology 6:629-634 (1996). Another subsequence, the h (hydrophobic) domain of signal peptides, was found to have similar cell membrane translocation characteristics (see, e.g., Lin et al., J. Biol. Chem. 270:14255-14258 (1995)). Such subsequences can be used to translocate oligonucleotides across a cell membrane. Oligonucleotides can be conveniently derivatized with such sequences. For example, a linker can be used to link the oligonucleotides and the translocation sequence. Any suitable linker can be used, e.g., a peptide linker or any other suitable chemical linker.

More recently, it has been discovered that siRNAs can be introduced into mammals without eliciting an immune response by encapsulating them in nanoparticles of cyclodextrin. Information on this method can be found on the worldwide web at "nature.com/news/2005/050418/full/050418-6.html."

In another method, the nucleic acid is introduced directly into superficial layers of the skin or into muscle cells by a jet of compressed gas or the like. Methods for administering naked polynucleotides are well known and are taught, for example, in U.S. Pat. No. 5,830,877 and International Publication Nos. WO 99/52483 and WO 94/21797. Devices for accelerating particles into body tissues using compressed gases are described in, for example, U.S. Pat. Nos. 6,592,545, 6,475,181, and 6,328,714. The nucleic acid may be lyophilized and may be complexed, for example, with polysaccharides to form a particle of appropriate size and mass for acceleration into tissue. Conveniently, the nucleic acid can be placed on a gold bead or other particle which provides suitable mass or other characteristics. Use of gold beads to carry nucleic acids into body tissues is taught in, for example, U.S. Pat. Nos. 4,945,050 and 6,194,389.

The nucleic acid can also be introduced into the body in a virus modified to serve as a vehicle without causing pathogenicity. The virus can be, for example, adenovirus, fowlpox virus or vaccinia virus.

miRNAs and siRNAs differ in several ways: miRNA derive from points in the genome different from previously recognized genes, while siRNAs derive from mRNA, viruses or transposons, miRNA derives from hairpin structures, while siRNA derives from longer duplexed RNA, miRNA is conserved among related organisms, while siRNA usually is not, and miRNA silences loci other than that from which it derives, while siRNA silences the loci from which it arises. Interestingly, miRNAs tend not to exhibit perfect complementarity to the mRNA whose expression they inhibit. See, McManus et al., supra. See also, Cheng et al., Nucleic Acids Res. 33(4):1290-7 (2005); Robins and Padgett, Proc Natl Acad Sci USA. 102(11): 4006-9 (2005); Brennecke et al., PLoS Biol. 3(3):e85 (2005). Methods of designing miRNAs are known. See, e.g., Zeng et al., Methods Enzymol. 392:371-80 (2005); Krol et al., J Biol Chem. 279(40):42230-9 (2004); Ying and Lin, Biochem Biophys Res Commun. 326(3):515-20 (2005).

In some embodiments, the endogenous polynucleotide encoding sEH in the subject can be rendered non-functional or non-expressing, e.g., by employing gene therapy methodologies. This can be accomplished using any method known in the art, including the working embodiment described herein. In some embodiments, the endogenous gene encoding sEH in the subject is rendered non-functional or non-expressing in certain desired tissues, e.g., in renal tissue or more specifically in podocyte cells, as demonstrated herein. In some embodiments, the endogenous gene encoding sEH in the subject is rendered non-functional or non-expressing by employing homologous recombination, mutating, replacing or eliminating the functional or expressing gene encoding sEH. Illustrative methods are known in the art and described, e.g., in Flynn, et al., Exp Hematol. (2015) Jun. 19. pii: S0301-472X(15)00207-6 (using CRISPR); Truong, et al, Nucleic Acids Res. (2015) Jun. 16. pii: gkv601 (using split-Cas9); Yang, Mil Med Res. (2015) May 9; 2:11 (using CRISPR-Cas9); and Imai, et al., Intern Med. (2004) February; 43(2):85-96.

f. Epoxy-Fatty Acids

In some embodiments, an epoxy-fatty acid is administered as an agent that increases epoxy-fatty acids. Illustrative epoxy-fatty acids include epoxides of linoleic acid, eicosapentaenoic acid ("EPA") and docosahexaenoic acid ("DHA").

The fatty acids eicosapentaenoic acid ("EPA") and docosahexaenoic acid ("DHA") have recently become recognized as having beneficial effects, and fish oil tablets, which are a good source of these fatty acids, are widely sold as supplements. In 2003, it was reported that these fatty acids reduced pain and inflammation. Sethi, S. et al., Blood 100: 1340-1346 (2002). The paper did not identify the mechanism of action, nor the agents responsible for this relief.

Cytochrome P450 ("CYP450") metabolism produces cis-epoxydocosapentaenoic acids ("EpDPEs") and cis-epoxyeicosatetraenoic acids ("EpETEs") from docosahexaenoic acid ("DHA") and eicosapentaenoic acid ("EPA"), respectively. These epoxides are known endothelium-derived hyperpolarizing factors ("EDHFs"). These EDHFs, and others yet unidentified, are mediators released from vascular endothelial cells in response to acetylcholine and bradykinin, and are distinct from the NOS- (nitric oxide) and COX-derived (prostacyclin) vasodilators. Overall cytochrome P450 (CYP450) metabolism of polyunsaturated fatty acids produces epoxides, such as EETs, which are prime candidates for the active mediator(s). 14(15)-EpETE, for example, is derived via epoxidation of the 14,15-double bond of EPA and is the $\omega$-3 homolog of 14(15)-EpETrE ("14(15)EET") derived via epoxidation of the 14,15-double bond of arachidonic acid.

As mentioned, it is beneficial to elevate the levels of EETs, which are epoxides of the fatty acid arachidonic acid. Our studies of the effects of EETs has led us to realization that the anti-inflammatory effect of EPA and DHA are likely due to increasing the levels of the epoxides of these two fatty acids. Thus, increasing the levels of epoxides of EPA, of DHA, or of both, will act to reduce, mitigate, ameliorate, improve symptoms associated with a neuropsychiatric illness characterized by depressive symptoms, in mammals in need thereof. This beneficial effect of the epoxides of these fatty acids has not been previously recognized. Moreover, these epoxides have not previously been administered as agents, in part because, as noted above, epoxides have generally been considered too labile to be administered.

Like EETs, the epoxides of EPA and DHA are substrates for sEH. The epoxides of EPA and DHA are produced in the body at low levels by the action of cytochrome P450s. Endogenous levels of these epoxides can be maintained or increased by the administration of sEHI. However, the endogenous production of these epoxides is low and usually occurs in relatively special circumstances, such as the resolution of inflammation. Our expectation is that administering these epoxides from exogenous sources will aid in the resolution of symptoms of neuropsychiatric illnesses characterized by depressive symptoms. It is further beneficial with pain or inflammation to inhibit sEH with sEHI to reduce hydrolysis of these epoxides, thereby maintaining them at relatively high levels.

EPA has five unsaturated bonds, and thus five positions at which epoxides can be formed while DHA has six. The epoxides of EPA are typically abbreviated and referred to generically as "EpETEs", while the epoxides of DHA are typically abbreviated and referred to generically as "EpDPEs". The specific regioisomers of the epoxides of each fatty acid are set forth in the following Table 6:

TABLE 6

Regioisomers of Eicosapentaenoic acid ("EPA") epoxides:

1. Formal name: (±)5(6)-epoxy-8Z, 11Z, 14Z, 17Z-eicosatetraenoic acid,
Synonym 5(6)-epoxy Eicosatetraenoic acid
Abbreviation 5(6)-EpETE
2. Formal name: (±)8(9)-epoxy-5Z, 11Z, 14Z, 17Z-eicosatetraenoic acid,
Synonym 8(9)-epoxy Eicosatetraenoic acid
Abbreviation 8(9)-EpETE
3. Formal name: (±)11(12)-epoxy-5Z, 8Z, 14Z, 17Z-eicosatetraenoic acid,
Synonym 11(12)-epoxy Eicosatetraenoic acid
Abbreviation 11(12)-EpETE
4. Formal name: (±)14(15)-epoxy-5Z, 8Z, 11Z, 17Z-eicosatetraenoic acid,
Synonym 14(15)-epoxy Eicosatetraenoic acid
Abbreviation 14(15)-EpETE
5. Formal name: (±)17(18)-epoxy-5Z, 8Z, 11Z, 14Z-eicosatetraenoic acid,
Synonym 17(18)-epoxy Eicosatetraenoic acid
Abbreviation 17(18)-EpETE

Regioisomers of Docosahexaenoic acid ("DHA") epoxides:

1. Formal name: (±) 4(5)-epoxy-7Z, 10Z, 13Z, 16Z, 19Z-docosapentaenoic acid,
Synonym 4(5)-epoxy Docosapentaenoic acid
Abbreviation 4(5)-EpDPE
2. Formal name: (±) 7(8)-epoxy-4Z, 10Z, 13Z, 16Z, 19Z-docosapentaenoic acid,
Synonym 7(8)-epoxy Docosapentaenoic acid
Abbreviation 7(8)-EpDPE
3. Formal name: (±)10(11)-epoxy-4Z, 7Z, 13Z, 16Z, 19Z-docosapentaenoic acid,
Synonym 10(11)-epoxy Docosapentaenoic acid
Abbreviation 10(11)-EpDPE
4. Formal name: (±)13(14)-epoxy-4Z, 7Z, 10Z, 16Z, 19Z-docosapentaenoic acid,
Synonym 13(14)-epoxy Docosapentaenoic acid
Abbreviation 13(14)-EpDPE
5. Formal name: (±) 16(17)-epoxy-4Z, 7Z, 10Z, 13Z, 19Z-docosapentaenoic acid,
Synonym 16(17)-epoxy Docosapentaenoic acid
Abbreviation 16(17)-EpDPE
6. Formal name: (±) 19(20)-epoxy-4Z, 7Z, 10Z, 13Z, 16Z-docosapentaenoic acid,
Synonym 19(20)-epoxy Docosapentaenoic acid
Abbreviation 19(20)-EpDPE Any of these epoxides, or combinations of any of these, can be exposed to the stem cells in vitro or co-administered in vivo in the compositions and methods.

6. Formulation and Administration

In various embodiments of the compositions, the agent that increases epoxy fatty acids (EpFA) (e.g., an inhibitor of sEH, an EET, an epoxy fatty acid, and mixtures thereof) is co-administered with the population of stem cells. In some embodiments, the agent that increases epoxy fatty acids (EpFA) comprises an epoxide of EPA, an epoxide of DHA, or epoxides of both, and an sEHI.

The agent that increases epoxy fatty acids (EpFA) can be prepared and administered in a wide variety of oral, parenteral and topical dosage forms. In some embodiments, the agent that increases epoxy fatty acids (EpFA) can be administered orally, by injection, that is, intravenously, intramuscularly, intracutaneously, subcutaneously, intraduodenally, or intraperitoneally. The agent that increases epoxy fatty acids (EpFA) can also be administered by inhalation, for example, intranasally. Additionally, the agent that increases epoxy fatty acids (EpFA) can be administered transdermally. Accordingly, in some embodiments, the methods contemplate administration of compositions comprising a pharmaceutically acceptable carrier or excipient, an agent that increases epoxy fatty acids (EpFA) (e.g., an sEHI or a pharmaceutically acceptable salt of the inhibitor and, optionally, one or more EETs or epoxides of EPA or of DHA, or of both), and optionally an anti-inflammatory agent. In some embodiments, the methods comprise administration of an sEHI and one or more epoxides of EPA or of DHA, or of both.

For preparing the pharmaceutical compositions, the pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component. In tablets, the active component is mixed with the carrier having the necessary binding properties in suitable proportions and compacted in the shape and size desired. The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution. Transdermal administration can be performed using suitable carriers. If desired, apparatuses designed to facilitate transdermal delivery can be employed. Suitable carriers and apparatuses are well known in the art, as exemplified by U.S. Pat. Nos. 6,635,274, 6,623,457, 6,562,004, and 6,274,166.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active components in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

A variety of solid, semisolid and liquid vehicles have been known in the art for years for topical application of agents to the skin. Such vehicles include creams, lotions, gels, balms, oils, ointments and sprays. See, e.g., Provost C. "Transparent oil-water gels: a review," Int J Cosmet Sci. 8:233-247 (1986), Katz and Poulsen, Concepts in biochemical pharmacology, part I. In: Brodie B B, Gilette J R, eds. Handbook of Experimental Pharmacology. Vol. 28. New York, N.Y.: Springer; 107-174 (1971), and Hadgcraft, "Recent progress in the formulation of vehicles for topical applications," Br J Dermatol., 81:386-389 (1972). A number of topical formulations of analgesics, including capsaicin (e.g., Capsin®), so-called "counter-irritants" (e.g., Icy-Hot®, substances such as menthol, oil of wintergreen, camphor, or eucalyptus oil compounds which, when applied to skin over an area presumably alter or off-set pain in joints or muscles served by the same nerves) and salicylates (e.g. BenGay®), are known and can be readily adapted for topical administration of sEHI by replacing the active ingredient or ingredient with an sEHI, with or without EETs. It is presumed that the person of skill is familiar with these various vehicles and preparations and they need not be described in detail herein.

The agent that increases epoxy fatty acids (EpFA) (e.g., an inhibitor of sEH, an EET, an epoxy fatty acid, and mixtures thereof), optionally mixed with an anti-inflammatory and/or analgesic agent, can be mixed into such modalities (creams, lotions, gels, etc.) for topical administration. In general, the concentration of the agents provides a gradient which drives the agent into the skin. Standard ways of determining flux of drugs into the skin, as well as for modifying agents to speed or slow their delivery into the skin are well known in the art and taught, for example, in Osborne and Amann, eds., Topical Drug Delivery Formulations, Marcel Dekker, 1989. The use of dermal drug delivery agents in particular is taught in, for example, Ghosh et al., eds., Transdermal and Topical Drug Delivery Systems, CRC Press, (Boca Raton, Fla., 1997).

In some embodiments, the agents are in a cream. Typically, the cream comprises one or more hydrophobic lipids, with other agents to improve the "feel" of the cream or to provide other useful characteristics. In one embodiment, for example, a cream may contain 0.01 mg to 10 mg of sEHI, with or without one or more EETs, per gram of cream in a white to off-white, opaque cream base of purified water USP, white petrolatum USP, stearyl alcohol NF, propylene glycol USP, polysorbate 60 NF, cetyl alcohol NF, and benzoic acid USP 0.2% as a preservative. In various embodiments, sEHI can be mixed into a commercially available cream, Vanicream® (Pharmaceutical Specialties, Inc., Rochester, Minn.) comprising purified water, white petrolatum, cetearyl alcohol and ceteareth-20, sorbitol solution, propylene glycol, simethicone, glyceryl monostearate, polyethylene glycol monostearate, sorbic acid and BHT.

In other embodiments, the agent or agents are in a lotion. Typical lotions comprise, for example, water, mineral oil, petrolatum, sorbitol solution, stearic acid, lanolin, lanolin alcohol, cetyl alcohol, glyceryl stearate/PEG-100 stearate, triethanolamine, dimethicone, propylene glycol, microcrystalline wax, tri (PPG-3 myristyl ether) citrate, disodium EDTA, methylparaben, ethylparaben, propylparaben, xanthan gum, butylparaben, and methyldibromo glutaronitrile.

In some embodiments, the agent is, or agents are, in an oil, such as jojoba oil. In some embodiments, the agent is, or agents are, in an ointment, which may, for example, white petrolatum, hydrophilic petrolatum, anhydrous lanolin, hydrous lanolin, or polyethylene glycol. In some embodiments, the agent is, or agents are, in a spray, which typically comprise an alcohol and a propellant. If absorption through the skin needs to be enhanced, the spray may optionally contain, for example, isopropyl myristate.

Whatever the form in which the agents that inhibit sEH are topically administered (that is, whether by solid, liquid, lotion, gel, spray, etc.), in various embodiments they are administered at a dosage of about 0.01 mg to 10 mg per 10 $cm^2$. An exemplary dose for systemic administration of an inhibitor of sEH is from about 0.001 μg/kg to about 100 mg/kg body weight of the mammal. In various embodiments, dose and frequency of administration of an sEH inhibitor are selected to produce plasma concentrations within the range of 2.5 μM and 30 nM.

The agent that increases epoxy fatty acids (EpFA) (e.g., an inhibitor of sEH, an EET, an epoxy fatty acid, and mixtures thereof), optionally mixed with an anti-inflammatory and/or analgesic agent, can be introduced into the bowel by use of a suppository. As is known in the art, suppositories are solid compositions of various sizes and shapes intended for introduction into body cavities. Typically, the suppository comprises a medication, which is released into the immediate area from the suppository. Typically, suppositories are made using a fatty base, such as cocoa butter, that melts at body temperature, or a water-soluble or miscible base, such as glycerinated gelatin or polyethylene glycol.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The term "unit dosage form", as used in the specification, refers to physically discrete units suitable as unitary dosages for human subjects and animals, each unit containing a predetermined quantity of active material calculated to produce the desired pharmaceutical effect in association with the required pharmaceutical diluent, carrier or vehicle. The specifications for the novel unit dosage forms are dependent on (a) the unique characteristics of the active material and the particular effect to be achieved and (b) the limitations inherent in the art of compounding such an active material for use in humans and animals, as disclosed in detail in this specification.

A therapeutically effective amount or a sub-therapeutic amount of the agent that increases epoxy fatty acids (EpFA) can be co-administered with a population of stem cells. The dosage of the specific compounds depends on many factors that are well known to those skilled in the art. They include for example, the route of administration and the potency of the particular compound. An exemplary dose is from about 0.001 μg/kg to about 100 mg/kg body weight of the mammal. Determination of an effective amount is well within the capability of those skilled in the art, especially in light of the detailed disclosure provided herein. Generally, an efficacious or effective amount of a combination of one or more active agents are determined by first administering a low dose or small amount of a polypeptide or composition and then incrementally increasing the administered dose or dosages, adding a second or third medication as needed, until a desired effect of is observed in the treated subject with minimal or no toxic side effects. Applicable methods for determining an appropriate dose and dosing schedule for administration of the herein described active agents are described, for example, in *Goodman and Gilman's The Pharmacological Basis of Therapeutics,* 12th Edition, 2010, McGraw-Hill Professional; in a Physicians' Desk Reference (PDR), 71st Edition, 2017, PDR Network; in *Remington: The Science and Practice of Pharmacy,* $21^{st}$ Ed., 2005, supra; and in *Martindale: The Complete Drug Reference,*

Sweetman, 2005, London: Pharmaceutical Press., and in Martindale, *Martindale: The Extra Pharmacopoeia*, 31st Edition., 1996, Amer Pharmaceutical Assn, each of which are hereby incorporated herein by reference.

EETs, EpDPEs, or EpETEs are unstable, and can be converted to the corresponding diols, in acidic conditions, such as those in the stomach. To avoid this, EETs, EpDPEs, or EpETEs can be administered intravenously or by injection. EETs, EpDPEs, or EpETEs intended for oral administration can be encapsulated in a coating that protects the compounds during passage through the stomach. For example, the EETs, EpDPEs, or EpETEs can be provided with a so-called "enteric" coating, such as those used for some brands of aspirin, or embedded in a formulation. Such enteric coatings and formulations are well known in the art. In some formulations, the compositions are embedded in a slow-release formulation to facilitate administration of the agents over time.

It is understood that, like all drugs, sEHIs have half-lives defined by the rate at which they are metabolized by or excreted from the body, and that the sEHIs will have a period following administration during which they are present in amounts sufficient to be effective. If EETs, EpDPEs, or EpETEs are administered after the sEHI is administered, therefore, it is desirable that the EETs, EpDPEs, or EpETEs be administered during the period during which the sEHI are present in amounts to be effective in delaying hydrolysis of the EETs, EpDPEs, or EpETEs. Typically, the EETs, EpDPEs, or EpETEs are administered within 48 hours of administering an sEH inhibitor. Preferably, the EETs, EpDPEs, or EpETEs are administered within 24 hours of the sEHI, and even more preferably within 12 hours. In increasing order of desirability, the EETs, EpDPEs, or EpETEs are administered within 10, 8, 6, 4, 2, hours, 1 hour, or one half hour after administration of the inhibitor. When co-administered, the EETs, EpDPEs, or EpETEs are preferably administered concurrently with the sEHI.

7. Methods of Monitoring

Clinical efficacy can be monitored using any method known in the art. Measurable parameters to monitor efficacy will depend on the condition being treated. For monitoring the status or improvement of one or more symptoms associated with cardiomyopathy, measurable parameters can include without limitation, auditory inspection (e.g., using a stethoscope), blood pressure, electrocardiogram (EKG), magnetic resonance imaging (MRI), changes in blood markers, and behavioral changes in the subject (e.g., appetite, the ability to eat solid foods, grooming, sociability, energy levels, increased activity levels, weight gain, exhibition of increased comfort). These parameters can be measured using any methods known in the art. In some embodiments, the different parameters can be assigned a score. Further, the scores of two or more parameters can be combined to provide an index for the subject.

Observation of the stabilization, improvement and/or reversal of one or more symptoms or parameters by a measurable amount indicates that the treatment or prevention regime is efficacious. Observation of the progression, increase or exacerbation of one or more symptoms indicates that the treatment or prevention regime is not efficacious. For example, in the case of cardiomyopathy, observation of the improvement of cardiac function (e.g., blood pressure in appropriate range, stable heart rhythm or reduction or absence of arrhythmias, changes in blood markers, and/or behavioral changes in the subject (e.g., increased appetite, the ability to eat solid foods, improved/increased grooming, improved/increased sociability, increased energy levels, improved/increased activity levels, weight gain and/or stabilization, exhibition of increased comfort) after one or more co-administrations of stem cells with an agent indicates that the treatment or prevention regime is efficacious. Likewise, observation of reduction or decline of cardiac function (e.g., blood pressure in appropriate range, unstable heart rhythm or continued presence or increased arrhythmias, changes in blood markers, and/or behavioral changes in the subject (e.g., decreased appetite, the inability to eat solid foods, decreased grooming, decreased sociability, decreased energy levels, decreased activity levels, weight loss, exhibition of increased discomfort) after one or more co-administrations of stem cells with an agent indicates that the treatment or prevention regime is not efficacious.

In certain embodiments, the monitoring methods can entail determining a baseline value of a measurable biomarker or disease parameter in a subject before administering a dosage of the one or more active agents described herein, and comparing this with a value for the same measurable biomarker or parameter after a course of treatment.

In other methods, a control value (i.e., a mean and standard deviation) of the measurable biomarker or parameter is determined for a control population. In certain embodiments, the individuals in the control population have not received prior treatment and do not have the disease condition subject to treatment (e.g., cardiomyopathy), nor are at risk of developing the disease condition subject to treatment (e.g., cardiomyopathy). In such cases, if the value of the measurable biomarker or clinical parameter approaches the control value, then treatment is considered efficacious. In other embodiments, the individuals in the control population have not received prior treatment and have been diagnosed with the disease condition subject to treatment (e.g., cardiomyopathy). In such cases, if the value of the measurable biomarker or clinical parameter approaches the control value, then treatment is considered inefficacious.

In other methods, a subject who is not presently receiving treatment but has undergone a previous course of treatment is monitored for one or more of the biomarkers or clinical parameters to determine whether a resumption of treatment is required. The measured value of one or more of the biomarkers or clinical parameters in the subject can be compared with a value previously achieved in the subject after a previous course of treatment. Alternatively, the value measured in the subject can be compared with a control value (mean plus standard deviation) determined in population of subjects after undergoing a course of treatment. Alternatively, the measured value in the subject can be compared with a control value in populations of prophylactically treated subjects who remain free of symptoms of disease, or populations of therapeutically treated subjects who show amelioration of disease characteristics. In such cases, if the value of the measurable biomarker or clinical parameter approaches the control value, then treatment is considered efficacious and need not be resumed. In all of these cases, a significant difference relative to the control level (i.e., more than a standard deviation) is an indicator that treatment should be resumed in the subject.

8. Kits

Further provided are kits, stents and patches comprising a population of stem cells and one or more agents that increase the production or levels of EETs. Embodiments of the stem cells and one or more agents that increase the production or levels of EETs are as described above and herein. In some embodiments, the stem cells are provided in an appropriate container, e.g., a vial, a tube, a pouch, a bag. Stem cell coated or loaded stents are known in the art and find use, e.g., in the methods and kits, e.g., as described in Raina, et al., *Heart.* 2014 June; 100(Suppl 3):A88-A89; Savchenko, et al., *Vestn Rentgenol Radiol.* 2013 July-August; (4):41-6; Wang, et al., *Cardiovasc Res.* 2009 Dec. 1; 84(3):461-9; Motwani, et al., *Biotechnol Appl Biochem.* 2011 January-February; 58(1):2-13; Wu, et al., *J Biomed Mater Res A.* 2011 Sep. 1; 98(3):442-9; and Intl. Patent Publ. No. WO 2008/094936. Patches, including cardiac patches, which can serve as repositories for the delivery of stem cells are also known in the art and find use, e.g., in the methods and kits, e.g., as described in Kim, et al., Integr Biol (Camb). 2012 September; 4(9):1019-33; LeBlanc, et al., *Stem Cells Transl Med.* 2013 November; 2(11):896-905; Lam, et al., *Tissue Eng* Part A. 2013 March; 19(5-6):738-47; Wang, et al., Antioxid Redox Signal. 2014 Apr. 30; Wickham, et al, *J Biomed Mater Res B Appl Biomater.* 2014 Mar. 24; and Martinez-Ramos, et al., *Tissue Eng Part C Methods.* 2014 Mar. 14.

EXAMPLES

The following examples are offered to illustrate, but not to limit the claimed invention.

Example 1

Treatment with Soluble Epoxide Hydrolase Inhibitors Enhances Cardiac Cell-Based Therapy In this example, we investigated whether the survival of transplanted cells in the injured myocardium can be improved by reducing the inflammation to confer functional recovery in a mouse myocardial infarction (MI) model. This example demonstrates the beneficial effects of an inhibitor of the sEH enzyme (1-trifluoromethoxyphenyl-3-(1-propionylpiperidine-4-yl)urea or TPPU) in cell-based therapy using human induced pluripotent stem cell-derived cardiomyocytes (hiPSC-CMs) in a murine post-myocardial infarction (MI) model.

Methods

The investigation conforms to the Guide for the Care and Use of Laboratory Animals published by the US National Institutes of Health (NIH Publication No. 85-23, revised 1996) and was approved by the University of California, Davis Institutional Animal Care and Use Committee.

Figure 2:
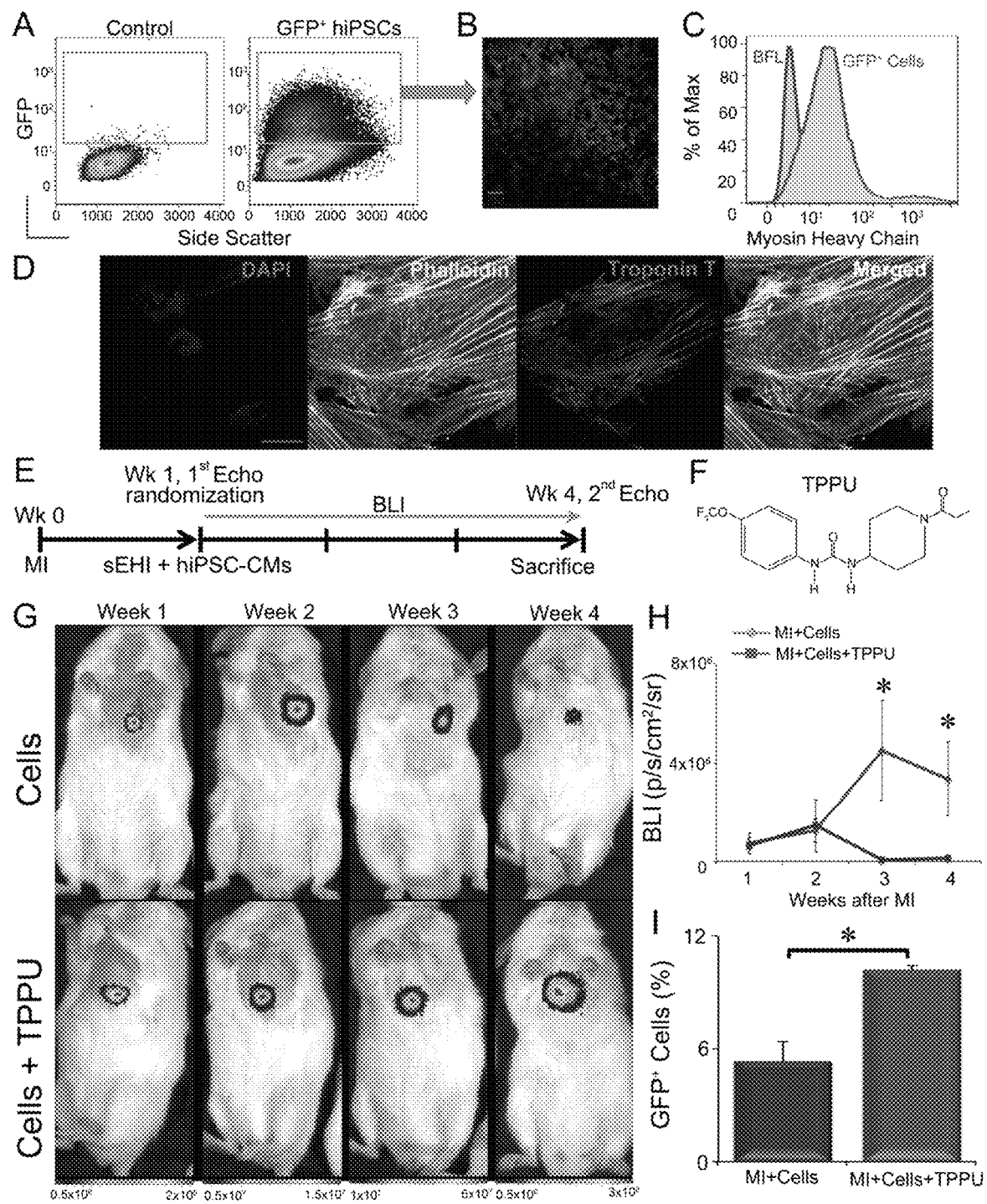
FIGS. 2A-I illustrate Figure. 1. TPPU improves hiPSC-CMs retention in a murine myocardial infarction (MI) model: (A) Fluorescent activated cell sorting (FACS) for hiPSCs transduced with luciferase and GFP. (B) Confocal images of cultured FAC sorted GFP+ hiPSCs. Scale bar=50 µM. (C) Representative myosin heavy chain expression of hiPSC-CMs at day 25 after differentiation assessed by flow cytometry. (D) Confocal images for expression of phalloidin (green) and troponin T (red) in hiPSC-CM with cell nuclei stained with DAPI (blue). Scale bar=20 µM. (E) Schematic representation of the experimental protocol, Wk=week, BLI=bioluminescence imaging. (F) Structure of the sEHI, 1-trifluoromethoxyphenyl-3-(1-propionylpiperidine-4-yl) urea (TPPU) used in our studies. Mice were treated with TPPU (15 mg/L) orally in drinking water starting one week after MI and for 3 weeks. (G) Longitudinal in vivo BLI of hiPSC-CMs transplanted into NSG mice at Week 1, 2, 3 and 4 with (bottom panel) and without (top panel) sEHI treatment. (H) Quantification of BLI signal from E. (I) Flow cytometric analysis of GFP+ hiPSC-CMs after 4 weeks of sEHI treatment. Cells=hiPSC-CMs. Mean±SEM, n=8 animals per group and *P<0.05 by ANOVA.

Soluble epoxide hydrolase inhibitor (sEHI). Selective and potent inhibitors (low nanomolar Ki's) for the rodent and human soluble epoxide hydrolase enzyme (sEH) were developed based on the catalytic mechanism and the X-ray structure of the murine sEH (PDB access #: 1CQZ & 1CR6) (47-49). The potency, pharmacokinetics, and physiochemical properties of 11 different sEHIs were conducted. 1-Trifluoromethoxyphenyl-3-(1-propionylpiperidine-4-yl)urea (TPPU, containing a piperidine ring, FIG. 2A) was found to have high inhibitory potency, drug-like physicochemical properties, pharmacokinetics with high area under the curve values, a relatively longer half-life and lower plasma protein binding properties than many previous compounds (50). For these pharmacokinetic favorable characteristics, TPPU was chosen for this study. TPPU was found to be a low nanomolar inhibitor of the sEH enzyme and was previously tested against commercial drug targets and the NIH screen of drug targets, there were no hits at 10 micromolar (over 1,000 fold higher concentration than the effective concentration for the sEH enzyme). In addition, the X-ray crystal structure of the sEH enzyme and the inhibitors has been solved (41-46, 51, 52). There is no evidence to date of off-target binding sites.

Myocardial infarction (MI) model in mice. MI was generated in 8- to 12-week-old NOD SCID gamma (NSG) as previously described (19). Briefly, animals were anesthetized with ketamine 50 mg/kg and xylazine 2.5 mg/kg intraperitoneally. Intubation was performed perorally and mechanical ventilation was initiated. MI was performed using ligation of the left anterior descending coronary artery (LAD) for 45 minutes. The chest was closed with 3-0 Dexon rib sutures, 5-0 Dexon II muscle sutures and buried skin sutures. Negative plural pressure was re-established via a temporary chest tube until spontaneous breathing occurred. Sham-operated animals underwent the same procedure without tying the suture.

Echocardiograms using Vevo 2100 (FUJIFILM, Toronto, Canada) were performed 1 week after surgery after which mice were randomized into six different groups: Sham±sEHI, MI±sEHI, and MI+hiPSC-CM=sEHI. Treatment with sEHI included TPPU (15 mg/L) given in the drinking water for a period of 3 weeks (53). The animals were followed for a period of three weeks at which time repeat echocardiograms were performed.

Magnetic Resonance Imaging (MRI). Imaging was performed using a Bruker BioSpec 7T horizontal bore system designed specifically for small animal imaging (Bruker Corporation, Billerica, Mass.). Mice were anesthetized with 1.5% isoflurane with oxygen in an induction chamber, placed in the MRI scanner and were fitted with a nose cone connected to a vaporizer. Physiological parameters such as respiration and body temperature were monitored with a physiological monitoring unit that provides feedback on a warm air blower to keep the animal at normal body temperature during the scan. A retrospective gating technique to produce snapshots of the heart cycle was used and the data were collected using ParaVision 5.1 software (Bruker Corporation) and analyzed using Amira 6.0 software (Thermo Fisher Scientific, Waltham, Mass.).

Hemodynamic Monitoring. Mice were anesthetized by intraperitoneal injection of 80 mg/kg of ketamine and 5 mg/kg of xylazine and maintained at 37° C. Recording of pressure and volume was performed by using Millar Pressure-Volume System MPVS-300 (Millar, Inc, Houston, Tex.), Power Lab, and Lab Chart 6.0 software (AD Instruments, Colorado Springs, Colo.).

Bioluminescence Imaging (BLI). Serial BLI was performed on hiPSC-CMs transplanted and TPPU treated mice on week 1, 2, 3, and 4 post MI with the use of the IVIS Spectrum (Perkin Elmer, Waltham, Mass.) imaging system using a thermoeletrically cooled back-thinned, back-illuminated CCD camera, with a 2048×2048 array of 13.5 micropixels and a 16-bit digitizer. Mice were anesthetized with isoflurane and were injected intraperitoneally with D-Luciferin (375 mg/kg body weight). Peak signals from a fixed region of interest were obtained and signals were quantified (photons.s-1.cm-2.sr-1) (21).

Human-induced pluripotent stem cell-derived cardiomyocytes (hiPSC-CM). HiPSCs (19-9-7T, WiCell, Madison, Wis.) were transduced with the puromycin gene under the α-myosin heavy chain (MHC) promoter to enable enrichment of cardiomyocytes post-differentiation and a double fusion construct of reporter genes; firefly luciferase (Flue)

for bioluminescence imaging and enhanced green fluorescent protein (GFP) to enable in vivo tracking of cell engraftment longitudinally (21). HiPSC were plated and differentiated for 30 days using a directed differentiation protocol (54). HiPSC-CMs enriched with puromycin and treated with tumor necrosis factor-α (TNF-α, 20 ng/ml for 20 minutes) or angiotensin II (ANG II, Sigma-Aldrich, 1 µM for 24 hours) with or without TPPU (1 µM) were fixed and stained with anti-myosin light chain-2a (MLC2a), anti-myosin light chain-2v (MLC2v) and anti-pERK1/2 antibodies (Cell Signaling Technology, Danvers, Mass.) before flow cytometric analyses as described above.

Soluble epoxide hydrolase inhibitor, myocardial infarction model in mice, optical and patch-clamp recordings of action potentials and K+ currents from hiPSC-CMs, histological analyses, immunofluorescence confocal scanning microscopy, flow cytometric analyses, and statistical analyses can be found in SI Materials and Methods.

Statistical Analysis. Data are presented as mean±S.E.M. Statistical comparisons were analyzed by one-way ANOVA followed by Bonferroni tests and Tukey's-Kramer honest significant difference analyses for post hoc comparison. Statistical significance was considered to be achieved when $p<0.05$.

Results

Figure 3:
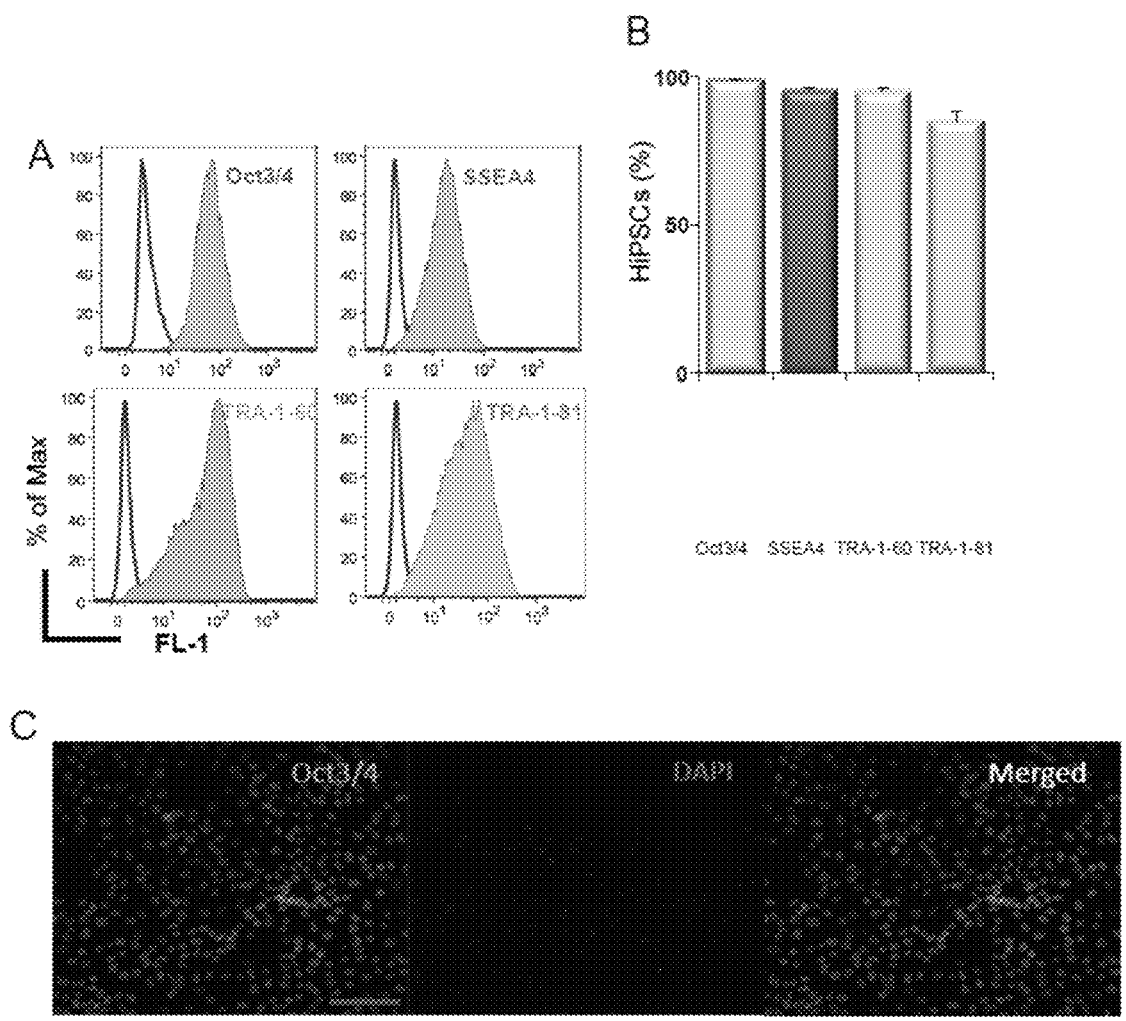
FIGS. 3A-C illustrate expression of pluripotent markers in hiPSCs. (A, B) Transduced hiPSCs revealed high protein expression levels of pluripotency markers such as Oct3/4, SSEA4, TRA-1-60 and TRA-1-81 as assessed by flow cytometry. (C) Immunofluorescence confocal laser scanning microscopic images of hiPSCs stained positive for pluripotency marker Oct3/4. DAPI (4', 6-diamidino-2-phenylindole) was used to stain the nuclei. Scale bar=100 µM.

Generation and characterization of hiPSC-CMs for cell transplantation. HiPSCs (19-9-7T, WiCell, Madison, Wis.) were transduced with the puromycin gene under the α-myosin heavy chain promoter to enable enrichment of cardiomyocytes post-differentiation and a double fusion construct of reporter genes (a kind gift from Dr. Joseph Wu, Stanford University); firefly luciferase (Fluc) for bioluminescence imaging and enhanced green fluorescent protein (GFP) to enable in vivo tracking of cell engraftment longitudinally (21). Transduced hiPSCs revealed high protein expression levels of pluripotency markers such as Oct3/4, SSEA4, TRA-1-60 and TRA-1-81 as assessed by flow cytometry (FIGS. 3A and 3B) and stained positive for pluripotency marker Oct4 when assessed by confocal immunofluorescence microscopy (FIG. 3C). Positive selection of GFP+ hiPSCs was achieved by sorting the cells using florescent activated cell sorter (FACS, FIGS. 2A and 2B). Next, GFP+ hiPSCs were differentiated into beating clusters of hiPSC-CMs using the small-molecule based protocol and enriched with puromycin treatment with ~76% myosin heavy chain positive cells as assessed by flow cytometry (FIG. 2C) (22). Immunostaining of hiPSC-CMs revealed the expression of troponin T (FIG. 2D). The use of these cells for transplantation and in vivo imaging was validated in vitro by the stable Fluc activity with a strong correlation between Fluc activity and cell number ($R2=0.985$; FIGS. 4A and 4B).

MI was generated in 8-12-week-old NOD-scid gamma (NSG, Institute of Regenerative Cures, UC Davis) using previously described techniques (FIG. 2E) (19). One week after the surgery, mice were randomized into six different groups: Sham±sEHI, MI±sEHI, and MI+hiPSC-CM±sEHI. Transplantation of $1.5 \times 10^6$ hiPSC-CMs into the border zones was performed using ultrasound-guided (VisualSonics Vevo 2100, FUJIFILM, Toronto, Calif.) injection (FIG. 4C) and mice were treated with 1-trifluoromethoxyphenyl-3-(1-propionylpiperidine-4-yl)urea (TPPU, 15 mg/L, FIG. 2F) orally in drinking water for 3 weeks (23). The investigators were blinded to the treatment groups. A total of 98 NSG mice were used. Eight animals died in the peri-operative period, leaving a total of 90 mice in the study.

Treatment with TPPU resulted in a significant improvement in the cell retention post MI. We next investigated whether TPPU improved the survival of hiPSC-CMs after transplantation into the ischemic myocardium in the post MI model. To test the engraftment of transplanted hiPSC-CMs longitudinally, in vivo bioluminescent imaging (BLI, IVIS Xenogen Corp, Alameda, Calif.) was performed (21). BLI at 3 and 4 weeks demonstrated a significant increase in the survival of GFP+ cells in mice with TPPU treatment compared to the mice with cells only (FIGS. 2G & 2H; $7.4 \times 10^6 \pm 1.7 \times 10^6$ and $1.1 \times 10^6 \pm 5.1 \times 10^5$ photons/s/cm$^2$/sr, respectively). Quantification by flow cytometry showed a significant increase in the number of GFP+ hiPSC-CMs in the TPPU treated mice (9.9±0.5%) compared to the non-treated mice with hiPSC-CMs (4.19±0.4%, FIG. 2I).

Figure 5:
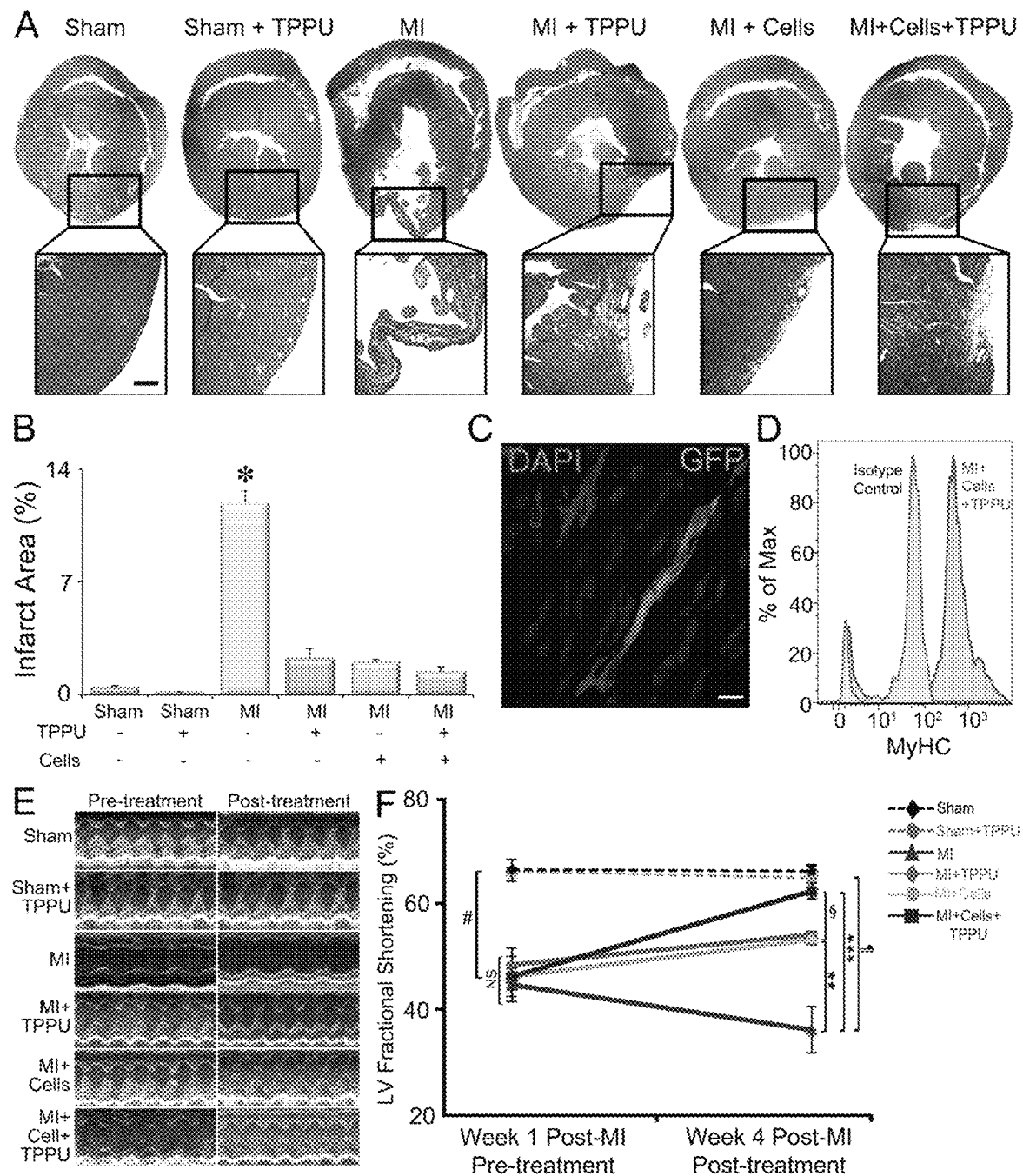
FIGS. 5A-F illustrate that TPPU improves cardiac function and decreases fibrosis as assessed by echocardiography and immunohistochemistry: (A) Cardiac sections stained with Sirius Red to demonstrate the amount of collagen deposition in the six groups of animals, Sham, Sham+TPPU, MI, MI+TPPU, MI+Cells (hiPSC-CM) and MI+Cells+TPPU. Scale bar, 200 µm. (B) Quantification of the % infarct zone. n=3 per group, *P<0.05. (C) Confocal image of cardiac sections showing the presence of GFP+ hiPSC-CMs. Scale bar=10 µM. (D) Representative myosin heavy chain (MyHC) expression in isolated GFP+ transplanted hiPSC-CMs as assessed by flow cytometry. (E) Examples of M-mode echocardiography pre- and post-treatment in the six groups of mice. (F) Summary data for % left ventricular (LV) fractional shortening (FS) pre- and post-sEHI treatment. Mean±SEM. n=6-8 per group. #P<0.05 comparing sham and sham+TPPU to other groups at week 1, § P<0.05 comparing MI+Cells=TPPU with MI+Cells at week 4, P<0.05 comparing MI with MI+Cells and MI+TPPU at week 4, *P<0.05 comparing MI with MI+Cells+TPPU at week 4, and P<0.05 comparing sham and sham+TPPU with MI at week 1 by ANOVA. Cells=hiPSC-CMs.

Reduction in cardiac fibrosis after hiPSC-CMs transplantation and TPPU treatment. To quantify the degree of fibrosis, cardiac sections (5 µM) from corresponding areas in six different groups were examined in a blinded fashion using Masson's Trichrome stain (FIG. 5A). Blinded quantification of the infarcted area at 4 weeks after MI demonstrated a significantly decrease in infarct size and the development of cardiac dilatation post MI after hiPSC-CM transplantation and in the TPPU-treated MI hearts, compared to the MI hearts (FIG. 5B). There was a further decrease in the infarct size in the TPPU+hiPSC-CM-treated hearts compared to the TPPU- or cell-treated hearts, though not significant. There were no significant differences between the two sham-operated groups as expected. The data suggest that treatment with TPPU and cells transplantation post-MI prevents adverse cardiac remodeling at least in part by reducing infarct size and cardiac fibrosis.

The engraftment of transplanted cells was assessed using immunofluorescence confocal microscopy to detect donor GFP+ cells (FIG. 5C). Flow cytometric analysis of the transplanted cells showed 86.1±0.5% of the cells positive for myosin heavy chain (FIG. 5D).

Figure 6:
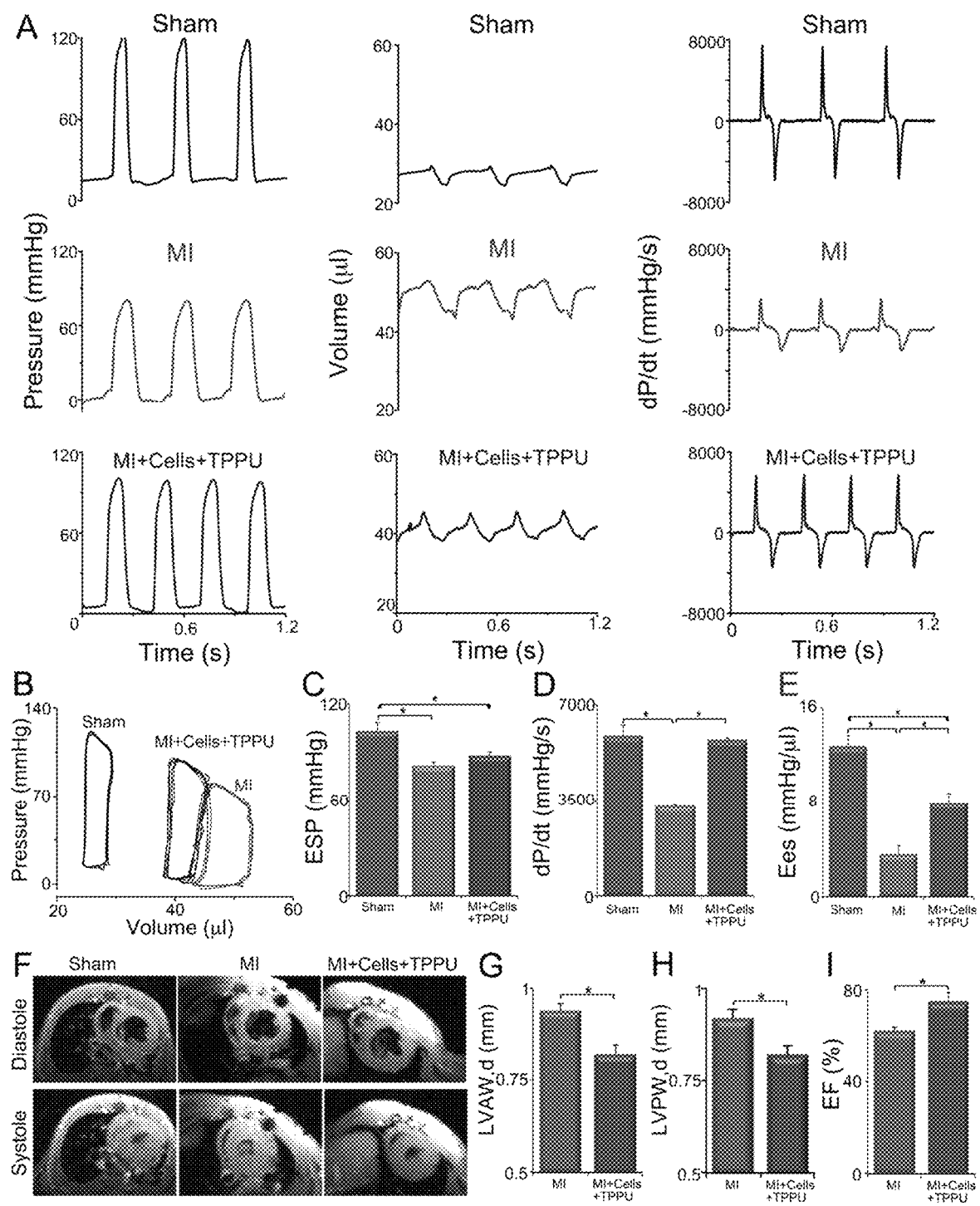
Figure 7:
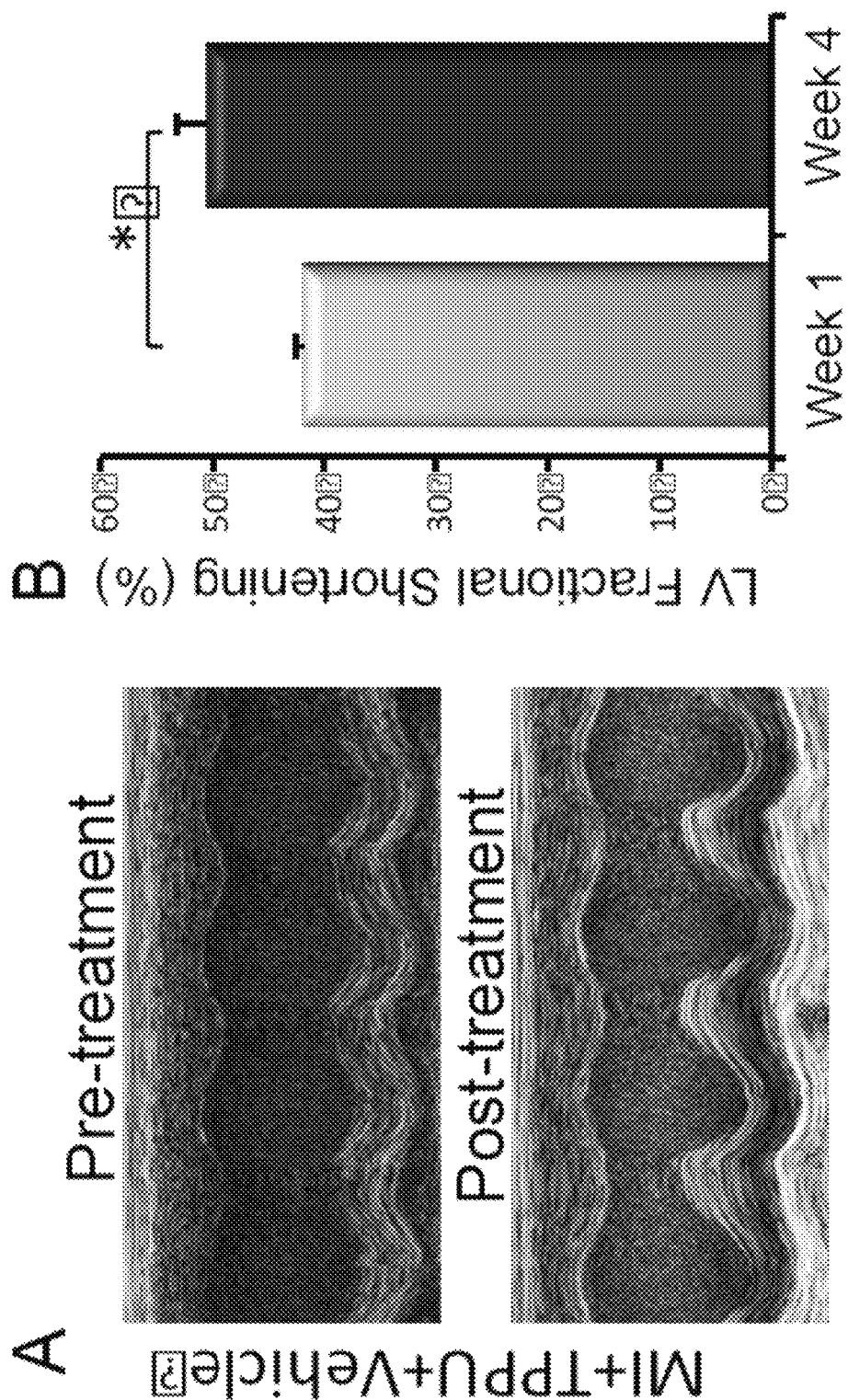
FIG. 7A-B illustrate cardiac function as assessed by echocardiography. (A) Examples of M-mode echocardiography pre- and post-treatment in the vehicle (phosphate buffered saline, PBS)-treated MI group (MI+TPPU+Vehicle). (B) Percentages of fractional shortening (FS) in mice post MI with vehicle injection and TPPU treatment (51±2%) showed a comparable improvement in FS to the MI+TPPU group (55*0.7%) suggesting no adverse effect from the vehicle injection. Mean±SEM. n=3 per group. *P<0.05.

An increase in hiPSC-CMs engraftment translated into a significant improvement in cardiac function. To assess the potential therapeutic efficacy of TPPU treatment in cell-based therapy after MI, we compared the functional recovery from six groups of animals. Functional analysis using echocardiography (FIGS. 5E and 5F) and magnetic resonance imaging (FIG. 6A) was performed to evaluate the effect of TPPU on chamber size and systolic function. Two-dimensional and M-mode echocardiography showed a significant improvement in left ventricular fractional shortening (FS) in the MI+hiPSC-CM+TPPU group after three weeks of TPPU treatment (61±2%) compared to before treatment (44±6%) (#, P<0.05). As expected, there was a significant decrease in the FS in the MI group from before (51±3%) compared to after treatment (36±4%), suggesting adverse remodeling (§, P<0.05). Vehicle injection along with MI+TPPU (51*2%) showed a comparable improvement in FS to the MI+TPPU group (55±0.7%) suggesting no adverse effect from the vehicle injection (FIG. 7). Indeed, treatment with both sEHI and cells resulted in an improvement of FS of 40%, highest compared to other treatment groups suggesting an additive effect from both TPPU and cells.

In vivo hemodynamic monitoring demonstrated an improvement in cardiac contractility with hiPSC-CMs and TPPU treatment. Hemodynamic analyses demonstrated a significant decrease in cardiac contractility in MI mice compared with sham controls. FIG. 6A shows representative recordings of left ventricular pressure, volume, and developed pressure (dP/dt) in sham, MI and MI+hiPSC-CM+TPPU mice. The right and downward shift of the pressure-volume (P-V) loops in the MI indicates reduced end-systolic pressure and relatively larger end-systolic and end-diastolic volumes (FIG. 6B) compared to the sham-operated mice, which was restored to a modest level with sEHI and hiPSC-CM treatment in the MI mice. To determine the end-systolic P-V relationship, we obtained a series of P-V loops by altering the preload and derived the slope of the end systolic P-V relationship (Ees), a load independent measure of cardiac contractility. The end-systolic pressure (ESP, FIG. 6C), maximum dP/dt (FIG. 3D) and Ees (FIG. 6E) in the MI mice were significantly reduced compared to sham-operated mice, and improved with TPPU and hiPSC-CM treatment suggesting a decrease in cardiac contractility in the MI compared to sham operated and treated mice. Taken together, these data suggest that the treatment with TPPU and hiPSC-CM prevented adverse cardiac remodeling and improved cardiac function in the MI model.

Figure 8:
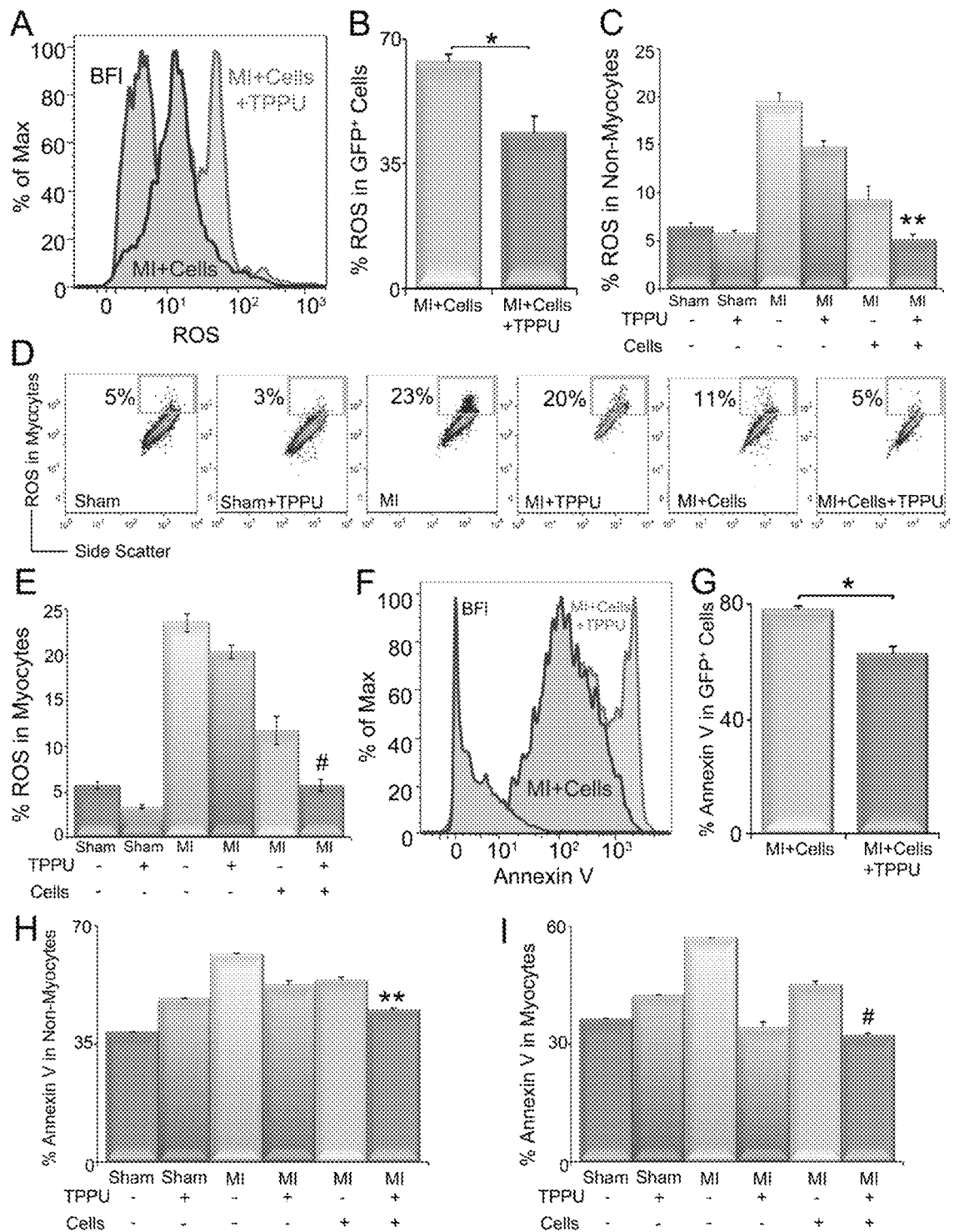
FIGS. 8A-I illustrate that flow cytometric analysis demonstrates a significant decrease in ROS and apoptosis with hiPSC-CMs and TPPU treatment from transplanted hiPSC-CMs, host cardiomyocytes and host non-myocyte cells from the MI model: (A) Flow cytometric analysis showing the median fluorescence intensity of ROS from transplanted hiPSC-CMs. (B) Summary data from (A). (C) Summary data from flow cytometric analysis of ROS from host non-myocytes. (D) Flow cytometric analysis of ROS from host cardiomyocytes. X and Y-axes represent arbitrary units. (E) Summary data from (D). (F) Flow cytometric analysis showing the median fluorescence intensity of Annexin V indicating apoptosis from transplanted hiPSC-CMs. (G) Summary data from (F). (H) Summary data from flow cytometric analysis of Annexin V from host non-myocytes. (I) Summary data from flow cytometric analysis of Annexin V from host myocytes. Representative results are shown. Mean±SEM. n=3-6 per group. *P<0.05 by ANOVA. Cells=hiPSC-CMs.

Attenuated cardiac remodeling may be attributed to reduced oxidative stress and apoptosis. One of the robust responses to cardiac tissue injury is inflammation, which activates multiple signaling pathways including mitogen-activated protein kinases (MAPK) leading to oxidative stress and apoptosis. Here, flow cytometry was used to quantify the level of oxidative stress (production of reactive oxygen species, ROS) and apoptosis in the transplanted hiPSC-CMs, host non-myocyte cells (NMCs) and cardiomyocytes (CMs) in the TPPU treated & non-treated groups using flow cytometry. To measure oxidative stress, CellRox (Life Technologies) reagent was utilized. The CellRox cell-permeable reagents are non-fluorescent while in a reduced state and upon oxidation exhibit strong fluorogenic signal. There was a significant decrease in ROS levels in hiPSC-CMs isolated from the MI+hiPSC-CM+TPPU group compared to the MI+hiPSC-CM group without sEHI treatment (FIGS. 8A and 8B). Similarly, there was a significant decrease in ROS levels in the host NMCs (FIG. 8C) and CMs (FIGS. 8D and 8E) fractions isolated from the hiPSC-CM transplanted-TPPU treated group compared to the MI, MI+hiPSC-CMs, and MI+TPPU groups.

Apoptosis quantified using single-cell based flow cytometry in the transplanted hiPSC-CM was significantly decreased with TPPU treatment (FIGS. 8F and 8G). Similarly, host NMCs and CMs isolated from the hiPSC-CM transplanted-TPPU treated group demonstrated a significant decrease in apoptosis compared to those isolated from MI, MI+hiPSC-CM, and MI+TPPU groups (FIGS. 8H and 8I, respectively).

Figure 9:
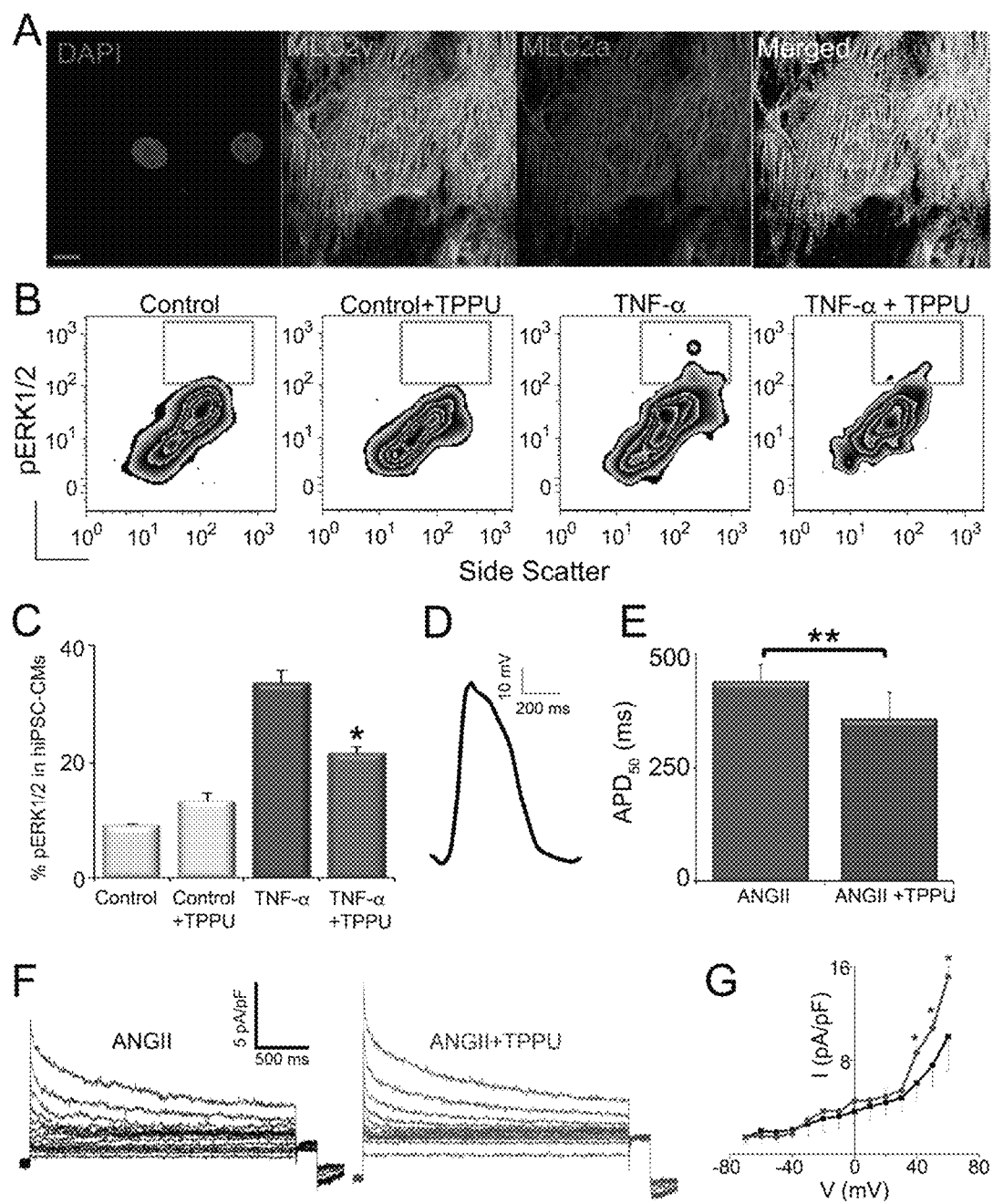
FIGS. 9A-G illustrate that treatment with TPPU results in a significant reduction in ERK1/2 and recovery of Ito and ADP50 in hiPSC-CMs in vitro: (A) Immunofluorescence confocal images of MLC2a+(red) MLC2v+(green) hiPSC-CMs. Cell nuclei were stained with DAPI (blue). Scale bar=20 µM. (B) Flow cytometric analysis of pERK1/2 signal from 4 different groups of hiPSC-CMs (no treatment, treated with TPPU, treated with TNF-α or treated with TNF-α and TPPU). X and Y-axes represent arbitrary units. (C) Summary data from (B). (D) Representative optical recordings of action potential from hiPSC-CMs. (E) Action potential duration at 50% repolarization (APD50) from hiPSC-CMs treated with ANGII alone or ANGII and TPPU. n=30-100 cells per group of biological repeats from three experiments. (F) Transient outward K+ current recordings from hiPSC-CMs and (G) the corresponding current-voltage (I-V) plot. Representative results are shown. Mean±SEM. *P<0.05 by ANOVA.
Figure 10:
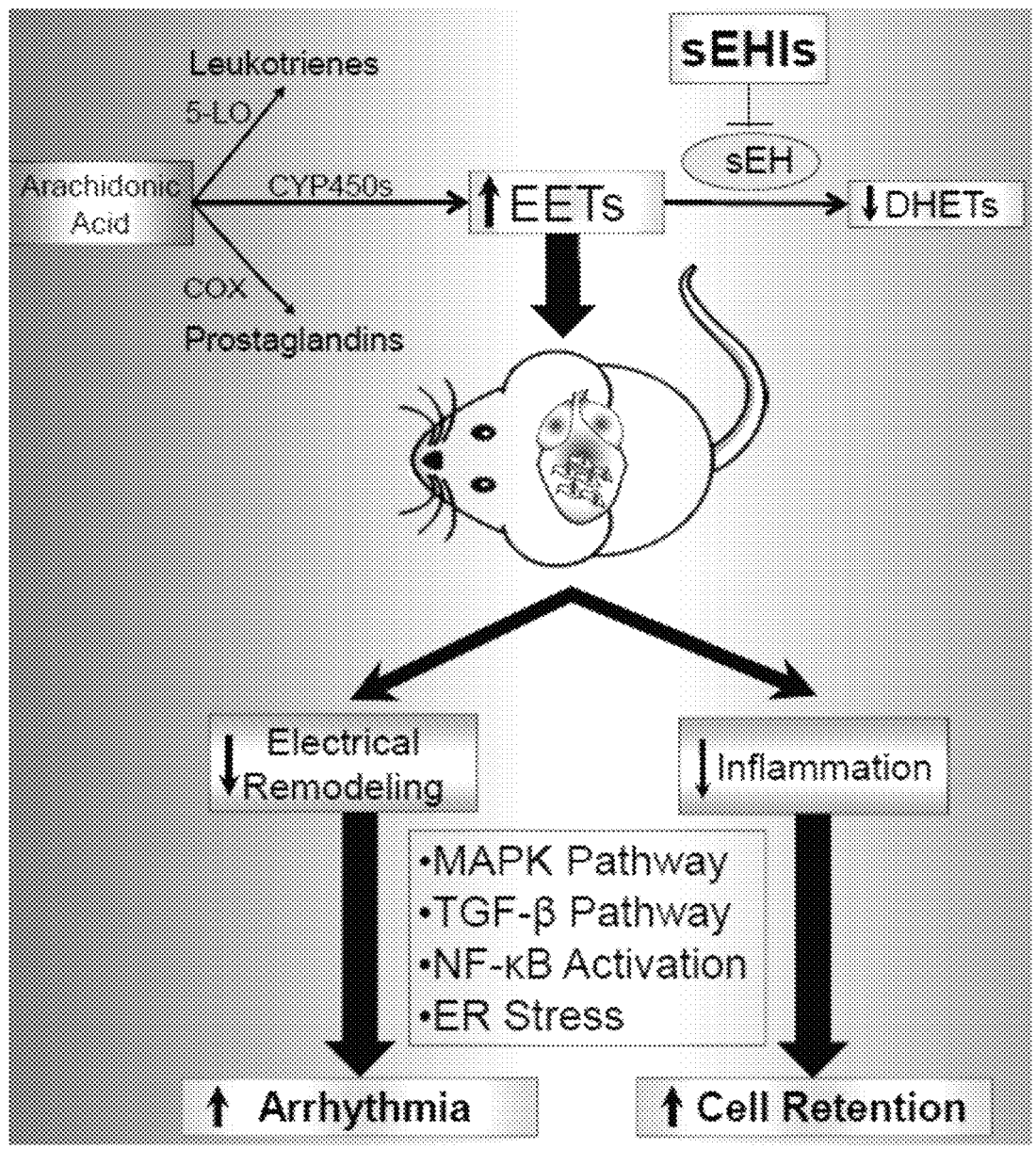
FIG. 10 provides a schematic of the mechanism by which exposing stem cells in vitro to an inhibitor of sEH prior to administration improves engraftment (e.g., in cardiac tissue) and stem cell survival.

In vitro treatment with TPPU resulted in a significant reduction in extracellular regulated kinases 1 and 2 (ERK1/2) activation. To determine the underlying mechanisms for increased oxidative stress and apoptosis in hiPSC-CMs, we examined the members of the MAPK signaling cascade, ERK1/2. Differentiated hiPSC-CMs (MLC2a+/MLC2v+, FIG. 9A) were treated using tumor necrosis factor-α (TNF-α, 20 ng/ml for 20 minutes) with or without TPPU (1 µM) in vitro. Analysis of stimulated hiPSC-CMs demonstrated a significant increase in phosphorylated ERK1/2 (pERK1/2) compared with the control and control-TPPU-treated cells (FIGS. 9B and 9C). Moreover, treatment of TNF-α stimulated hiPSC-CMs with TPPU significantly decreased the pERK1/2 level.

Treatment with TPPU prevented electrical remodeling in hiPSC-CMs challenged with angiotensin II. Finally, to determine the effects of TPPU treatment on electrical remodeling, we challenged the hiPSC-CMs with angiotensin 11 (ANGII, 1 µM for 24 hours) to assess the change in electrophysiological properties using optical and patch-clamp recordings. Action potentials of hiPSC-CMs stimulated with ANG II and recorded optically demonstrated a significant increase in action potential duration at 50% repolarization (APD50, FIGS. 9D and 9E). Treatment with TPPU prevented the increase of APD50. Consistent with the optical mapping, hiPSC-CMs activated with ANGII demonstrated a significant downregulation of the transient outward K+ current assayed using patch-clamp recordings from single hiPSC-CMs. Treatment with TPPU prevented the downregulation of the transient outward K+ current (FIGS. 9F and 9G).

Discussion

Adult cardiac myocytes are unable to proliferate sufficiently to replace the damaged tissue, therefore, stem cell therapy represents a promising approach for the treatment of HF, since it is centered on the premise of regenerating new functional myocardium and inducing neoangiogenesis. In the current study, we demonstrate the therapeutic efficacy of sEHI by attenuating inflammation in hiPSC-CM cell transplantation in a preclinical model. Treatment with sEHI results in a significant decrease in transplanted cell apoptosis and oxidative stress leading to a significant increase in the retention of hiPSC-CMs. There is an improvement in the host cardiac milieu with sEHI treatment as demonstrated by a significant decrease in apoptosis in host cardiomyocytes and non-myocytes as well as a significant decrease in the oxidative stress in the host myocardium making it more conducive to the survival of transplanted hiPSC-CMs. Finally, addition of sEHI to cardiac stem cell transplantation results in a concomitant decrease in fibrosis associated with a significant improvement in cardiac function. Mechanistically, treatment with sEHI results in a decrease in ERK1/2 activation and electrical remodeling in hiPSC-CMs. Our data provide evidence that reduction of inflammation by increasing the biological activities of EETs can improve cell engraftment by optimizing the host microenvironment and the transplanted cells. Mitigation of inflammation using sEHI in cardiac stem cell transplantation may represent an effective therapy post MI since it addresses the effects of oxidative stress and the associated inflammation-mediated fibrosis that may impede the success of the current cell-based therapies.

Current challenges in cardiac cell-based therapy. Stem cells possess the capacity for sustained proliferation, cardiac differentiation as well as trophic functions which enables myocardial repair. To date, various stem cells have been used in clinical trials with each cell type presenting several advantages and limitations (7, 8). Since the original description of iPSCs, the field has greatly expanded. Importantly, a large numbers of studies have refined the techniques for efficient directed-differentiation of iPSCs into cardiomyocytes (22, 24). In addition, multiple studies have provided evidence for the utilities of iPSC-CMs in cardiac transplantation in animal models (7). However, therapeutic strategies using cell-based therapy to combat ischemic cardiomyopathy have not produced full restorative functions (9, 10). One of the main challenges of cardiac stem cell therapy is the survival and retention of transplanted cells in the hostile milieu. A high rate of transplanted stem-cell loss, ~90% within the first few days has been observed due to ischemic environment and inflammation (25, 26). For the transplanted cells to mechanical couple with native cardiomyocytes to ultimately contract synchronously, they would first need to survive the initial robust inflammatory response associated with cardiac tissue injury.

Detrimental effects of inflammatory mediators and oxidative stress. Robust inflammatory mediators are one of the prime causes of cell death (25-27). The recruitment of inflammatory cells such as neutrophils and monocytes into the infarcted heart tissue causes the production of inflammatory cytokines such as TNF-α, interleukin-6 (IL-6), IL-1 and chemokines, which further secrete proteolytic enzymes and ROS (26-28). These mediators are severely cytotoxic and compromise survival of transplanted cells (25). IL-1 is elevated in infarcted myocardium and facilitates apoptosis of cardiomyocytes and adverse remodeling (29). Cell death further increases inflammatory responses leading to attenuation of cardiac function. In response to inflammation, stem cells produce ROS and also activate mitochondrial and endoplasmic reticulum stress and death receptor pathways eliciting apoptosis (30). Inflammation activates ERK1/2 leading to fibrosis and apoptosis, thereby reduces cell engraftment. ERK1/2 members of the MAPK superfamily are known to regulate several critical processes including stem cell differentiation, proliferation, and survival. Therefore, it is critical that the transplanted stem cells can overcome the harsh inflammatory microenvironment and survive in the injured myocardium for significant repairs to occur.

Infarction associated hypoxia increases oxidative stress in the injured myocardium. ROS is known to influence critical cellular processes including gene expression of inflammatory cytokines and growth factors, metabolic alterations, calcium handling, ionic fluxes, and apoptosis (31). ROS-induced apoptotic factors from transplanted cells further increase oxidative stress in the myocardium. Apoptosis peaks within hours after an ischemic event and is induced by both intrinsic and extrinsic factors including inflammatory cytokines. Here, we demonstrate the decrease in ROS in host cardiomyocytes and non-myocyte cells with sEHI treatment and a decrease in apoptosis in transplanted hiPSC-CMs.

Another critical barrier for stem cell engraftment is the recruitment of fibroblasts, which form physical barriers at the site of injury and inhibit cell engraftment. We have previously demonstrated the beneficial effect of sEHI on the reduction in the percentages and the proliferative capacity of the different populations of cardiac fibroblasts resulting in a significant decrease in cardiac fibrosis (19).

Current strategies to improve cardiac cell-based therapy. To combat the challenge of stem cell death in the injured myocardium immediately after transplantation, several pro-survival strategies, which either activate endogenous cellular survival mechanisms or inhibit major cell death pathways have been used (11, 32, 33). Indeed, studies have shown that inhibitors of inflammation increase cell survival by many fold (26). Various strategies have been used to improve transplanted cell survival including expression of IL-1 inhibitor and treatment with superoxide dismutase to reduce inflammation (26). Our previous data demonstrates that sEHIs are potent anti-inflammatory agents that significantly decrease the systemic levels of cytokines and chemokines (16-19, 34-39). The epoxy fatty acids reduce inflammation, acting downstream of non-steroidal anti-inflammatory drugs and lack the toxicity associated with them. In the present study, we demonstrate for the first time the broader use sEHIs in reducing inflammation to promote transplanted hiPSC-CMs survival for cardiac regenerative therapy post MI.

Finally, we show that conditioning ANGII- and TNF-α-activated hiPSC-CMs with sEHI leads to a decrease in the activation of ERK1/2 and electrical remodeling. Taken together, our data suggests that conditioning the hiPSC-CMs with sEHI may help them to better survive the harsh conditions in the ischemic myocardium.

It is well documented that paracrine factors secreted or induced by transplanted stem cells contribute significantly to the improvement in cardiac function. Our findings (FIGS. 2 and 5) are consistent with previous studies which demonstrate that despite the scarcity of survival stem cells three to four weeks after transplantation, there are still a benefit in terms of improvements in cardiac function possibly from the paracrine signals such as growth factors, chemokines and exosomes (40). These paracrine signals may activate multiple targets including attenuation of inflammation, fibrosis and apoptosis and recruitment of resident cardiac progenitor cells, which act synergistically to prevent structural and electrical remodeling. In our study, there was an increase in the BLI with sEHI treatment after cell transplantation suggesting an increase in stem cell proliferation. This may be partially attributed to the positive effect of paracrine factors on the transplanted hiPSC-CMs. Hence, paracrine signals remain to be investigated to test whether they contribute to the improvement in cardiac function with sEHI and hiPSC-CM treatment. There are other mechanisms apart from the generation of new myocardium and paracrine factors that may contribute to the beneficial impact, including mechanical stabilization, stimulation of neovascularization and cell fusion.

The selective and potent inhibitor for the sEH enzymes were developed based on the catalytic mechanism and the X-ray structure of the murine sEH (PDB access #: 1CQZ & 1CR6). In addition, the X-ray crystal structure of the sEH enzyme and the inhibitors has been solved (41-46). There is no evidence to date of off-target binding sites (47-49). However, additional studies are required to determine possible untoward side effects of these compounds.

Finally, very little is known regarding the role of this class of compounds in cell-based therapy. There is consequently an enormous opportunity to uncover a potentially very powerful class of inhibitors, which may be used effectively in the clinical setting. Our study transcends the suppression of inflammation and scar formation in cardiac cell-based therapy. Since the CYP450 pathway is evolutionarily preserved, the inhibitors have the potential to be utilized in other inflammatory-related diseases.

REFERENCES

1. Levy D, Garrison R J, Savage D D, Kannel W B, and Castelli W P. Prognostic implications of echocardiographically determined left ventricular mass in the Framingham Heart Study. N Engl J Med. 1990; 322(22): 1561-6.
2. Ho K K, Pinsky J L, Kannel W B, and Levy D. The epidemiology of heart failure: the Framingham Study. Journal of the American College of Cardiology. 1993; 22(4 Suppl A):6A-13A.
3. Dominguez L J, Parrinello G, Amato P, and Licata G. Trends of congestive heart failure epidemiology: contrast with clinical trial results. Cardiologia. 1999; 44(9):801-8.
4. Cohn J, Archibald D. Ziesche S, Franciosa J, Harston W, Tristani F, Dunkman W, Jacobs W, Francis G, Flohr K, et al. Effect of vasodilator therapy on mortality in chronic congestive heart failure: results of a veterans Administration cooperative study. N Engl J Med. 1986; 314(1547-52.
5. Gerbin K A, and Murry C E. The winding road to regenerating the human heart. Cardiovascular pathology: the official journal of the Society for Cardiovascular Pathology. 2015; 24(3):133-40.
6. Mozaffarian D, Benjamin E J, Go A S, Arnett D K, Blaha M J, Cushman M, Das S R, de Ferranti S, Despres J P, Fullerton H J, et al. Heart Disease and Stroke Statistics-2016 Update: A Report From the American Heart Association. Circulation. 2016; 133(4):e38-360.

7. Lalit P A, Hei D J, Raval A N, and Kamp T J. Induced pluripotent stem cells for post-myocardial infarction repair: remarkable opportunities and challenges. Circ Res. 2014; 114(8):1328-45.
8. Kai C Wollert hD. Clinical Applications of Stem Cells for the Heart. Circulation Research. 2005; 96(151-63.
9. Dimmeler S, and Zeiher A M. Cell therapy of acute myocardial infarction: open questions. Cardiology. 2009; 113(3):155-60.
10. Dimmeler S, and Losordo D. Stem cells review series: an introduction. Circ Res. 2011; 109(8):907-9.
11. Laflamme M A, Chen K Y, Naumova A V, Muskheli V, Fugate J A, Dupras S K, Reinecke H, Xu C, Hassanipour M, Police S, et al. Cardiomyocytes derived from human embryonic stem cells in pro-survival factors enhance function of infarcted rat hearts. Nature biotechnology. 2007; 25(9):1015-24.
12. Chen I Y, and Wu J C. Cardiovascular molecular imaging: focus on clinical translation. Circulation. 2011; 123(4):425-43.
13. Zhang W Y, Ebert A D, Narula J, and Wu J C. Imaging cardiac stem cell therapy: translations to human clinical studies. Journal of cardiovascular translational research. 2011; 4(4):514-22.
14. Spector A A, Fang X, Snyder G D, and Weintraub N L. Epoxyeicosatrienoic acids (EETs): metabolism and biochemical function. Progress in lipid research. 2004; 43(1): 55-90.
15. Morisseau C, and Hammock B D. Epoxide hydrolases: mechanisms, inhibitor designs, and biological roles. Annu Rev Pharmacol Toxicol. 2005; 45(311-33.
16. Chiamvimonvat N, Ho C M, Tsai H J, and Hammock B D. The soluble epoxide hydrolase as a pharmaceutical target for hypertension. J Cardiovasc Pharmacol. 2007; 50(3):225-37.
17. Li N, Liu J Y, Qiu H, Harris T R, Sirish P, Hammock B D, and Chiamvimonvat N. Use of metabolomic profiling in the study of arachidonic acid metabolism in cardiovascular disease. Congest Heart Fail. 2011; 17(1):42-6.
18. Li N, Liu J Y, Timofcyev V, Qiu H, Hwang S H, Tuteja D, Lu L, Yang J, Mochida H, Low R, et al. Beneficial effects of soluble epoxide hydrolase inhibitors in myocardial infarction model: Insight gained using metabolomic approaches. J Mol Cell Cardiol. 2009; 47(6):835-45.
19. Sirish P, Li N, Liu J Y, Lee K S, Hwang S H, Qiu H, Zhao C, Ma S M, Lopez J E, Hammock B D, et al. Unique mechanistic insights into the beneficial effects of soluble epoxide hydrolase inhibitors in the prevention of cardiac fibrosis. Proc Natl Acad Sci USA. 2013; 110(14):5618-23.
20. Sirish P, Li N, Timofeyev V, Zhang X D, Wang L, Yang J, Lee K S, Bettaieb A, Ma S M, Lee J H, et al. Molecular Mechanisms and New Treatment Paradigm for Atrial Fibrillation. Circulation Arrhythmia and electrophysiology. 2016; 9(5).
21. Lee A S, and Wu J C. Imaging of embryonic stem cell migration in vivo. Methods Mol Biol. 2011; 750(101-14.
22. Lian X, Hsiao C, Wilson G, Zhu K, Hazeltine L B, Azarin S M, Raval K K, Zhang J, Kamp T J, and Palecek S P. Robust cardiomyocyte differentiation from human pluripotent stem cells via temporal modulation of canonical Wnt signaling. Proc Natl Acad Sci USA. 2012; 109 (27):E1848-57.
23. Singla D K, Hacker T A, Ma L, Douglas P S, Sullivan R, Lyons G E, and Kamp T J. Transplantation of embryonic stem cells into the infarcted mouse heart: formation of multiple cell types. J Mol Cell Cardiol. 2006; 40(1): 195-200.
24. Takahashi K, and Yamanaka S. Induction of pluripotent stem cells from mouse embryonic and adult fibroblast cultures by defined factors. Cell. 2006; 126(4):663-76.
25. Der Sarkissian S, Lvesque T, and Noiseux N. Optimizing stem cells for cardiac repair: Current status and new frontiers in regenerative cardiology. World journal of stem cells. 2017; 9(1):9-25.
26. Don C W, and Murry C E. Improving survival and efficacy of pluripotent stem cell-derived cardiac grafts. Journal of cellular and molecular medicine. 2013; 17(11): 1355-62.
27. Shi R Z, and Li Q P. Improving outcome of transplanted mesenchymal stem cells for ischemic heart disease. Biochemical and biophysical research communications. 2008; 376(2):247-50.
28. Aurora A B, and Olson E N. Immune modulation of stem cells and regeneration. Cell stem cell. 2014; 15(1):14-25.
29. Maekawa Y, Mizue N, Chan A, Shi Y, Liu Y, Dawood S, Chen M, Dawood F, de Couto G, Li G H, et al. Survival and cardiac remodeling after myocardial infarction are critically dependent on the host innate immune interleukin-1 receptor-associated kinase-4 signaling: a regulator of bone marrow-derived dendritic cells. Circulation. 2009; 120(14):1401-14.
30. Rodrigues M, Turner O, Stolz D, Griffith L G, and Wells A. Production of reactive oxygen species by multipotent stromal cells/mesenchymal stem cells upon exposure to fas ligand. Cell transplantation. 2012; 21(10):2171-87.
31. Giordano F J. Oxygen, oxidative stress, hypoxia, and heart failure. The Journal of clinical investigation. 2005; 115(3):500-8.
32. Yc L, Chang Y H, Xiong Q, Zhang P, Zhang L, Somasundaram P, Lepley M, Swingen C, Su L, Wendel J S, et al. Cardiac repair in a porcine model of acute myocardial infarction with human induced pluripotent stem cell-derived cardiovascular cells. Cell stem cell. 2014; 15(6):750-61.
33. Robey T E, Saiget M K, Reinecke H, and Murry C E. Systems approaches to preventing transplanted cell death in cardiac repair. J Mol Cell Cardiol. 2008; 45(4):567-81.
34. Ai D, Pang W, Li N, Xu M, Jones P D, Yang J, Zhang Y, Chiamvimonvat N, Shyy J Y, Hammock B D, et al. Soluble epoxide hydrolase plays an essential role in angiotensin II-induced cardiac hypertrophy. Proc Natl Acad Sci USA. 2009; 106(2):564-9.
35. Harris T R, Li N, Chiamvimonvat N, and Hammock B D. The potential of soluble epoxide hydrolase inhibition in the treatment of cardiac hypertrophy. Congest Heart Fail. 2008; 14(4):219-24.
36. Liu J Y, Li N, Yang J, Qiu H, Ai D, Chiamvimonvat N, Zhu Y, and Hammock B D. Metabolic profiling of murine plasma reveals an unexpected biomarker in rofecoxib-mediated cardiovascular events. Proc Natl Acad Sci USA. 2010; 107(39):17017-22.
37. Liu J Y, Yang J, Inceoglu B, Qiu H, Ulu A, Hwang S H, Chiamvimonvat N, and Hammock B D. Inhibition of soluble epoxide hydrolase enhances the anti-inflammatory effects of aspirin and 5-lipoxygenase activation protein inhibitor in a murine model. Biochem Pharmacol. 2010; 79(6):880-7.
38. Qiu H, Li N, Liu J Y, Harris T R, Hammock B D, and Chiamvimonvat N. Soluble Epoxide Hydrolase Inhibitors and Heart Failure. Cardiovasc Ther. 2011.
39. Xu D, Li N, He Y, Timofeyev V, Lu L, Tsai H J, Kim I H, Tuteja D, Mateo R K, Singapuri A, et al. Prevention and reversal of cardiac hypertrophy by soluble epoxide hydrolase inhibitors. Proc Natl Acad Sci USA. 2006; 103(49):18733-8.
40. Chimenti I, Smith R R, Li T S, Gerstenblith G, Messina E, Giacomello A, and Marban E. Relative roles of direct regeneration versus paracrine effects of human cardiosphere-derived cells transplanted into infarcted mice. Circ Res. 2010; 106(5):971-80.
41. Gomez G A, Morisseau C, Hammock B D, and Christianson D W. Structure of human epoxide hydrolase reveals mechanistic inferences on bifunctional catalysis in epoxide and phosphate ester hydrolysis. Biochemistry. 2004; 43(16):4716-23.
42. Xing L, McDonald J J, Kolodziej S A, Kurumbail R G, Williams J M, Warren C J, O'Neal J M, Skepner J E, and Roberds S L. Discovery of potent inhibitors of soluble epoxide hydrolase by combinatorial library design and structure-based virtual screening. J Med Chem. 2011; 54(5):1211-22.
43. Moser D, Achenbach J, Klingler F M, Estel la B, Hahn S, and Proschak E. Evaluation of structure-derived pharmacophore of soluble epoxide hydrolase inhibitors by virtual screening. Bioorganic & medicinal chemistry letters. 2012; 22(21):6762-5.
44. Amano Y, Yamaguchi T, and Tanabe E. Structural insights into binding of inhibitors to soluble epoxide hydrolase gained by fragment screening and X-ray crystallography. Bioorganic & medicinal chemistry. 2014; 22(8):2427-34.
45. Takai K, Chiyo N, Nakajima T, Nariai T, Ishikawa C, Nakatani S, Ikeno A, Yamamoto S, and Sone T. Three-dimensional rational approach to the discovery of potent substituted cyclopropyl urea soluble epoxide hydrolase inhibitors. Bioorganic & medicinal chemistry letters. 2015; 25(8):1705-8.
46. Amano Y, Tanabe E, and Yamaguchi T. Identification of N-ethylmethylamine as a novel scaffold for inhibitors of soluble epoxide hydrolase by crystallographic fragment screening. Bioorganic & medicinal chemistry. 2015; 23(10):2310-7.
47. Argiriadi M A, Morisseau C, Goodrow M H, Dowdy D L, Hammock B D, and Christianson D W. Binding of alkylurea inhibitors to epoxide hydrolase implicates active site tyrosines in substrate activation. J Biol Chem. 2000; 275(20):15265-70.
48. Argiriadi M A, Morisseau C, Hammock B D, and Christianson D W. Detoxification of environmental mutagens and carcinogens: structure, mechanism, and evolution of liver epoxide hydrolase. Proc Natl Acad Sci USA. 1999; 96(19):10637-42.
49. Morisseau C, Goodrow M H, Dowdy D, Zheng J, Greene J F, Sanborn J R, and Hammock B D. Potent urea and carbamate inhibitors of soluble epoxide hydrolases. Proc Natl Acad Sci USA. 1999; 96(16):8849-54.
50. Ulu A, Appt S, Morisseau C, Hwang S H, Jones P D, Rose T E, Dong H, Lango J, Yang J, Tsai H J, et al. Pharmacokinetics and in vivo potency of soluble epoxide hydrolase inhibitors in cynomolgus monkeys. Br J Pharmacol. 2012; 165(5):1401-12.
51. Gomez G A, Morisseau C, Hammock B D, and Christianson D W. Human soluble epoxide hydrolase: structural basis of inhibition by 4-(3-cyclohexylureido)-carboxylic acids. Protein science: a publication of the Protein Society. 2006; 15(1):58-64.
52. Garriga M, and Caballero J. Insights into the structure of urea-like compounds as inhibitors of the juvenile hormone epoxide hydrolase (JHEH) of the tobacco hornworm Manduca sexta: analysis of the binding modes and structure-activity relationships of the inhibitors by docking and CoMFA calculations. Chemosphere. 2011; 82(11):1604-13.
53. Hwang S H, Tsai H J, Liu J Y, Morisseau C, and Hammock B D. Orally bioavailable potent soluble epoxide hydrolase inhibitors. J Med Chem. 2007; 50(16): 3825-40.
54. Lian X, Zhang J, Azarin S M, Zhu K, Hazeltine L B, Bao X, Hsiao C, Kamp T J, and Palecek S P. Directed cardiomyocyte differentiation from human pluripotent stem cells by modulating Wnt/beta-catenin signaling under fully defined conditions. Nature protocols. 2013; 8(1):162-75.

It is understood that the examples and embodiments described herein are for illustrative purposes only and that various modifications or changes in light thereof are suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of increasing, improving and/or promoting the survival, engraftment, and/or integration of transplanted stem cells in a tissue of a subject in need thereof, comprising:
   a) exposing a population stem cells in vitro to an agent that increases the production and/or level of epoxy fatty acids (EpFA), or mimics thereof, under conditions and for a time sufficient to increase epoxy fatty acids (EpFA) and/or inhibit soluble epoxide hydrolase in the stem cells, thereby producing preconditioned stem cells; and
   b) administering to the subject the preconditioned stem cells, wherein the stem cells are selected from multipotent stem cells, pluripotent stem cells, and induced pluripotent stem cells.

2. The method of claim 1, wherein the stem cells are exposed in vitro to the agent at a concentration between about 0.1 nM to about 20 µM.

3. The method of claim 1, wherein the stem cells are exposed in vitro to the agent for a time period between about 0.5 days to about 10 days.

4. The method of claim 1, further wherein the preconditioned stem cells are co-administered to the subject with an agent that increases the production and/or level of epoxy fatty acids (EpFA), or mimics thereof.

5. The method of claim 1, wherein the subject has cardiomyopathy or heart failure.

6. The method of claim 5, wherein the cardiomyopathy is one or more of hypertrophic cardiomyopathy, hypertensive cardiomyopathy, diabetic cardiomyopathy, ischemic cardiomyopathy, restrictive cardiomyopathy and dilated cardiomyopathy.

7. The method of claim 5, wherein said cardiomyopathy is due to or secondary to one or more of valvular heart disease, myocardial infarction, ischemic cardiomyopathy, restrictive cardiomyopathy, arrhythmogenic right ventricular cardiomyopathy (ARVC) or familial hypertrophic cardiomyopathy.

8. The method of claim 5, wherein the cardiomyopathy is dilated cardiomyopathy.

9. The method of claim 8, wherein said dilated cardiomyopathy is one or more of alcohol-induced cardiomyopathy, drug-induced cardiomyopathy, viral-induced cardiomyopathy, familial dilated cardiomyopathy and dilated cardiomyopathy is caused by administration of an anti-cancer drug or exposure to a toxic agent.

10. The method of claim 1, wherein the administration of said stem cells and said agent or agents inhibits cardiac arrhythmia.

11. The method of claim 1, wherein the agent that increases the production and/or level of epoxy fatty acids (EpFA) is an inhibitor of soluble epoxide hydrolase ("sEH").

12. The method of claim 11, wherein the inhibitor of sEH is selected from the group consisting of:
  a) 3-(4-chlorophenyl)-1-(3,4-dichlorphenyl)urea or 3,4,4'-trichlorocarbanilide (TCC; compound 295);
  b) 12-(3-adamantan-1-yl-ureido) dodecanoic acid (AUDA; compound 700);
  c) 1-adamantanyl-3-{5-[2-(2-ethoxyethoxy)ethoxy]pentyl]}urea (AEPU; compound 950);
  d) 1-(1-acetypiperidin-4-yl)-3-adamantanylurea (APAU; compound 1153);
  e) trans-4-[4-(3-Adamantan-1-yl-ureido)-cyclohexyloxy]-benzoic acid (tAUCB; compound 1471);
  f) cis-4-[4-(3-Adamantan-1-yl-ureido)-cyclohexyloxy]-benzoic acid (cAUCB; compound 1686);
  g) 1-(1-methylsulfonyl-piperidin-4-yl)-3-(4-trifluoromethoxy-phenyl)-urea (TUPS; compound 1709);
  h) trans-4-{4-[3-(4-Trifluoromethoxy-phenyl)-ureido]-cyclohexyloxy}-benzoic acid (tTUCB; compound 1728);
  i) 1-trifluoromethoxyphenyl-3-(1-propionylpiperidin-4-yl) urea (TPPU; compound 1770);
  j) 1-(1-ethylsulfonyl-piperidin-4-yl)-3-(4-trifluoromethoxy-phenyl)-urea (TUPSE; compound 2213);
  k) 1-(1-(cyclopropanecarbonyl)piperidin-4-yl)-3-(4-(trifluoromethoxy)phenyl)urea (CPTU; compound 2214);
  l) trans-N-methyl-4-[4-(3-Adamantan-1-yl-ureido)-cyclohexyloxy]-benzamide (tMAUCB; compound 2225);
  m) trans-N-methyl-4-[4-((3-trifluoromethyl-4-chlorophenyl)-ureido)-cyclohexyloxy]-benzamide (tMTCUCB; compound 2226);
  n) cis-N-methyl-4-{4-[3-(4-trifluoromethoxy-phenyl)-ureido]-cyclohexyloxy}-benzamide (cMTUCB; compound 2228);
  o) 1-cycloheptyl-3-(3-(1,5-diphenyl-1H-pyrazol-3-yl)propyl)urea (HDP$_3$U; compound 2247);
  p) trans-2-(4-(4-(3-(4-trifluoromethoxy-phenyl)-ureido)-cyclohexyloxy)-benzamido)-acetic acid (compound 2283);
  q) N-(methylsulfonyl)-4-(trans-4-(3-(4-trifluoromethoxy-phenyl)-ureido)-cyclohexyloxy)-benzamide (compound 2728);
  r) 1-(trans-4-(4-(1H-tetrazol-5-yl)-phenoxy)-cyclohexyl)-3-(4-(trifluoromethoxy)-phenyl)-urea (compound 2806);
  s) 4-(trans-4-(3-(2-fluorophenyl)-ureido)-cyclohexyloxy)-benzoic acid (compound 2736);
  t) 4-(4-(3-(4-(trifluoromethoxy)-phenyl)-ureido)-phenoxy)-benzoic acid (compound 2803);
  u) 4-(3-fluoro-4-(3-(4-(trifluoromethoxy)-phenyl)-ureido)-phenoxy)-benzoic acid (compound 2807);
  v) N-hydroxy-4-(trans-4-(3-(4-(trifluoromethoxy)-phenyl)-ureido)-cyclohexyloxy)-benzamide (compound 2761);
  w) (5-methyl-2-oxo-1,3-dioxol-4-yl)methyl 4-((1r,4r)-4-(3-(4-(trifluoromethoxy)-phenyl)-ureido)-cyclohexyloxy)-benzoate (compound 2796);
  x) 1-(4-oxocyclohexyl)-3-(4-(trifluoromethoxy)-phenyl)-urea (compound 2809);
  y) methyl 4-(4-(3-(4-(trifluoromethoxy)-phenyl)-ureido)-cyclohexylamino)-benzoate (compound 2804);
  z) 1-(4-(pyrimidin-2-yloxy)-cyclohexyl)-3-(4-(trifluoromethoxy)-phenyl)-urea (compound 2810);
  aa) 4-(trans-4-(3-(4-(difluoromethoxy)-phenyl)-ureido)-cyclohexyloxy)-benzoic acid (compound 2805);
  bb) (1R,3S)—N-(4-cyano-2-(trifluoromethyl)benzyl)-3-((4-methyl-6-(methylamino)-1,3,5-triazin-2-yl)amino)cyclohexane-1-carboxamide (GSK2256294A);
  cc) sorafenib (4-(4-(3-(4-chloro-3-4-[[4-chloro-3-(trifluoromethyl)phenyl]carbamoylamino]phenoxy]-N-methylpyridine-2-carboxamide);
  dd) regorafenib (4-[4-[[4-chloro-3-(trifluoromethyl)phenyl]carbamoylamino]-3-fluorophenoxy]-N-methylpyridine-2-carboxamide);
  ee) triclocarban (3-(4-chlorophenyl)-1-(3,4-dichlorphenyl)urea or 3,4,4'-trichlorocarbanilide);
and mixtures thereof.

13. The method of claim 11, wherein the inhibitor of sEH is selected from the group consisting of 1-(3-fluoro-4-(trifluoromethoxy)phenyl)-3-(1-(tetrahydro-2H-pyran-4-carbo-nyl)piperidin-4-yl)urea (Compound 29 of Table 3) and 1-trifluoromethoxyphenyl-3-(1-propionylpiperidin-4-yl) urea (TPPU).

14. The method of claim 1, wherein the agent that increases the production and/or level of epoxy fatty acids (EpFA) is a compound in Table 4 selected from the group consisting of:
  a) compound 1860 (1-Adamantan-1-yl-3-[1-(4-methanesulfonyl-phenyl)-5-phenyl-1H-pyrazol-3-ylmethyl]-urea),
  b) compound 2321 (1-Cycloheptyl-3-[1-(4-methanesulfonyl-phenyl)-5-phenyl-1H-pyrazol-3-ylmethyl]-urea),
  c) compound 2322 (1-[1-(4-Methanesulfonyl-phenyl)-5-phenyl-1H-pyrazol-3-ylmethyl]-3-phenyl-urea),
  d) compound 2323 (1-[1-(4-Methanesulfonyl-phenyl)-5-phenyl-1H-pyrazol-3-ylmethyl]-3-(4-trifluoromethoxy-phenyl)-urea),
  e) compound 2324 (1-[1-(4-Methanesulfonyl-phenyl)-5-phenyl-1H-pyrazol-3-ylmethyl]-3-(4-trifluoromethyl-phenyl)-urea),
  f) compound 1861 (1-[1-(4-Methanesulfonyl-phenyl)-5-phenyl-1H-pyrazol-3-ylmethyl]-3-(3-trifluoromethyl-phenyl)-urea),
  g) compound 2107 (4-{5-Phenyl-3-[3-(3-trifluoromethyl-phenyl)-ureidomethyl]-pyrazol-1-yl}-benzenesulfonamide),
  h) compound 2106 (1-[5-tert-Butyl-1-(4-methanesulfonyl-phenyl)-1H-pyrazol-3-ylmethyl]-3-(3-trifluoromethyl-phenyl)-urea),
  i) compound 2121 (4-{5-Phenyl-3-[3-(3-trifluoromethyl-phenyl)-ureido]-pyrazol-1-yl}-benzenesulfonamide),
  j) compound 2313 (4-(5-Phenyl-3-{2-[3-(3-trifluoromethyl-phenyl)-ureido]-ethyl}-pyrazol-1-yl}-benzenesulfonamide),
  compound 1862 (1-{3-[1-(4-Methanesulfonyl-phenyl)-5-phenyl-1H-pyrazol-3-yl]-propyl}-3-(3-trifluoromethyl-phenyl)-urea),
  k) compound 2246 (4-(5-Phenyl-3-{3-[3-(3-trifluoromethyl-phenyl)-ureido]-propyl}-pyrazol-1-yl)-benzenesulfonamide),
  l) compound 2152 (4-(5-p-Tolyl-3-{3-[3-(3-trifluoromethyl-phenyl)-ureido]-propyl}-pyrazol-1-yl)-benzenesulfonamide),
  m) compound 2325 (4-(3-{3-[3-(2,6-Diisopropyl-phenyl)-ureido]-propyl}-5-phenyl-pyrazol-1-yl)-benzenesulfonamide), n) compound 2245 (4-{5-Phenyl-3-[3-(3-phenyl-ureido)-propyl]-pyrazol-1-yl}-benzenesulfonamide),
o) compound 2326 (4-{3-[3-(3-Adamantan-1-yl-ureido)-propyl]-5-phenyl-pyrazol-1-yl}-benzenesulfonamide),
p) compound 2247 (4-{3-[3-(3-Cycloheptyl-ureido)-propyl]-5-phenyl-pyrazol-1-yl}-benzenesulfonamide),
q) compound 2327 (4-(3-{3-[3-(4-Chloro-phenyl)-ureido]-propyl}-5-phenyl-pyrazol-1-yl)-benzenesulfonamide),
r) compound 2328 (4-(5-Phenyl-3-{3-[3-(4-trifluoromethyl-phenyl)-ureido]-propyl}-pyrazol-1-yl)-benzenesulfonamide); and
s) compound 2329 (4-(5-Phenyl-3-{3-[3-(4-trifluoromethoxy-phenyl)-ureido]-propyl}-pyrazol-1-yl)-benzenesulfonamide).

15. The method claim 1, wherein the stem cells are human induced pluripotent stem cells (hiPSCs)—derived cardiomyocytes (hiPSC-CMs).

16. The method of claim 1, wherein the tissue is cardiac tissue.

* * * * *